United States Patent [19]

Tsuruoka et al.

[11] Patent Number: 4,785,090
[45] Date of Patent: Nov. 15, 1988

[54] CEPHALOSPORIN DERIVATIVES

[75] Inventors: Takashi Tsuruoka, Kawasaki; Seiji Shibahara, Machida; Katsuyoshi Iwamatsu, Yokohama; Tsuneo Okonogi, Yokohama; Satoru Nakabayashi, Kawasaki; Yasushi Murai, Yokosuka; Hiroko Ogino, Kawasaki; Kiyoaki Katano, Yokohama; Takashi Yoshida, Tokyo; Shigeharu Inoue, Yokohama; Shunzo Fukatsu, Tokyo; Shinichi Kondo, Yokohama, all of Japan

[73] Assignee: Meiji Seika Kaisha, Ltd., Tokyo, Japan

[21] Appl. No.: 704,077

[22] Filed: Feb. 21, 1985

[30] Foreign Application Priority Data

Feb. 23, 1984 [JP] Japan .................... 59-33747
Apr. 9, 1984 [JP] Japan .................... 59-71414
Jul. 3, 1984 [JP] Japan .................... 59-138206
Dec. 1, 1984 [JP] Japan .................... 59-254517

[51] Int. Cl.$^4$ ................. C07D 501/38; A61K 31/545
[52] U.S. Cl. ...................... 540/225; 540/227
[58] Field of Search ............... 544/25, 26, 27; 514/203, 204, 205, 207; 540/225, 227

[56] References Cited

U.S. PATENT DOCUMENTS

| 4,399,131 | 8/1983 | Dunkheimer et al. | 540/229 |
| 4,495,182 | 1/1983 | Terajii et al. | 540/225 |
| 4,504,477 | 3/1985 | O'Cullagham | 544/25 |
| 4,593,022 | 6/1986 | Labeew et al. | 540/225 |

Primary Examiner—Nicholas S. Rizzo
Attorney, Agent, or Firm—James J. Ralabate

[57] ABSTRACT

This is a class of antibacterial compounds of the formula:

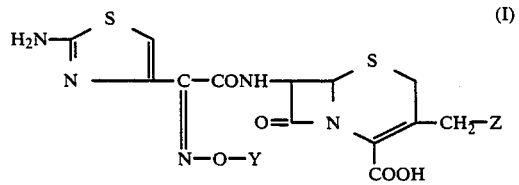

wherein Y is straight or branched alkyl or alkenyl chain, cycloalkanomethyl of 3-6 carbon atoms, each group being optionally substituted by halogen, or a group

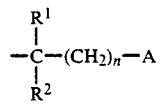

wherein n is 0 or an integer of 1-3, A is a group —COR$^3$ wherein R$^3$ is hydroxy, a group

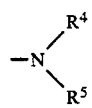

wherein R$^4$ and R$^5$, which may be the same or different, are hydrogen or alkyl of 1-5 carbon atoms, a group

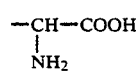

or a 5- or 6-membered heterocyclic group containing nitrogen and/or sulfur, and R$^1$ and R$^2$, which may be the same or different, are hydrogen, alkyl of 1-5 carbon atoms, or R$^1$ and R$^2$ may be combined together to form cycloalkylidene of 3-5 carbon atoms, and Z is a group of the formula:

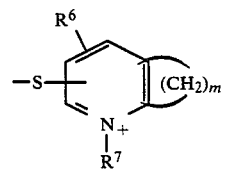

wherein m is 0 or an integer of 3-5, R$^6$ is hydrogen or alkyl of 1-3 carbon atoms, and R$^7$, when m is an integer of 3-5, is alkyl of 1-5 carbon atoms, alkenyl, cyclopropyl, a group —(CH$_2$)$_p$B wherein p is 0 or an integer of 1-3 and B is amino, alkyl-substituted amino, hydroxy, carboxy, carbamoyl, trifluoromethyl, sulfonic acid, sulfonic acid amide, alkylthio or cyano or, when m is 0, is alkyl of 1-5 carbon atoms, which may optionally be substituted by halogen, alkenyl, a group

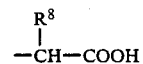

wherein R$^8$ is hydrogen, alkyl of 1-4 carbon atoms or phenyl, or cyclopropyl, and a salt thereof.

13 Claims, No Drawings

CEPHALOSPORIN DERIVATIVES

BACKGROUND OF THE INVENTION

1. Field of the Invention

This invention relates to novel cephalosporin compounds and pharmacologically acceptable salts thereof having strong antibacterial activity against Gram positive organisms as well as Gram negative organisms.

2. Description of the Prior Art

Heretofore, cephalosporin type antibiotics have been obtained in very wide varieties. The antibacterial activity of these cephalosporin type antibiotics greatly varies depending on the kind of the substituent at the 3-position in addition to the acyl group at the 7-position of the cephem nucleus. While several cephem type antibiotics having a substituted pyridiniumthiomethyl group at the 3-position are known (for example, Japanese patent application laid-open No. 154787/1979, 89289/1980 and 90590/1983), examples used clinically have not yet been known.

Furthermore, in recent years, the various infections due to Gram positive pathogens including staphylococci has been increasing markedly, accompanied with an increase in the prevalent use of the so-called 3rd generation cephalosporins. This brought about the clinically serious problems.

As the result of our intensive study on cephalosporin compounds having a substituted pyridiniumthiomethyl group as a substituent at the 3-position of the cephem nucleus, it has now been discovered that novel cephalosporin compounds having a group of the formula:

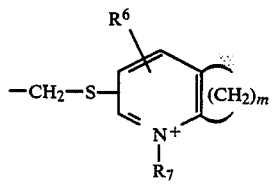

have strong antibacterial activity against Gram positive organisms as well as Gram negative organisms, and accordingly the object of this invention is to provide said compounds which have overcome the drawback of the above-described third generation cephem type antibiotics and its pharmacologically acceptable salts thereof and the process for their production.

SUMMARY OF THE INVENTION

This invention provides a cephalosporin derivative of the formula:

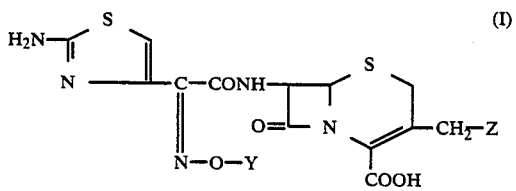

wherein

Y is straight or branched alkyl or alkenyl chain, cycloalkanomethyl of 3–6 carbon atoms, each group being optionally substituted by halogen, or a group

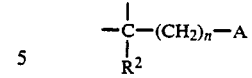

wherein n is 0 or an integer of 1–3, A is a group —$COR^3$ wherein $R^3$ is hydroxy, a group

wherein $R^4$ and $R^5$, which may be the same or different, are hydrogen or alkyl of 1–5 carbon atoms, a group

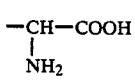

or a 5- or 6-membered heterocyclic group containing nitrogen and/or sulfur, and $R^1$ and $R^2$, which may be the same or different, are hydrogen, alkyl of 1–5 carbon atoms, or $R^1$ and $R^2$ may be combined together to form cycloalkylidene of 3–5 carbon atoms, and Z is a group of the formula:

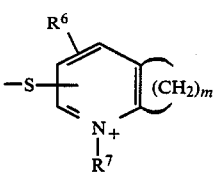

wherein m is 0 or an integer of 3–5, $R^6$ is hydrogen or alkyl of 1–3 carbon atoms, and $R^7$, when m is an integer of 3–5, is alkyl of 1–5 carbon atoms, alkenyl, cyclopropyl, a group —$(CH_2)_pB$ wherein p is 0 or an integer of 1–3 and B is amino, alkyl-substituted amino, hydroxy, carboxy, carbamoyl, trifluoromethyl, sulfonic acid, sulfonic acid amide, alkylthio or cyano or, when m is 0, is alkyl of 1–5 carbon atoms, which may optionally be substituted by halogen, alkenyl, a group

wherein $R^8$ is hydrogen, alkyl of 1–4 carbon atoms or phenyl, or cyclopropyl, and a pharmacologically acceptable salt thereof.

DETAILED DESCRIPTION OF THE INVENTION

Examples of the group Y of the compounds of the above formula (I) of this invention include straight-chain or branched-chain alkyl groups such as methyl, ethyl, propyl, butyl, isopropyl, isobutyl etc., these groups further substituted by halogen atom(s), such as difluoromethyl, 2-fluoroethyl, 2,2,2-trifluoroethyl etc., alkenyl groups such as allyl, cycloalkanomethyl groups such as cyclopropylmethyl, cyclohexylmethyl etc., carboxymethyl, 2-carboxyethyl, 2-carboxypropyl, 1-methyl-2-carboxyethyl, 1-methyl-1-carboxyethyl, carbamoylmethyl, N-methylcarbamoylmethyl, N,N-dimethylcarbamoylmethyl, 2-amino-2-carboxyethyl, 3-amino-3-carboxypropyl, 1-methyl-2-amino-2-carboxyethyl, 2-amino-3-carboxypropyl, (pyridin-2-yl)methyl, (imidazol-4-yl)methyl, (5-methylimidazol-4-yl)methyl, (2-methylimidazol-4-yl)methyl, (2-aminothiazol-4-yl)methyl, (1,2,3-triazol-4-yl)methyl, (1,2,4-triazol-3-yl)methyl etc.

Specific examples of the substituent at the 3-position of the formula (I) include
(5,6-cyclopenteno-1-methylpyridinium-2-yl)thiomethyl,
(2,3-cyclopenteno-1-methylpyridinium-4-yl)thiomethyl,
(5,6-cyclopenteno-1-methylpyridinium-3-yl)thiomethyl,
(6-methyl-2,3-cyclopenteno-1-methylpyridinium-4-yl)thiomethyl,
(5,6-cyclopenteno-1-allylpyridinium-2-yl)thiomethyl,
(2,3-cyclopenteno-1-allylpyridinium-4-yl)thiomethyl,
(5,6-cyclopenteno-1-ethylpyridinium-2-yl)thiomethyl,
(2,3-cyclopenteno-1-ethylpyridinium-4-yl)thiomethyl,
(6-methyl-2,3-cyclopenteno-1-ethylpyridinium-4-yl)thiomethyl,
(6-methyl-2,3-cyclopenteno-1-allylpyridinium-4-yl)thiomethyl,
(5-methyl-2,3-cyclopenteno-1-methylpyridinium-4-yl)thiomethyl,
(5-methyl-2,3-cyclopenteno-1-allylpyridinium-4-yl)thiomethyl,
(5,6-cyclohexeno-1-methylpyridinium-2-yl)thiomethyl,
(2,3-cyclohexeno-1-methylpyridinium-4-yl)thiomethyl,
(5,6-cyclohexeno-1-methylpyridinium-3-yl)thiomethyl,
(5,6-cyclohexeno-1-allylpyridinium-2-yl)thiomethyl,
(2,3-cyclohexeno-1-allylpyridinium-4-yl)thiomethyl,
(2,3-cyclohexeno-1-ethylpyridinium-4-yl)thiomethyl,
(6-methyl-2,3-cyclohexeno-1-methylpyridinium-4-yl)thiomethyl,
[2,3-cyclopenteno-1-(2-dimethylaminoethyl)pyridinium-4-yl]thiomethyl,
[2,3-cyclopenteno-1-(2-hydroxyethyl)pyridinium-4-yl]thiomethyl,
(2,3-cyclopenteno-1-methoxymethylpyridinium-4-yl)thiomethyl,
(2,3-cyclopenteno-1-carboxymethylpyridinium-4-yl)thiomethyl,
(2,3-cyclopenteno-1-carbamoylmethylpyridinium-4-yl)thiomethyl,
(2,3-cyclopenteno-2-carboxyethylpyridinium-4-yl)thiomethyl,
(2,3-cyclopenteno-1-carboxyethylpyridinium-4-yl)thiomethyl,
(2,3-cyclopenteno-1-cyanomethylpyridinium-4-yl)thiomethyl,
(2,3-cycolpenteno-1-sulfomethylpyridinium-4-yl)thiomethyl,
(2,3-cyclopenteno-1-sulfamoylmethylpyridinium-4-yl)thiomethyl,
[2,3-cyclopenteno-1-(2-sulfoethyl)pyridinium-4-yl]thiomethyl,
(2,3-cyclopenteno-1-methylthiomethylpyridinium-4-yl)thiomethyl,
(2,3-cyclopenteno-1-acetamidosulfonylmethylpyridinium-4-yl)thiomethyl,
[2,3-cyclopenteno-1-(methanesulfonylaminocarbonylmethyl)pyridinium-4-yl]thiomethyl,
(2,3-cyclopentenopyridine-N-oxide-4-yl)thiomethyl,
(2,3-cyclohexeno-1-carboxymethylpyridinium-4-yl)thiomethyl,
(2,3-cyclohexeno-1-sulfomethylpyridinium-4-yl)thiomethyl,
(3,4-cyclopenteno-1-carboxymethylpyridinium-2-yl)thiomethyl,
(3,4-cyclopenteno-1-sulfomethylpyridinium-2-yl)thiomethyl,
(3,4-cyclopenteno-1-methylpyridinium-2-yl)thiomethyl,
[2,3-cyclopenteno-1-(2,2,2-trifluoroethyl)pyridinium-4-yl]thiomethyl,
(2,3-cyclopenteno-1-cyclopropylpyridinium-4-yl)thiomethyl,
(1-carboxymethylpyridinium-4-yl)thiomethyl,
[1-(1-carboxyethyl)pyridinium-4-yl]thiomethyl,
(1-carboxymethylpyridinium-2-yl)thiomethyl,
[1-(1-carboxyethyl)pyridinium-2-yl]thiomethyl,
[1-(2,2,2-trifluoroethyl)pyridinium-4-yl]thiomethyl,
(1-cyclopropylpyridinium-4-yl)thiomethyl,
(1-cyclopropylpyridinium-2-yl)thiomethyl,
(1-cyclopropylpyridinium-3-yl)thiomethyl,
(1-methylpyridinium-4-yl)thiomethyl,
(1-methylpyridinium-2-yl)thiomethyl,
(1-methylpyridinium-3-yl)thiomethyl,
(1-allylpyridinium-4-yl)thiomethyl,
(1-allylpyridinium-2-yl)thiomethyl,
(1-allylpyridinium-3-yl)thiomethyl etc.

The compounds of the formula (I) of this invention exhibit strong antibacterial activity against Gram positive organisms as well as Gram negative organisms including opportunistic pathogens and thus are clinically useful.

The pharmacologically acceptable salts of the compounds of the formula (I) include medically acceptable salts, in particular, conventional non-toxic salts, and example of such salts include salts with inorganic bases, for examples, alkali metal salts such as sodium salts, potassium salts etc., alkaline earth metal salts such as calcium salts, magnesium salts etc., ammonium salts, salts with organic bases, for example, organic amine salts such as triethylamine salts, pyridine salts, ethanolamine salts, triethanolamine salts, dicyclohexylamine salts etc., and basic amino acid salts such as lysine salts, arginine salts etc.

The compounds of the formula (I) are syn-isomers, and where an asymmetric carbon is present in the 7-position side-chain, the presence of both D-form and L-form is possible, and this invention covers both of these forms and also the DL-form.

Specific examples of the compounds of this invention are given below. But it should be noted that this invention is not limited to the following description.
(6R,7R)-7-[(Z)-2-(2-aminothiazol-4-yl)-2-methoxyiminoacetamido]-3-[(5,6-cyclopenteno-1-methylpyridinium-2-yl)thiomethyl]-ceph-3-em-4-carboxylate,
(6R,7R)-7-[(Z)-2-(2-aminothiazol-4-yl)-2-carboxymethoxyiminoacetamido]-3-[(5,6-cyclopenteno-1-methylpyridinium-2-yl)thiomethyl]-ceph-3-em-4-carboxylate,
(6R,7R)-7-[(Z)-2-(2-aminothiazol-4-yl)-2-(1-methyl-1-carboxy)ethoxyiminoacetamido]-3-[(5,6-cyclopenteno-1-methylpyridinium-2-yl)thiomethyl]-ceph-3-em-4-carboxylate,
(6R,7R)-7-[(Z)-2-(2-aminothiazol-4-yl)-2-(2D-2-amino-2-carboxy)ethoxyiminoacetamido]-3-[(5,6-cyclopenteno-1-methylpyridinium-2-yl)thiomethyl]-ceph-3-em-4-carboxylate, (6R,7R)-7-[(Z)-2-(2-aminothiazol-4-yl)-2-(3DL-3-amino-3-carboxy)propioxyiminoacetamido]-3-[(5,6-cyclopenteno-1-methylpyridinium-2-yl)thiomethyl]-ceph-3-em-4-carboxylate, (6R,7R)-7-[(Z)-2-(2-aminothiazol-4-yl)-2-methoxyiminoacetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-carboxymethoxyiminoacetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-(1-methyl-1-carboxy)ethoxyiminoacetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-(2D-2-amino-2-carboxy)ethoxyiminoacetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-(3DL-3-amino-3-carboxy)propioxyiminoacetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-ethoxyiminoacetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-methoxyiminoacetamido]-3-[(2,3-cyclopenteno-1-allylpyridinium-4-yl)thiomethyl]-ceph-3-em-4-carboxylate, (6R,7R)-7-[(Z)-2-(2-aminothiazol-4-yl)-2-carboxymethoxyiminoacetamido]-3-[(2,3-cyclopenteno-1-allylpyridinium-4-yl)thiomethyl]-ceph-3-em-4-carboxylate, (6R,7R)-7-[(Z)-2-(2-aminothiazol-4-yl)-2-(1-methyl-1-carboxy)ethoxyiminoacetamido]-3-[(2,3-cyclopenteno-1-allylpyridinium-4-yl)thiomethyl]-ceph-3-em-4-carboxylate, (6R,7R)-7-[(Z)-2-(2-aminothiazol-4-yl)-2-(2D-2-amino-2-carboxy)ethoxyiminoacetamido]-[(2,3-cyclopenteno-1-allylpyridinium-4-yl)thiomethyl]-ceph-3-em-4-carboxylate, (6R,7R)-7-[(Z)-2-(2-aminothiazol-4-yl)-2-ethoxyiminoacetamido]-3-[(2,3-cyclopenteno-1-allylpyridinium-4-yl)thiomethyl]-ceph-3-em-4-carboxylate, (6R,7R)-7-[(Z)-2-(2-aminothiazol-4-yl)-2-methoxyiminoacetamido]-3-[(6-methyl-2,3-cyclopenteno-1-methylpyridinium-4-yl)thiomethyl]-ceph-3-em-4-carboxylate, (6R,7R)-7-[(Z)-2-(2-aminothiazol-4-yl)-2-carboxymethoxyiminoacetamido]-3-[(6-methyl-2,3-cyclopenteno-1-methylpyridinium-4-yl)thiomethyl]-ceph-3-em-4-carboxylate, (6R,7R)-7-[(Z)-2-(2-aminothiazol-4-yl)-2-(1-methyl-1-carboxy)ethoxyiminoacetamido]-3-[(6-methyl-2,3-cyclopenteno-1-methylpyridinium-4-yl)thiomethyl]-ceph-3-em-4-carboxylate, (6R,7R)-7-[(Z)-2-(2-aminothiazol-4-yl)-2-(2D-2-amino-2-carboxy)ethoxyiminoacetamido]-3-[(6-methyl-2,3-cyclopenteno-1-methylpyridinium-4-yl)thiomethyl]-ceph-3-em-4-carboxylate, (6R,7R)-7-[(Z)-2-(2-aminothiazol-4-yl)-2-ethoxyiminoacetamido]-3-[(6-methyl-2,3-cyclopenteno-1-methylpyridinium-4-yl)thiomethyl]-ceph-3-em-4-carboxylate, (6R,7R)-7-[(Z)-2-(2-aminothiazol-4-yl)-2-methoxyiminoacetamido]-3-[(6-methyl-2,3-cyclopenteno-1-ethylpyridinium-4-yl)thiomethyl]-ceph-3-em-4-carboxylate, (6R,7R)-7-[(Z)-2-(2-aminothiazol-4-yl)-2-(1-methyl-1-carboxy)ethoxyiminoacetamido]-3-[(6-methyl-2,3-cyclopenteno-1-ethylpyridinium-4-yl)thiomethyl]-ceph-3-em-4-carboxylate, (6R,7R)-7-[(Z)-2-(2-aminothiazol-4-yl)-2-methoxyiminoacetamido]-3-[(6-methyl-2,3-cyclopenteno-1-allylpyridinium-4-yl)thiomethyl]-ceph-3-em-4-carboxylate, (6R,7R)-7-[(Z)-2-(2-aminothiazol-4-yl)-2-(1-methyl-1-carboxy)ethoxyiminoacetamido]-3-[(6-methyl-2,3-cyclopenteno-1-allylpyridinium-4-yl)thiomethyl]-ceph-3-em-4-carboxylate, (6R,7R)-7-[(Z)-2-(2-aminothiazol-4-yl)-2-carboxymethoxyiminoacetamido]-3-[(6-methyl-2,3-cyclopenteno-1-allylpyridinium-4-yl)thiomethyl]-ceph-3-em-4-carboxylate, (6R,7R)-7-[(Z)-2-(2-aminothiazol-4-yl)-2-(2D-2-amino-2-carboxy)ethoxyiminoacetamido]-3-[(6-methyl-2,3-cyclopenteno-1-allylpyridinium-4-yl)thiomethyl]-ceph-3-em-4-carboxylate, (6R,7R)-7-[(Z)-2-(2-aminothiazol-4-yl)-2-methoxyiminoacetamido]-3-[(5,6-cyclohexeno-1-methylpyridinium-2-yl)thiomethyl]-ceph-3-em-4-carboxylate, (6R,7R)-7-[(Z)-2-(2-aminothiazol-4-yl)-2-carboxymethoxyiminoacetamido]-3-[(5,6-cyclohexeno-1-methylpyridinium-2-yl)thiomethyl]-ceph-3-em-4-carboxylate, (6R,7R)-7-[(Z)-2-(2-aminothiazol-4-yl)-2-(1-methyl-1-carboxy)ethoxyiminoacetamido]-3-[(5,6-cyclohexeno-1-methylpyridinium-2-yl)thiomethyl]-ceph-3-em-4-carboxylate, (6R,7R)-7-[(Z)-2-(2-aminothiazol-4-yl)-2-(2D-2-amino-2-carboxy)ethoxyiminoacetamido]-3-[(5,6-cyclohexeno-1-methylpyridinium-2-yl)thiomethyl]-ceph-3-em-4-carboxylate, (6R,7R)-7-[(Z)-2-(2-aminothiazol-4-yl)-2-methoxyiminoacetamido]-3-[(5-methyl-2,3-cyclopenteno-1-methylpyridinium-4-yl)thiomethyl]-ceph-3-em-4-carboxylate, (6R,7R)-7-[(Z)-2-(2-aminothiazol-4-yl)-2-methoxyiminoacetamido]-3-[(5-methyl-2,3-cyclopenteno-1-allylpyridinium-4-yl)thiomethyl]-ceph-3-em-4-carboxylate, (6R,7R)-7-[(Z)-2-(2-aminothiazol-4-yl)-2-methoxyiminoacetamido]-3-[(2,3-cyclopenteno-1-allylpyridinium-2-yl)thiomethyl]-ceph-3-em-4-carboxylate, (6R,7R)-7-[(Z)-2-(2-aminothiazol-4-yl)-2-methoxyiminoacetamido]-3-[(2,3-cyclohexeno-1-methylpyridinium-4-yl)thiomethyl]-ceph-3-em-4-carboxylate, (6R,7R)-7-[(Z)-2-(2-aminothiazol-4yl)-2-carboxymethoxyiminoacetamido]-3-[(2,3-cyclohexeno-1-methylpyridinium-4-yl)thiomethyl]-ceph-3-em-4-carboxylate, (6R,7R)-7-[(Z)-2-(2-aminothiazol-4-yl)-2-(1-methyl-1-carboxy)ethoxyiminoacetamido]-3-[(2,3-cyclohexeno-1-methylpyridinium-4-yl)thiomethyl]-ceph-3-em-4-carboxylate, (6R,7R)-7-[(Z)-2-(2-aminothiazol-4-yl)-2-(2D-2-amino-2-carboxy)ethoxyiminoacetamido]-3-[(2,3-cyclohexeno-1-methylpyridinium-4yl)thiomethyl]-ceph-3-em-4-carboxylate, (6R,7R)-7-[(Z)-2-(2-aminothiazol-4-yl)-2-ethox-
yiminoacetamido]-3-[(2,3-cyclohexeno-1-methyl-
pyridinium-4-yl)thiomethyl]-ceph-3-em-4-carboxy-
late, (6R,7R)-7-[(Z)-2-(2-aminothiazol-4-yl)-2-methox-
yiminoacetamido]-3-[(2,3-cyclohexeno-1-ethyl-
pyridinium-4-yl)thiomethyl]-ceph-3-em-4-carboxy-
late, (6R,7R)-7-[(Z)-2-(2-aminothiazol-4-yl)-2-(1-methyl-1-
carboxy)ethoxyiminoacetamido]-3-[(2,3-cyclohex-
eno-1-ethylpyridinium-4-yl)thiomethyl]-ceph-3-em-
4-carboxylate, (6R,7R)-7-[(Z)-2-(2-aminothiazol-4yl)-2-methox-
yiminoacetamido]-3-[(2,3-cyclohexeno-1-allyl-
pyridinium-4-yl)thiomethyl]-ceph-3-em-4-carboxy-
late, (6R,7R)-7-[(Z)-2-(2-aminothiazol-4-yl)-2-carboxyme-
thoxyiminoacetamido]-3-[(2,3-cyclohexeno-1-allyl-
pyridinium-4-yl)thiomethyl]-ceph-3-em-4-carboxy-
late, (6R,7R)-7-[(Z)-2-(2-aminothiazol-4-yl)-2-(1-methyl-1-
carboxy)ethoxyiminoacetamido]-3-[(2,3-cyclohex-
eno-1-allylpyridinium-4-yl)thiomethyl]-ceph-3-em-4-
carboxylate, (6R,7R)-7-[(Z)-2-(2-aminothiazol-4-yl)-2-(2D-2-amino-
carboxy)ethoxyiminoacetamido]-3-[(2,3-cyclohex-
eno-1-allylpyridinium-4-yl)thiomethyl]-ceph-3-em-4-
carboxylate, (6R,7R)-7-[(Z)-2-(2-aminothiazol-4-yl)-2-methox-
yiminoacetamido]-3-[(6-methyl-2,3-cyclohexeno-1-
methylpyridinium-4-yl)thiomethyl]-ceph-3-em-4-car-
boxylate, (6R,7R)-7-[(Z)-2-(2-aminothiazol-4-yl)-2-carboxyme-
thoxyiminoacetamido]-3-[(6-methyl-2,3-cyclohex-
eno-1-methylpyridinium-4-yl)thiomethyl]-ceph-3-
em-4-carboxylate, (6R,7R)-7-[(Z)-2-(2-aminothiazol-4-yl)-2-(1-methyl-1-
carboxy)ethoxyiminoacetamido]-3-[(6-methyl-2,3-
cyclohexeno-1-methylpyrinium-4-yl)thiomethyl]-
ceph-3-em-4-carboxylate, (6R,7R)-7-[(Z)-2-(2-aminothiazol-4-yl)-2-(2D-2-amino-
2-carboxy)ethoxyiminoacetamido]-3-[(6-methyl-2,3-
cyclohexeno-1-methylpyridinium-4-yl)thiomethyl]-
ceph-3-em-4-carboxylate, (6R,7R)-7-[(Z)-2-(2-aminothiazol-4-yl)-2-methox-
yiminoacetamido]-3-[(5,6-cyclohexeno-1-methyl-
pyridinium-3-yl)thiomethyl]-ceph-3-em-4-carboxy-
late, (6R,7R)-7-[(Z)-2-(2-aminothiazol-4-yl)-2-carboxyme-
thoxyiminoacetamido]-3-[(1-cyclopropylpyridinium-
4-yl)thiomethyl]-ceph-3-em-4-carboxylate, (6R,7R)-7[(Z)-2-(2-aminothiazol-4yl)-2-(carboxyme-
thoxyimino)acetamido]-3-[(2,3-cyclopenteno-1-
cyclopropylpyridinium-4-yl)thiomethyl]-ceph-3-em-
4-carboxylate, (6R,7R)-7-[(Z)-2-(2-aminothiazol-4yl)-2-methox-
yiminoacetamido]-3-[(2,3-cyclopenteno-1-carbox-
ymethylpyridinium-4-yl)thiomethyl]-ceph-3-em-4-
carboxylate, (6R,7R)-7-[(Z)-2-(2-aminothiazol-4-yl)-2-methox-
yiminoacetamido]-3-[(2,3-cyclopenteno-1-car-
bamoylmethylpyridinium-4-yl)thiomethyl]-ceph-3-
em-4-carboxylate, (6R,7R)-7-[(Z)-2-(2-aminothiazol-4-yl)-2-methox-
yiminoacetamido]-3-[(2,3-cyclopenteno-1-(2-carbox-
yethyl)pyridinium-4-yl)thiomethyl]-ceph-3-em-4-car-
boxylate, (6R,7R)-7-[(Z)-2-(2-aminothiazol-4-yl)-2-methox-
yiminoacetamido]-3-(2,3-cyclopenteno-1-cyanome-
thylpyridinium-4-yl)thiomethyl]-ceph-3-em-4-car-
boxylate, (6R,7R)-7-[(Z)-2-(2-aminothiazol-4-yl)-2-methox-
yiminoacetamido]-3-[(2,3-cyclopenteno-1-sulfome-
thylpyridinium-4-yl)thiomethyl]-ceph-3-em-4-car-
boxylate, (6R,7R)-7-[(Z)-2-(2-aminothiazol-4-yl)-2-methox-
yiminoacetamido]-3-[(2,3-cyclopenteno-1-sulfamoyl-
methylpyridinium-4-yl)thiomethyl]-ceph-3-em-4-car-
boxylate, (6R,7R)-7-[(Z)-2-(2-aminothiazol-4-yl)-2-methox-
yiminoacetamido]-3-[(2,3-cyclopenteno-1-(2-sulfoe-
thyl)pyridinium-4-yl)thiomethyl]-ceph-3-em-4-car-
boxylate, (6R,7R)-7[(Z)-2-(2-aminothiazol-4yl)-2-methox-
yiminoacetamido]-3-[(2,3-cyclopenteno-1-methylthi-
omethylpyridinium-4yl)thiomethyl]-ceph-3-em-4-
carboxylate, (6R,7R)-7-[(Z)-2-(2-aminothiazol-4-yl)-2-methox-
yiminoacetamido]-3-[(2,3-cyclopenteno-1-(2-hydrox-
yethyl)pyridinium-4-yl)thiomethyl]-ceph-3-em-4-car-
boxylate, (6R,7R)-7-[(Z)-2-(2-aminothiazol-4-yl)-2-methox-
yiminoacetamido]-3-[(2,3-cyclopenteno-1-(2-dime-
thylaminoethyl)pyridinium-4-yl)thiomethyl]-ceph-3-
em-4-carboxylate, (6R,7R)-7[(Z)-2-(2-aminothiazol-4-yl)-2-methox-
yiminoacetamido]-3-[(2,3-cyclopenteno-1-
acetamidosulfonylmethylpyridinium-4-yl)thiome-
thyl]-ceph-3-em-4-carboxylate, (6R,7R)-7-[(Z)-2-(2-aminothiazol-4-yl)-2-methox-
yiminoacetamido]-3-[(2,3-cyclopenteno-1-
methanesulfonylaminocarbonylmethylpyridinium-4-
yl)thiomethyl]-ceph-3-em-4-carboxylate, (6R,7R)-7-[(Z)-2-(2-aminothiazol-4-yl)-2-ethox-
yiminoacetamido]-3-[(2,3-cyclopenteno-1-carbox-
ymethylpyridinium-4-yl)thiomethyl]-ceph-3-em-4-
carboxylate, (6R,7R)-7-[(Z)-2-(2-aminothiazol-4-yl)-2-ethox-
yiminoacetamido]-3-[(2,3-cyclopenteno-1-car-
bamoylmethylpyridinium-4-yl)thiomethyl]-ceph-3-
em-4-carboxylate, (6R,7R)-7-[(Z)-2-(2-aminothiazol-4-yl)-2-ethox-
yiminoacetamido]-3-[[2,3-cyclopenteno-1-(2-carbox-
yethyl)pyridinium-4-yl]thiomethyl]-ceph-3-em-4-car-
boxylate, (6R,7R)-7-[(Z)-2-(2-aminothiazol-4-yl)-2-ethox-
yiminoacetamido]-3-[(2,3-cyclopenteno-1-sulfome-
thylpyridinium-4-yl)thiomethyl]-ceph-3-em-4-car-
boxylate, (6R,7R)-7-[(Z)-2-(2-aminothiazol-4-yl)-2-ethox-
yiminoacetamido]-3-[(2,3-cyclopenteno-1-sulfamoyl-
methylpyridinium-4-yl)thiomethyl]-ceph-3-em-4-car-
boxylate, (6R,7R)-7-[(Z)-2-(2-aminothiazol-4-yl)-2-ethox-
yiminoacetamido]-3-[(2,3-cyclopenteno-1-(2-sulfoe-
thyl)pyridinium-4-yl)thiomethyl]-ceph-3-em-4-car-
boxylate, (6R,7R)-7-[(Z)-2-(2-aminothiazol-4-yl)-2-(2-fluoroe-
thoxyimino)acetamido]-3-[(2,3-cyclopenteno-1-
methylpyridinium-4-yl)thiomethyl]-ceph-3-em-4-car-
boxylate, (6R,7R)-7-[(Z)-2-(2-aminothiazol-4-yl)-2-(2-fluoroe-
thoxyimino)acetamido]-3-[(2,3-cyclopenteno-1-car-
boxymethylpyridinium-4-yl)thiomethyl]-ceph-3-em-
4-carboxylate, (6R,7R)-7-[(Z)-2-(2-aminothiazol-4-yl)-2-(2-fluoroethoxyimino)acetamido]-3-[(2,3-cyclopenteno-1-carbamoylmethylpyridinium-4-yl)thiomethyl]-ceph-3-em-4-carboxylate, (6R,7R)-7-[(Z)-2-(2-aminothiazol-4-yl)-2-(2-fluoroethoxyimino)acetamido]-3-[(2,3-cyclopenteno-1-(2-carboxyethyl)pyridinium-4-yl)thiomethyl]-ceph-3-em-4-carboxylate, (6R,7R)-7-[(Z)-2-(2-aminothiazol-4-yl)-2-(2-fluoroethoxyimino)acetamido]-3-[(2,3-cyclopenteno-1-sulfomethylpyridinium-4-yl)thiomethyl]-ceph-3-em-4-carboxylate, (6R,7R)-7-[(Z)-2-(2-aminothiazol-4-yl)-2-(2-fluoroethoxyimino)acetamido]-3-[(2,3-cyclopenteno-1-sulfamoylmethylpyridinium-4-yl)thiomethyl]-ceph-3-em-4-carboxylate, (6R,7R)-7-[(Z)-2-(2-aminothiazol-4-yl)-2-(2-fluoroethoxyimino)acetamido]-3-[(2,3-cyclopenteno-1-(2-sulfoethyl)pyridinium-4-yl)thiomethyl]-ceph-3-em-4-carboxylate, (6R,7R)-7-[(Z)-2-(2-aminothiazol-4-yl)-2-2,2,2-trifluoroethoxyimino)acetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-(2,2,2-trifluoroethoxyimino)acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-(2,2,2-trifluoroethoxyimino)acetamido]-3-[(2,3-cyclopenteno-1-sulfomethylpyridinium-4-yl)thiomethyl]-ceph-3-em-4-carboxylate, (6R,7R)-7-[(Z)-2-(2-aminothiazol-4-yl)-2-(cyclopropylmethoxyimino)acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-(cyclopropylmethoxyimino)acetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-(cyclopropylmethoxyimino)acetamido]-3-[(2,3-cyclopenteno-1-carbamoylmethylpyridinium-4-yl)thiomethyl]-ceph-3-em-4-carboxylate, (6R,7R)-7-[(Z)-2-(2-aminothiazol-4-yl)-2-(cyclopropylmethoxyimino)acetamido]-3-[(2,3-cyclopenteno-1-sulfomethylpyridinium-4-yl)thiomethyl]-ceph-3-em-4-carboxylate, (6R,7R)-7-[(Z)-2-(2-aminothiazol-4-yl)-2-(cyclopropylmethoxyimino)acetamido]-3-[(2,3-cyclopenteno-1-(2-sulfoethyl)pyridinium-4-yl)thiomethyl]-ceph-3-em-4-carboxylate, (6R,7R)-7-[(Z)-2-(2-aminothiazol-4-yl)-2-(cyclopropylmethoxyimino)acetamido]-3-[(2,3-cyclopenteno-1-sulfamoylmethylpyridinium-4-yl)thiomethyl]-ceph-3-em-4-carboxylate, (6R,7R)-7-[(Z)-2-(2-aminothiazol-4-yl)-2-(carboxymethoxyimino)acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-(carboxymethoxyimino)acetamido]-3-[(2,3-cyclopenteno-1-carbamoylmethylpyridinium-4-yl)thiomethyl]-ceph-3-em-4-carboxylate, (6R,7R)-7-[(Z)-2-(2-aminothiazol-4-yl)-2-(carboxymethoxyimino)acetamido]-3-[(2,3-cyclopenteno-1-sulfomethylpyridinium-4-yl)thiomethyl]-ceph-3-em-4-carboxylate, (6R,7R)-7-[(Z)-2-(2-aminothiazol-4-yl)-2-(carboxymethoxyimino)acetamido]-3-[(2,3-cyclopenteno-1-(2-sulfoethyl)pyridinium-4-yl)thiomethyl]-ceph-3em-4-carboxylate, (6R,7R)-7-[(Z)-2-(2-aminothiazol-4-yl)-2-(carbamoylmethoxyimino)acetamido]-3-[(2,3-cyclopenteno-1-methylpyridinium-4-yl)thiomethyl]-ceph-3-em-4-carboxylate, (6R,7R)-7-[(Z)-2-(2-amoinothiazol-4-yl)-2-(carbamoylmethoxyimino)acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-(carbamoylmethoxyimino)acetamido]-3-[(2,3-cyclopenteno-1-sulfomethylpyridinium-4-yl)thiomethyl]-ceph-3-em-4-carboxylate, (6R,7R)-7-[(Z)-2-(2-aminothiazol-4-yl)-2-(carbamoylmethoxyimino)acetamido]-3-[(2,3-cyclopenteno-1-(2-sulfoethyl)pyridinium-4-yl)thiomethyl]-ceph-3-em-4-carboxylate, (6R,7R)-7-[(Z)-2-(2-aminothiazol-4-yl)-2-(carbamoylmethoxyimino)acetamido]-3-[(2,3-cyclopenteno-1-carbamoylmethylpyridinium-4-yl)thiomethyl]-ceph-3-em-4-carboxylate, (6R,7R)-7-[(Z)-2-(2-aminothiazol-4-yl)-2-(carbamoylmethoxyimino)acetamido]-3-[(2,3-cyclopenteno-1-sulfamoylmethylpyridinium-4-yl)thiomethyl]-ceph-3-em-4-carboxylate, (6R,7R)-7-[(Z)-2-(2-aminothiazol-4-yl)-2-(1-methyl-1-carboxyethoxyimino)acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-(1-methyl-1-carboxyethoxyimino)acetamido]-3-[(2,3-cyclopenteno-1-sulfomethylpyridinium-4-yl)thiomethyl]-ceph-3-em-4-carboxylate, (6R,7R)-7-[(Z)-2-(2-aminothiazol-4-yl)-2-methoxyiminoacetamido]-3-[(2,3-cyclohexeno-1-carboxymethylpyridinium-4-yl)thiomethyl]-ceph-3-em-4-carboxylate, (6R,7R)-7-[(Z)-2-(2-aminothiazol-4-yl)-2-methoxyiminoacetamido]-3-[(2,3-cyclohexeno-1-sulfomethylpyridinium-4-yl)thiomethyl]-ceph-3-em-4-carboxylate, (6R,7R)-7-[(Z)-2-(2-aminothiazol-4-yl)-2-ethoxyiminoacetamido]-3-[(2,3-cyclohexeno-1-carboxymethylpyridinium-4-yl)thiomethyl]-ceph-3-em-4-carboxylate, (6R,7R)-7-[(Z)-2-(2-aminothiazol-4-yl)-2-ethoxyiminoacetamido]-3-[(2,3-cyclohexeno-1-sulfomethylpyridinium-4-yl)thiomethyl]-ceph-3-em-4-carboxylate, (6R,7R)-7-[(Z)-2-(2-aminothiazol-4-yl)-2-(2-fluoroethoxyimino)acetamido]-3-[(2,3-cyclohexeno-1-carboxymethylpyridinium-4-yl)thiomethyl]-ceph-3-em-4-carboxylate, (6R,7R)-7-[(Z)-2-(2-aminothiazol-4-yl)-2-(2-fluoroethoxyimino)acetamido]-3-[(2,3-cyclohexeno-1-sulfomethylpyridinium-4-yl)thiomethyl]-ceph-3-em-4-carboxylate, (6R,7R)-7-[(Z)-2-(2-aminothiazol-4-yl)-2-(cyclopropylmethoxyimino)acetamido]-3-[(2,3-cyclohexeno-1-carboxymethylpyridinium-4-yl)thiomethyl]-ceph-3-em-4-carboxylate, (6R,7R)-7-[(Z)-2-(2-aminothiazol-4yl)-2-(cyclopropylmethoxyimino)acetamido]-3-[(2,3-cyclohexeno-1-sulfomethylpyridinium-4-yl)thiomethyl]-ceph-3-em-4-carboxylate, (6R,7R)-7-[(Z)-2-(2-aminothiazol-4-yl)-2-methoxyiminoacetamido]-3-[(3,4-cyclopenteno-1-methylpyridinium-2-yl)thiomethyl]-ceph-3-em-4-carboxylate, (6R,7R)-7-[(Z)-2-(2-aminothiazol-4-yl)-2-methoxyiminoacetamido]-3-[(3,4-cyclopenteno-1-carboxymethylpyridinium-2-yl)thiomethyl]-ceph-3-em-4-carboxylate, (6R,7R)-7-[(Z)-2-(2-aminothiazol-4-yl)-2-methoxyiminoacetamido]-3-[(3,4-cyclopenteno-1-sulfomethylpyridinium-2-yl)thiomethyl]-ceph-3-em-4-carboxylate, (6R,7R)-7-[(Z)-2-(2-aminothiazol-4-yl)-2-ethoxyiminoacetamido]-3-[(3,4-cyclopenteno-1-carboxymethylpyridinium-2-yl)thiomethyl]-ceph-3-em-4-carboxylate, (6R,7R)-7-[(Z)-2-(2-aminothiazol-4-yl)-2-ethoxyiminoacetamido]-3-[(3,4-cyclopenteno-1-sulfomethylpyridinium-2-yl)thiomethyl]-ceph-3-em-4-carboxylate, (6R,7R)-7-[(Z)-2-(2-amoinothiazol-4-yl)-2-[(pyridin-2-yl)methoxyimino]acetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-[(pyridin-2-yl)methoxyimino]acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-[(imidazol-4-yl)methoxyimino]acetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-[(5-methylimidazol-4-yl)methoxyimino]acetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-[(2-methylimidazol-4-yl)methoxyimino]acetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-[(imidazol-4-yl)methoxyimino]acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-[(imidazol-4-yl)methoxyimino]acetamido]-3-[(2,3-cyclopenteno-1-sulfomethylpyridinium-4-yl)thiomethyl]-ceph-3-em-4-carboxylate, (6R,7R)-7-[(Z)-2-(2-aminothiazol-4-yl)-2-[(2-aminothiazol-4-yl)methoxyimino]acetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-[(2-aminothiazol-4-yl)methoxyimino]acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-[(1,2,3-triazol-4-yl)methoxyimino]acetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-[(1,2,3-triazol-4-yl)methoxyimino]acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-[(1,2,3-triazol-4-yl)methoxyimino]acetamido]-3-[(1-methylpyridinium-4-yl)thiomethyl]-ceph-3-em-4-carboxylate, (6R,7R)-7[(Z)-2-(2-aminothiazol-4-yl)-2-[(1,2,4-triazol-3-yl)methoxyimino]acetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-[(1,2,4-triazol-3-yl)methoxyimino]acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-[(1,2,4-triazol-3-yl)methoxyimino]acetamido]-3-[(1-methylpyridinium-4-yl)thiomethyl]-ceph-3-em-4-carboxylate, (6R,7R)-7-[(Z)-2-(2-aminothiazol-4-yl)-2-[(imidazol-4-yl)methoxyimino]acetamido]-3-[(1-methylpyridinium-4-yl)thiomethyl]-ceph-3-em-4-carboxylate, (6R,7R)-7-[(Z)-2-(2-aminothiazol-4-yl)-2-[(2-aminothiazol-4-yl)methoxyimino]acetamido]-3-[(1-methylpyridinium-4-yl)thiomethyl]-ceph-3-em-4-carboxylate, (6R,7R)-7-[(Z)-2-(2-aminothiazol-4-yl)-2-(N-methylcarbamoylmethoxyimino)acetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-(N-methylcarbamoylmethoxyimino)acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-(2D-2-amino-2-carboxyethoxyimino)acetamido]-3-[(1-methylpyridinium-4-yl)thiomethyl]-ceph-3-em-4-carboxylate, (6R,7R)-7-[(Z)-2-(2-aminothiazol-4-yl)-2-(2D-2-amino-2-carboxyethoxyimino)acetamido]-3-[(1-allylpyridinium-2-yl)thiomethyl]-ceph-3-em-4-carboxylate, (6R,7R)-7-[(Z)-2-(2-aminothiazol-4-yl)-2-(2D-2-amino-2-carboxyethoxyimino)acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-(2D-2-amino-2-carboxyethoxyimino)acetamido]-3-[(2,3-cyclopenteno-1-sulfomethylpyridinium-4-yl)thiomethyl]-ceph-3-em-4-carboxylate, (6R,7R)-7-[(Z)-2-(2-aminothiazol-4-yl)-2-(3DL-3-amino-3-carboxypropyloxyimino)acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-(3DL-3-amino-3-carboxypropyloxyimino)acetamido]-3-[(2,3-cyclopenteno-1-sulfomethylpyridinium-4-yl)thiomethyl]-ceph-3-em-4-carboxylate, (6R,7R)-7-[(Z)-2-(2-aminothiazol-4-yl)-2-(2D-2-amino-2-carboxyethoxyimino)acetamido]-3-[(2,3-cyclopenteno-1-carbamoylmethylpyridinium-4-yl)thiomethyl]-ceph-3-em-4-carboxylate, (6R,7R)-7-[(Z)-2-(2-aminothiazol-4-yl)-2-(2D-2-amino-2-carboxyethoxyimino)acetamido]-3-[(2,3-cyclopenteno-1-sulfamoylmethylpyridinium-4-yl)thiomethyl]-ceph-3-em-4-carboxylate, (6R,7R)-7-[(Z)-2-(2-aminothiazol-4-yl)-2-(methoxyimino)acetamido]-3-[(1-carboxymethylpyridinium-4-yl)thiomethyl]-ceph-3-em-4-carboxylate, (6R,7R)-7-[(Z)-2-(2-aminothiazol-4-yl)-2-(ethoxyimino)acetamido]-3-[(1-carboxymethylpyridinium-4-yl)thiomethyl]-ceph-3-em-4-carboxylate, (6R,7R)-7-[(Z)-2-(2-aminothiazol-4-yl)-2-(carboxymethoxyimino)acetamido]-3-[(1-carboxymethylpyridinium-4-yl)thiomethyl]-ceph-3-em-4-carboxylate, (6R,7R)-7-[(Z)-2-(2-aminothiazol-4-yl)-2-(allyloxyimino)acetamido]-3-[(1-carboxymethylpyridinium-4-yl)thiomethyl]-ceph-3-em-4-carboxylate, (6R,7R)-7-[(Z)-2-(2-aminothiazol-4-yl)-2-(ethoxyimino)acetamido]-3-[[1-(1-carboxy)ethylpyridinium-4-yl]thiomethyl]-ceph-3-em-4-carboxylate, (6R,7R)-7-[(Z)-2-(2-aminothiazol-4-yl)-2-(ethoxyimino)acetamido]-3-[[1-(α-carboxy)benzylpyridinium-4-yl]thiomethyl]-ceph-3-em-4-carboxylate, (6R,7R)-7-[(Z)-2-(2-aminothiazol-4-yl)-2-(ethoxyimino)acetamido]-3-[(1-carboxymethylpyrimidinium-2-yl)thiomethyl]-ceph-3-em-4-carboxylate, (6R,7R)-7-[(Z)-2-(2-aminothiazol-4-yl)-2-methoxyiminoacetamido]-3-[(2,3-cyclopenteno-1-cyclopropylpyridinium-4-yl)thiomethyl]-ceph-3-em-4-carboxylate, (6R,7R)-7-[(Z)-2-(2-aminothiazol-4-yl)-2-methoxyiminoacetamido]-3-[(1-cyclopropylpyridinium-4-yl)thiomethyl]-ceph-3-em-4-carboxylate, (6R,7R)-7-[(Z)-2-(2-aminothiazol-4-yl)-2-methoxyiminoacetamido]-3-[(2,3-cyclopenteno-1-(2,2,2-trifluoroethyl)pyridinium-4-yl)thiomethyl]-ceph-3-em-4-carboxylate, (6R,7R)-7-[(Z)-2-(2-aminothiazol-4-yl)-2-(difluoromethoxyimino)acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-(cyclopropylmethoxyimino)acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-(difluoromethoxyimino)acetamido]-3-[(2,3-cyclopenteno-1-methylpyridinium-4-yl)thiomethyl]-ceph-3-em-4-carboxylate, (6R,7R)-7-[(Z)-2-(2-aminothiazol-4-yl)-2-(vinyloxyimino)acetamido]-3-[(2,3-cyclopenteno-1-methylpyridinium-4-yl)thiomethyl]-ceph-3-em-4-carboxylate, (6R,7R)-4-[(Z)-2-(2-aminothiazol-4-yl)-2-(vinyloxyimino)acetamido]-3-[(2,3-cyclopenteno-1-carboxymethylpyridinium-4-yl)thiomethyl]-ceph-3-em-4-carboxylate, (6R,7R)-7-[(Z)-2-(2-aminothiazol-4-yl)-2-(methoxyimino)acetamido]-3-[1-((2,2,2-trifluoroethyl)-pyridinium-4-yl)thiomethyl]-ceph-3-em-4-carboxylate, (6R,7R)-7-[(Z)-2-(2-aminothiazol-4-yl)-2-(ethoxyimino)acetamido]-3-[1-((2,2,2-trifluoroethyl)-pyridinium-4-yl)thiomethyl]-ceph-3-em-4-carboxylate, (6R,7R)-7-[(Z)-2-(2-aminothiazol-4-yl)-2-(carboxymethoxyimino)acetamido]-3-[1-((2,2,2-trifluoroethyl)-pyridinium-4-yl)thiomethyl]-ceph-3-em-4-carboxylate, (6R,7R)-7-[(Z)-2-(2-aminothiazol-4-yl)-2-(1-methyl-1-carboxyethoxyimino)acetamido]-3-[1-((2,2,2-trifluoroethyl)pyridinium-4-yl)thiomethyl]-ceph-3-em-4-carboxylate, (6R,7R)-7-[(Z)-2-(2-aminothiazol-4-yl)-2-(methoxyimino)acetamido]-3-[1-((2-fluoroethyl)pyridinium-4-yl)thiomethyl]-ceph-3-em-4-carboxylate.

The compounds of the general formula (I) may be produced by either Process (A) or (B) described below.

(A) Reaction of a compound of the general formula (II):

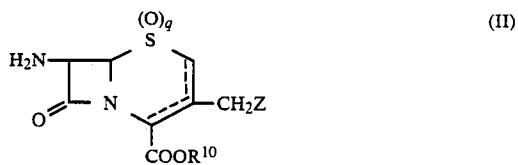

wherein (Z) is as defined above, $R^{10}$ is hydrogen or a protecting group for the carboxyl group, q is 0 or 1, and the broken line bridging the 2-, 3- and 4-positions indicates that the compound is a ceph-2-em or ceph-3-em compound, or a salt thereof or a form thereof in which the carboxyl group is protected, with a compound of the general formula (III):

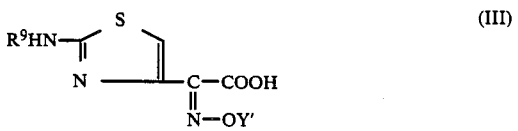

wherein
$R^9$ is a protecting group for the amino group, and
Y' is straight or branched alkyl or alkenyl chain, cycloalkanomethyl of 3–6 carbon atoms, each group being optionally substituted by halogen, or a group

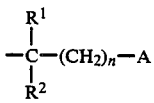

wherein n is 0 or an integer of 1–3, A is a group —$COR^{3'}$ wherein $R^{3'}$ is $OR^{11}$ wherein $R^{11}$ is a protecting group for the carboxyl group or a group

wherein $R^4$ and $R^5$, which may be the same or different, are hydrogen or alkyl of 1–5 carbon atoms, with the provision that where $R^4$ and $R^5$ are both hydrogen, either of them represents a protecting group for the amino group, a group

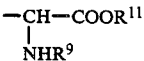

wherein $R^{11}$ is a protecting group for the carboxyl group and $R^9$ is as defined above, or a 5- or 6-membered heterocyclic group containing nitrogen and-/or sulfur, and $R^1$ and $R^2$, which may be the same or different, are hydrogen, alkyl of 1–5 carbon atoms, or $R^1$ and $R^2$ may be combined together to form cycloalkylidene of 3–5 carbon atoms, or a relative derivative of the carboxylic acid.

(B) Reaction of a compound of the general formula (IV):

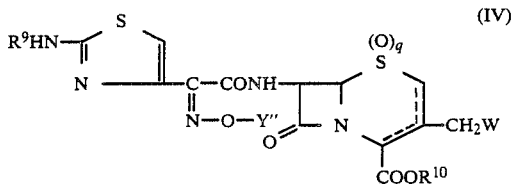

wherein W is a residue capable of being substituted by a nucleophilic reagent, Y″ is the same as Y or Y′, and $R^9$, $R^{10}$, q and the broken line are as defined above, with a compound of the general formula (V):

wherein Z is as defined above.

After either of the above Processes (A) and (B), one or more of the following steps are conducted if necessary.

(i) removal of any protecting group for the carboxyl group or the amino group;
(ii) conversion of the $\Delta^2$ isomer to the $\Delta^3$ isomer;
(iii) conversion (reduction) of the sulfoxide compound (q=1) to the sulfide compound (q=0); and
(iv) formation of a non-toxic salt.

In both Processes (A) and (B), such compounds that q is 0 and broken line represents a ceph-3-em compound are suitable for the starting materials.

The $\Delta^2$ cephalosporin ester derivatives with q=1 obtained by the process of this invention may be converted to desired $\Delta^3$ compounds by treating with a base such as triethylamine, pyridine etc.

Where a sulfoxide compound in which q is 1 is obtained, a reducing agent such as sodium dithionite etc. is used in order to convert it to the desired sulfide compound.

As the protecting groups for the amino group and the carboxyl group in the above general formula, those used for the same purpose in the field of β-lactam and peptide syntheses are appropriately employed.

Examples of the protecting group for the amino group include phthaloyl, formyl, monochloroacetyl, dichloroacetyl, trichloroacetyl, methoxycarbonyl, ethoxycarbonyl, t-butoxycarbonyl, trichloroethoxycarbonyl, benzyloxycarbonyl, p-nitrobenzyloxycarbonyl, diphenylmethyloxycarbonyl, methoxymethyloxycarbonyl, trityl, trimethylsilyl etc., while examples of the protecting group for the carboxyl group include t-butyl, t-amyl, benzyl, p-nitrobenzyl, p-methoxybenzyl, benzhydryl, phenyl, p-nitrophenyl, methoxymethyl, ethoxymethyl, benzyloxymethyl, acetoxymethyl, methylthiomethyl, trityl, trichloroethyl, trimethylsilyl, dimethylsilyl, dimethylaminoethyl etc.

The acylation reaction in Process (A) may be effected by reacting one mole of the compound (II) with 1-3 moles of a carboxylic acid reactive derivative of the compound (III).

Examples of the reactive derivative include acid halides, acid anhydrides, active amides, active esters etc. Preferred examples include acid chlorides, acid bromides, mixed acid anhydrides of e.g. acetic acid, pivalic acid, isovaleric acid, trichloroacetic acid, etc., active amides with pyrazole, imidazole, dimethylpyrazole, benztriazole etc., p-nitrophenyl esters, 2,4-dinitrophenyl esters, trichlorophenyl esters, active esters with 1-hydroxy-1H-2-pyrridone, N-hydroxysuccinimide, N-hydroxyphthalimide etc.

Further, in this reaction, where the compound (III) is used in the form of a free acid, it is preferred to effect the reaction in the presence of a condensing agent, and examples thereof include carbodiimide compounds such as N,N-dicyclohexylcarbodiimide, N-cyclohexyl-N′-morpholinoethylcarbodiimide, N-cyclohexyl-N′-(4-diethylaminocyclohexyl)carbodiimide etc., reagents formed by the reaction of an amide compound such as N-methylformamide, N,N-dimethylformamide etc. with a halide such as thionyl chloride, phosphorus oxychloride, phosgene etc. (the so-called Vilsmeier reagents) etc.

Of the reaction derivatives in this reaction, the reaction using an acid halide or an acid anhydride requires the presence of an acid scavenger, and examples of the acid scavenger include organic bases such as triethylamine, trimethylamine, ethyldiisopropylamine, N,N-dimethylamine, N-methylmorpholine, pyridine etc., alkali metal compounds such as hydroxides, carbonates, bicarbonates etc. of e.g. sodium, potassium or calcium, and oxiranes such as ethylene oxide, propylene oxide etc.

This reaction is generally effected in a solvent which does not exert an adverse influence on the reaction, and as the solvent water, acetone, acetonitrile, dioxane, tetrahydrofuran, methylene chloride, chloroform, dichloroethane, N,N-dimethylformamide, or a mixed solvent thereof are used.

While the reaction temperature is not particularly restricted, the reaction is generally effected at from $-30°$ C. to $40°$ C., and the reaction reaches completion in from 30 minutes to 10 hours.

Where the thus obtained acylated product has a protecting group, the removal of the protecting group is necessary. For removing the protecting group, a method using an acid, a method using a base, a method using hydrazine etc. is employed according to the kind of protecting group. The method may be appropriately selected from among the conventional methods usually employed in the field of β-lactam and peptide syntheses.

The residue W capable of being substituted by a nucleophilic reagent in the compound of the general formula (IV) used in Process (B) is preferably, for example, an acetoxy group or a halogen atom such as chlorine, bromine and iodine.

The reaction of a compound of the general formula (IV) wherein W is acetoxy and a compound of the general formula (V):

wherein Z is as defined above is generally preferably effected in a polar solvent such as water, phosphorus buffer, acetone, acetonitrile, N,N-dimethylformamide, N,N-dimethylacetamide, tetrahydrofuran, dimethylsulfoxide, dioxane, methanol, ethanol etc. or a mixed solvent with water. The reaction is preferably effected under more or less neutral conditions and while the reaction temperature is not particularly restricted, the preferred temperature is from room temperature to about $70°$ C.

Although the time required for this reaction varies depending on the reaction conditions, it is generally 1–10 hours. Further, this reaction may be promoted by addition of an alkali metal halide such as sodium iodide, potassium iodide etc.

On the other hand, where the intended compound (I) is to be formed from a compound of the general formula (IV) wherein W is halogen, examples of the halogen include chlorine, bromine and iodine. Such halide compounds may easily be prepared according to the known processes (e.g. Japanese Patent Application Laid-open Nos. 131590/1981, 90590/1983 and 10593/1984).

This reaction is generally preferably effected in a solvent such as acetone, dioxane, tetrahydofuran, ethyl acetate, dichloromethane, acetonitrile, N,N-dimethylformamide, N,N-dimethylacetamide etc. under non-aqueous conditions. The reaction temperature is preferably 0°–50° C., and the reaction reaches completion in 1–5 hours. The thus obtained reaction mixture is further treated in a conventional manner to remove the protecting group, thereby the compound of the general formula (I) may be obtained.

The compound of the general formula (III) may be obtained according to the known processes (for example, Japanese Patent Application Laid-open No. 149289/1980), that is, it may be produced by reacting a compound of the general formula (VI):

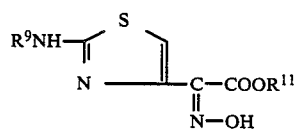  [VI]

wherein $R^9$ and $R^{11}$ are as defined above with a compound of the general formula (VII):

U—Y'  (VII)

wherein U is leaving groups such as halogen atom, methanesulfonyloxy or p-toluenesulfonyloxy group and Y' are as defined above in the presence of a base such as potassium carbonate, sodium hydride etc. in an organic solvent (e.g. N,N-dimethylformamide, tetrahydrofuran, dioxane etc.).

Further, the compound of the general formula (III) may also be produced by reacting a compound of the general formula (VIII):

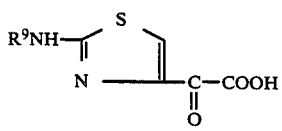  [VIII]

wherein $R^9$ is as defined above with a compound of the general formula (IX):

H₂NOY'  (IX)

wherein Y' is as defined above.

This reaction is generally effected in a solvent such as N,N-dimethylformamide, N,N-dimethylacetamide, acetonitrile, dioxane, tetrahydrofuran, alcohol or other solvent which exerts no adverse influence on the reaction, or a mixture thereof with water. The time required for the reaction is generally from 30 minutes to ten and several hours. While the reaction temperature is not particularly restricted, the reaction is generally effected at between room temperature and 60° C.

The compound of the general formula (IX) may be produced according to the known processes (e.g. Japanese Patent Application Laid-open Nos. 131758/1982 and 149289/1980), that is, by reacting N-hydroxyphthalimide with the corresponding active halide in the presence of a base and thereafter effecting hydrazine decomposition.

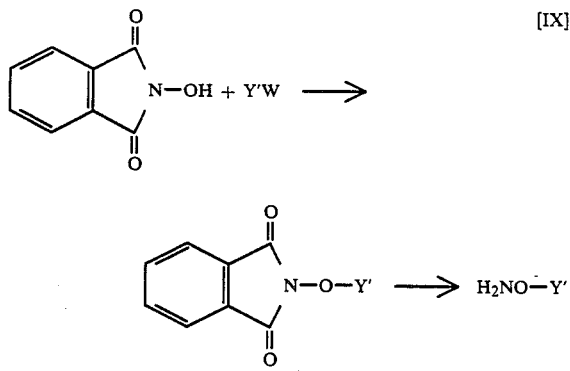  [IX]

Of the compounds of the general formula (IX), compounds of the general formula (X) having an amino group and a carboxyl group:

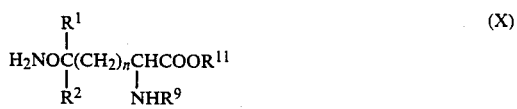  (X)

wherein $R^1$, $R^2$, $R^9$, $R^{11}$ and n are as defined above may be produced by using triphenylphosphine and diethyl azodicarboxylate under mild conditions. That is, a compound of the general formula (XI):

  (XI)

wherein $R^1$, $R^2$, $R^9$, $R^{11}$ and n are as defined above is reacted with N-hydroxyphthalimide in the presence of triphenylphosphine and diethyl azodicarboxylate to obtain a compound of the general formula (XII):

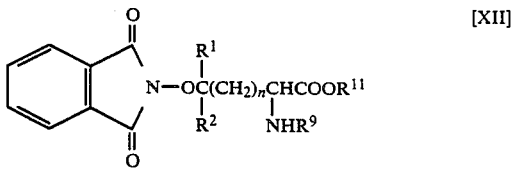  [XII]

wherein $R^1$, $R^2$, $R^9$, $R^{11}$ and n are as defined above, and this is subjected to hydrazine decomposition to obtain a compound (X).

The reaction for producing a compound of the general formula (XII) is effected by reacting one mole of a compound (XI) with 1–2 moles of triphenylphosphine and diethyl azodicarboxylate. This reaction is generally effected in an inert solvent such as dioxane, tetrahydrofuran, acetonitrile, methylene chloride, benzene, ether etc., preferably under non-aqueous conditions. While the reaction temperature is not particularly restricted, the reaction is generally effected at 0°–30° C., and the reaction reaches completion in 1–10 hours.

The thus obtained compound (XII) is subjected to hydrazine decomposition in a conventional manner to obtain the intended compound (X).

Further, a compound (Xa):

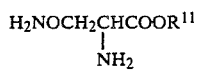

may easily be obtained by subjecting cycloserine to hydrolysis according to the process by C. H. Stammer et al. (J.O.C., Vol. 27, p. 2957 (1962)).

The compounds of the general formula (V) constituting the 3-position substituent of the compounds of this invention may be synthesized by the following processes.

That is, a 1-substituted cycloalkano [e] 2-thiopyridone may be produced either by N-alkylating a cycloalkano [e] 2-pyridone synthesized according to the process by A. I. Meyers et al. (J. Org. Chem., 1435 (1964)) and thereafter treating with phosphorus pentasulfide:

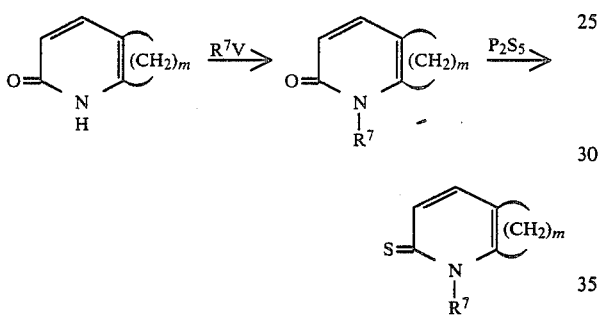

wherein $R^7$ and m are as defined above and V is halogen, or by halogen substitution, then N-substitution and treatment with KSH:

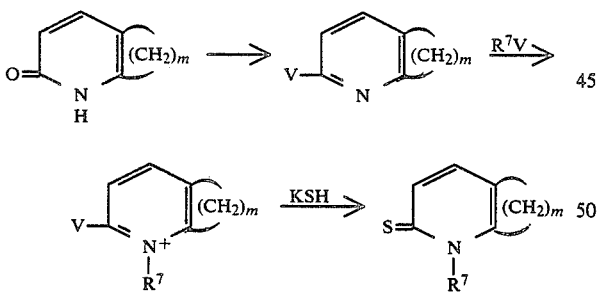

A 1-substituted cycloalkano [b] 4-thiopyridine may be synthesized by reacting a cycloalkano [b] 4-pyrone synthesized according to the process, e.g., those by S. Hünig et al. (Chem. Ber. 94, 486 (1961)), by G. Jäger (Ann. Chem., 1989 (1976)) etc. with $R^7NH_2$ and thereafter treating with phosphorus pentasulfide:

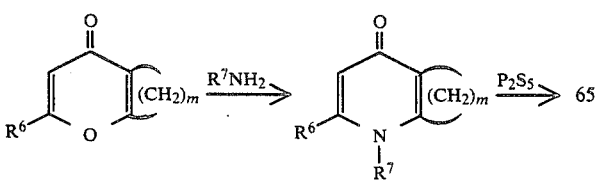

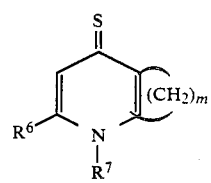

wherein $R^6$, $R^7$ and m are as defined above.

Alternatively, this may be synthesized by reacting a 4-halo-2,3-cycloalkanopyridine obtained by the process by R. A. Abramovitch et al. (J. Am. Chem. Soc., 1525 (1981)) or by treating the aforesaid cycloalkano [b] 4-pyrone with ammonia and then substituting with a halogen:

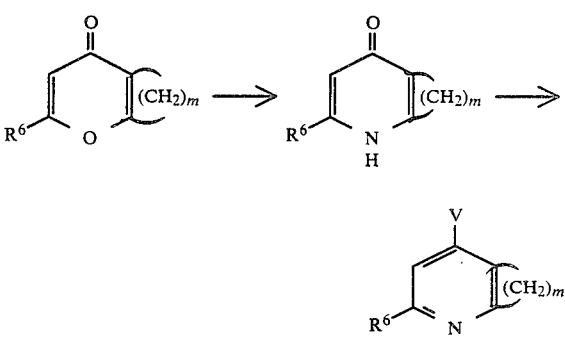

wherein V is halogen and $R^6$ and m are as defined above with a halide compound of the general formula:

$$V-R^7$$

wherein V and $R^7$ are as defined above, and thereafter treating with KSH:

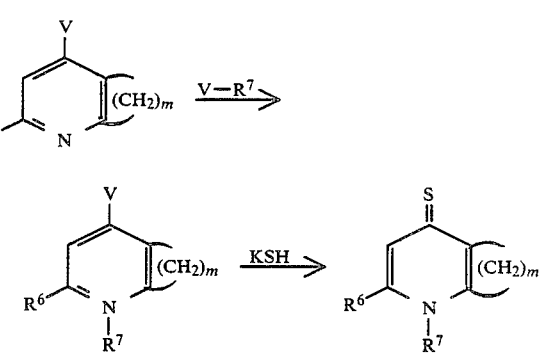

wherein V, $R^6$, m and $R^7$ are as defined above.

A 1-substituted cyclopentano [c] 2-thiopyridone may be obtained by the following process. That is, by treating 5-methoxycarbonyl-cyclopentano [c] 2-pyrone with ammonia, decarboxylation takes place to yield cyclopentano [c] 2-pyridone, which is further subjected to the following series of treatments to lead to the desired 1-substituted cyclopentano [c] 2-thiopyridone:

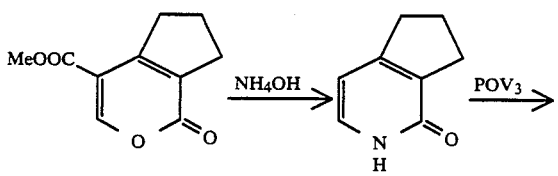

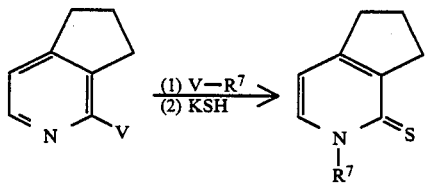

wherein V and $R^7$ are as defined above.

The intermediate cyclopentano [c]]2-pyridone may also be prepared by the reduction treatment (dehalogenation) of 6-chlorocyclopentano [c] 2-pyridone obtained by the process by G. Simchen et al. (Chem. Ber. 103, 389 (1970)).

A 1-substituted alkylpyridothione may be produced according to, for example, the process described in the Journal of Chemical Society (London), 3610 (1958), as illustrated by the following reaction scheme, thereby a 1-(1-carboxy)alkyl-4-pyridothione (XV) and a 1-(1-carboxy)alkyl-2-pyridothione (XVI) are produced:

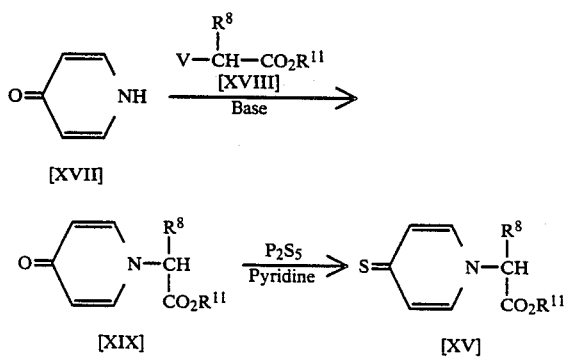

This reaction comprises reacting 4-pyridone (XVII) with a 1-halogeno fatty acid ester in an inert solvent in the presence of a base to obtain a 1-substituted 4-pyridone (XIX), and thereafter heating with phosphorus pentasulfide in pyridine to obtain a 1-(1-carboxy)alkyl-4-pyridothion (XV). $R^{11}$ in the formulae (XV), (XVIII) and (XIX) is a protecting group such as p-nitrobenzyl, diphenylmethyl, t-butyl, trimethylsilyl, allyl groups etc. However, in order to simultaneously deprotect the protecting group for the carboxylic acid at the 4-position of the cepharosporin and the protecting group in the side-chain at the 7-position in the last step of the process for the production of the compounds of this invention (I), the diphenylmethyl and t-butyl groups are preferred. V in the formula (XVIII) is halogen, and chlorine, bromine and iodine are suitable. The reaction solvent in the reaction for obtaining the 1-substituted 4-pyridone (XIX) may be a conventional inert solvent, suitably dioxane, tetrahydrofuran, dimethoxyethane, dimethylformamide, methylene chloride etc. The reaction temperature is 0°–100° C., preferably 20°–30° C. The base used in this reaction may be a conventional base such as NaOH, KOH, $Na_2CO_3$, $K_2CO_3$, t-BuO$^-$K$^+$ etc.

The reaction from (XIX) to (XV) is a treatment with phorphorus sulfide in pyridine to convert the carbonyl group to a thiocarbonyl group, and as the phosphorus sulfide compound, phosphorus pentasulfide ($P_2S_5$) or Lawesson reagent

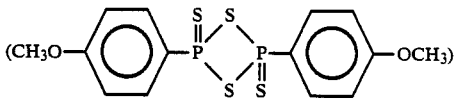

is preferred. The reaction temperature is 30°–150° C., preferably 80°–120° C. This reaction with the phosphorus sulfide may be effected in pyridine or an inert solvent such as benzene, toluene, etc. and reaches completion in 1 hour.

The production of the 1-(1-carboxy)alkyl-2-pyridothione (XVI) may be effected in a manner similar to the above but using 2-pyridone

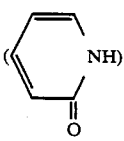

as a starting material.

This invention is more particularly described by Reference Examples and Examples described below. In the examples, NMR data are δ values either using water peak (δ value 4.80) as the standard when measured in deuterium oxide or using TMS (tetramethylsilane) as the standard when measured in other deuterated solvent, unless otherwise specified.

REFERENCE EXAMPLE 1

1-Methyl-cyclopentano [e] 2-thiopyridone 280 mg of potassium hydroxide was added to a solution of 700 mg of cyclopentano [e] 2-pyridone in 5 ml of methanol, and concentrated to dryness. The obtained potassium salt was suspended in 10 ml of acetone, 2 g of methyl iodide was added, and reacted with stirring at 50° C. for 3 hours.

The reaction mixture was concentrated to dryness, the residue was dissolved in 3 ml of chloroform, washed with 20 ml of water, and concentrated under reduced pressure to obtain 710 mg of 1-methyl-cyclopentano [e] 2-pyridone. Thereafter, 505 mg of this was mixed with 743 mg of phosphorus pentasulfide and reacted by heating at 170° C. for 2 hours.

After cooling, 5.29 ml of a 3N sodium hydroxide aqueous solution was added to the reaction mixture, which was then diluted with water and extracted with 30 ml of chloroform. The extract was concentrated, and then purified on a silica gel column (developing solvent: 5:1 chloroform-methanol) to obtain 380 mg of the title compound as crystals. This was recrystallized from acetonitrile to obtain pale yellow needles.

m.p. 168°–169° C.

NMR (CDCl$_3$) δ: 2.21 (m, 2H), 2.85 (t, 2H), 3.05 (t, 2H), 3.99 (s, 3H), 7.11 (d, 1H), 7.60 (d, 1H).

REFERENCE EXAMPLE 2

1-Methyl-cyclohexano [e] 2-thiopyridone 3.78 g of cyclohexano [e] 2-pyridone potassium salt was suspended in 30 ml of acetone, 4 g of methyl iodide was added, and reacted with stirring at 50° C. for 4 hours. The reaction mixture was concentrated, then, after adding 30 ml of water, extracted with 50 ml of chloroform and concentrated to dryness under reduced pressure to obtain 3.7 g of 1-methyl-cyclohexano [e] 2-pyridone.

900 mg of the thus obtained 1-methyl-cyclohexano [e] 2-pyridone was mixed thoroughly with 1.21 g of phosphorus pentasulfide, and reacted by heating at 160° C. for 1.5 hours. After cooling, 8.6 ml of a 3N sodium hydroxide aqueous solution was added to the reaction mixture, which was then diluted with water and extracted with 50 ml of chloroform. The extract was concentrated, and then purified on a silica gel column (developing solvent: 5:1 chloroform-methanol) to obtain 650 mg of the title compound as crystals. This was recrystallized from acetonitrile to obtain pale yellow needles.

m.p. 149.5°–150.5° C.

NMR (CDCl$_3$) δ: 1.80 (m, 2H), 1.85 (m, 2H), 2.61 (t, 2H), 2.77 (t, 2H), 4.07 (s, 3H), 6.93 (d, 1H), 7.63 (d, 1H).

REFERENCE EXAMPLE 3

1,6-Dimethyl-cyclohexano [b] 4-thiopyridone 30 ml of a 40% methylamine aqueous solution was added to a solution of 7.5 g of 6-methyl-cyclohexano [b]-4-pyrone in 10 ml of dioxane, and heated in a sealed tube at 100° C. for 24 hours. The obtained solution was concentrated to dryness, and purified by silica gel column chromatography (developing solvent: 20:1 chloroform-methanol) to obtain 1.0 g of 1,6-dimethyl-cyclohexano [b]-4-pyridone. Thereafter, 618 mg of this was mixed thoroughly with 770 mg of powdered phosphorus pentasulfide and heated at 140° C. for 2 hours. After cooling, a 1N aqueous sodium hydroxide solution was added to adjust the pH to 7.5, and the reaction mixture was extracted with 30 ml of chloroform. The chloroform was distilled off, and the residue was purified by silica gel column chromatography (developing solvent: 20:1 chloroform-methanol) to obtain 400 mg of the title compound as crystals. This was recrystallized from acetonitrile to obtain pale yellow needles.

m.p. 206°–207° C.

NMR (CDCl$_3$) δ: 1.6–2.0 (m, 4H), 2.36 (s, 3H), 2.70 (t, 2H), 2.86 (t, 2H), 3.61 (s, 3H), 7.42 (s, 1H)

REFERENCE EXAMPLE 4

1,6-Dimethyl-cyclopentano [b]-4-thiopyridone 15 ml of a 40% methylamine aqueous solution was added to a solution of 3.0 g of 6-methyl-cyclopentano [b]-4-pyrone in 5 ml of dioxane, and heated in a sealed tube at 100° C. for 24 hours. The obtained solution was concentrated to dryness, and purified on silica gel column chromatography (developing solvent: 20:1 chloroform-methanol) to obtain 350 mg of 1,6-dimethyl-cyclopentano [b]-4-pyridone.

Thereafter, 155 mg of this was mixed thoroughly with 210 mg of powdered phosphorus pentasulfide and heated at 140° C. for one hour 40 minutes. After cooling, a 1N aqueous sodium hydroxide solution was added to adjust the pH to 7.5, and the reaction mixture was extracted with 30 ml of chloroform. The chloroform was distilled off, and the residue was purified on silica gel column chromatography (developing solvent: 30:1 chloroform-methanol) to obtain 100 mg of the title compound as crystals. This was recrystallized from acetonitrile to obtain yellow needles.

m.p. 250° C. (dec.)

NMR (CDCl$_3$) δ: 2.12 (m, 2H), 2.34 (s, 3H), 2.98 (t, 2H), 3.06 (t, 2H), 3.62 (s, 3H), 7.23 (s, 1H).

REFERENCE EXAMPLE 5

1-Methyl-cyclopentano [b] 4-thiopyridone 20 ml of a 40% methylamine aqueous solution was added to a solution of 2.05 g of cyclopentano [b]-4-pyrone in 20 ml of dioxane, and heated in a sealed tube at 100° C. for 15 hours. The obtained solution was concentrated to dryness, and, after adding 50 ml of ethyl acetate, stirred at room temperature for an hour. The separated insoluble matter was filtered off, to obtain 1.63 g of 1-methyl-cyclopentano [b]-4-pyridone.

Thereafter, 1.18 g of this was mixed thoroughly with 1.78 g of phosphorus pentasulfide and heated at 140° C. for 2 hours. After cooling, a 1N sodium hydroxide aqueous solution was added to adjust the pH to 7.5, and the reaction mixture was extracted with chloroform. The chloroform was distilled off, and the residue was washed with ethyl acetate to obtain 840 mg of the title compound as crystals. This was recrystallized from chloroform to obtain yellow needles.

m.p. 213°–213.5° C.

NMR (CDCl$_3$) δ: 2.16 (m, 2H), 2.99 (t, 2H), 3.03 (t, 2H), 3.71 (s, 3H), 7.07 (d, 1H), 7.26 (d, 1H)

REFERENCE EXAMPLE 6

1-Allyl-cyclopentano [b] 4-thiopyridone

A suspension of 5 g of cyclopentano [b]-4-pyrone and 50 ml of conc. ammonia water was heated in a sealed tube at 100° C. for 3 hours. After cooling, the tube was opened, and the separated crystals were filtered off and dried to obtain 3.73 g of cyclopentano [b]-4-pyridone.

Thereafter, 1 g of this compound was stirred with 1.5 ml of phosphorus oxychloride while heating at 135° C. for an hour, the reaction mixture was shaken with ether and 10% hydrochloric acid, and the ether layer was further extracted twice with 10% hydrochloric acid. The aqueous layer was made alkaline with a 20% sodium hydroxide aqueous solution, and extracted three times with ether. This ether layer was washed with water, dried over magnesium sulfate, and concentrated to obtain 1.2 g of 4-chloro-2,3-cyclopentanopyridine as an oil.

Thereafter, 1.2 g of this was stirred with 3 ml of allyl bromide while heating at 50° C. overnight, concentrated, then acetone was added, and the separated crystals were filtered off and dried to obtain 1.73 g of 1-allyl-4-chloro-2,3-cyclopentanopyridinium bromide.

Thereafter, 1.64 g of this was added to a potassium hydrogensulfide aqueous solution (prepared by dissolving 2.15 g of potassium hydroxide in 30 ml of water and passing hydrogen sulfide gas until the color of phenol-phthalein disappeared), and stirred at room temperature for 20 minutes. 30 ml of water was added, the formed crystals were filtered off, washed with water, and dried to obtain 839 mg of the title compound.

m.p. 158°–159° C.

NMR (CDCl$_3$) δ: 1.9–2.15 (m, 2H), 2.8–3.2 (m, 4H), 4.4–4.6 (m, 2H), 5.16 (d, 1H), 5.58 (d, 1H), 5.7–6.3 (m, 1H), 7.10 (d, 1H), 7.35 (d, 1H).

REFERENCE EXAMPLE 7

1,5-Dimethyl-cyclopentano [b] 4-thiopyridone 25 ml of a 40% methylamine aqueous solution was added to a solution of 2.0 g of 5-methyl-cyclopentano [b]-4-pyrone in 15 ml of dioxane, and heated in a sealed tube at 100° C. for 15 hours. The obtained solution was concentrated to dryness to obtain 2.1 g of 1,5-dimethyl-cyclopentano [b]-4-pyridone.

Thereafter, 2.1 g of this was mixed thoroughly with 2.8 g of powdered phosphorus pentasulfide and heated at 120° C. for 2.5 hours. After cooling, a 1N aqueous sodium hydroxide solution was added to adjust the pH to 7.5, and the reaction mixture was extracted with 100 ml of chloroform. The chloroform was distilled off, then 20 ml of acetone was added and stirred, and the insoluble matter was filtered off to obtain 1.5 g of the title compound.

NMR (DMSO-$d_6$) δ: 2.07 (m, 2H), 2.15 (s, 3H), 2.81 (t, 2H), 3.07 (t, 2H), 3.69 (s, 3H), 7.71 (s, 1H).

REFERENCE EXAMPLE 8

1-Diphenylmethoxycarbonylmethyl-4-pyridone 1.37 g of 4-hydroxypyridine was dissolved in 16 ml of THF, then 1.63 g of potassium tert-butoxide was added and reacted overnight. Thereafter, 3.12 g of diphenylmethyl bromoacetate was added and reacted for 6 hours. After the reaction, the solvent was removed, the residue was dissolved in chloroform and washed with water. This was dried over magnesium sulfate, the solvent was removed, and the residue was purified on silica gel chromatography using chloroform-methanol (20:1) to obtain 2.25 g of the title compound (55%).

IR (Nujol) $v cm^{-1}$: 1740, 1640.

NMR (CDCl$_3$) δ: 4.40 (2H S), 6.3 (2H d J=6), 6.90 (1H S), 7.00–7.50 (12H m).

1-Diphenylmethoxycarbonylmethyl-4-thiopyridone 210 mg of 1-diphenylmethoxycarbonyl-4-pyridone was dissolved in 2.1 ml of pyridine, 222 mg of P$_2$S$_5$ was added and reacted at 100° C. for an hour. After the reaction, the solvent was removed, chloroform was added, then pH was adjusted to 7.8 with NaHCO$_3$, the mixture was washed with water and dried over magnesium sulfate. The solvent was removed, and the residue was purified on silica gel chromatography using chloroform-methanol (20:1) to obtain 130 mg of the title compound (58%).

NMR (CDCl$_3$) δ: 5.10 (2H s), 6.85 (1H S), 7.15 (2H d J=6), 7.30 (10H S), 7.55 (2H d J=6).

REFERENCE EXAMPLE 9

1-Diphenylmethoxycarbonylmethyl-2-pyridone 4.00 g of 2-hydroxypyridine and 19.2 g of diphenylmethyl bromoacetate were dissolved in 80 ml of DMF, 8.70 g of K$_2$CO$_3$ was added, and reacted at 60° C. for 4 hours.

The reaction mixture was filtered, the filtrate was concentrated under reduced pressure, and the residue was purified on silica gel column chromatography (developing solvent: ethyl acetate) to obtain 9.66 g (yield 72%) of the title compound as crystals.

IR (CHCl$_3$) $v cm^{-1}$: 1750, 1663.

NMR (CDCl$_3$) δ: 4.73 (2H S methylene), 6.91 (1H S —CHPh$_2$), 6.00–7.50 (14H m pyridone phenyl×2).

1-Diphenylmethoxycarbonylmethyl-2-thiopyridone 640 mg of 1-diphenylmethoxycarbonylmethyl-2-pyridone and 492 mg of 2,4-bis-(4-methoxyphenyl)-2,4-dithioxo-1,2,3,4-dithiadiphosphetane were dissolved in 6 ml of toluene, then heated at reflux in a nitrogen stream for 30 minutes, and concentrated.

The residue was purified on silica gel column chromatography (developing solvent: PhMe-EtOAc (=4:1)) to obtain 480 mg (yield 72%) of the title compound.

IR (CHCl$_3$) $v cm^{-1}$: 1750, 1140

NMR (CDCl$_3$) δ:
5.23 (2H S methylene), 6.90 (1H S —CHPh$_2$), 6.40–7.80 (14H m pyridothione phenyl×2).

REFERENCE EXAMPLE 10

1-(1-Diphenylmethoxycarbonyl-1-ethyl)-4-thiopyridone 2.31 g of 4-pyridone synthesized in a manner similar to that in Reference Example 8 was dissolved in 23 ml of pyridine, 1.55 g of P$_2$S$_5$ was added, and reacted at 90° C. for an hour.

After the reaction, the solvent was removed, chloroform was added, the pH was adjusted to 7.8 with NaHCO$_3$, the mixture was washed with water, and dried over magnesium sulfate. The solvent was removed, and the residue was purified on silica gel column chromatography using chloroform-methanol (20:1) to obtain 1.38 g of the title compound (57%).

IR (Nujor) $v cm^{-1}$: 1754.

NMR (DMSO-$d_6$) δ: 1.70 (3H d J=6), 4.65 (1H q J=6), 6.85 (1H S), 7.10 (2H d J=6), 7.30 (10H S), 7.55 (2H d J=6).

REFERENCE EXAMPLE 11

1-(1-Diphenylmethoxycarbonyl-1-benzyl)-4-thiopyridone 1.48 g of 4-pyridone synthesized in a manner similar to that in Reference Example 8 was dissolved in 15 ml of pyridine, 832 mg of P$_2$S$_5$ was added, and reacted at 70° C. for an hour.

After the reaction, the solvent was removed, chloroform was added, the pH was adjusted to 7.8 with NaHCO$_3$, the mixture was washed with water and dried over magnesium sulfate. The solvent was removed, and the residue was purified on silica gel chromatography using chloroform-ethyl acetate (10:1) to obtain 1.1 g of the title compound (70%).

IR (Nujol) $v cm^{-1}$: 1740.

NMR (CDCl$_3$) δ: 5.80 (1H S), 6.95 (1H S), 7.00–7.40 (19H m).

REFERENCE EXAMPLE 12

1-Carboxymethyl-cyclopentano [b]-4-thiopyridone (a) Cyclopentano [b]-4-pyrone (5.5 g) and conc. ammonia (50 ml) were mixed, and heated in a sealed tube at 100° C. for 3 hours. After cooling, the crystals were filtered off, washed with a small quantity of water, and dried to obtain 5.23 g (95%) of cyclopentano [b]-4-pyridone. Thereafter, phosphorus oxychloride (7 ml) was added to this cyclopentano [b]-4-pyridone (6.3 g), and heated at 135° C. for an hour. After cooling, the reaction mixture was dissolved in 10% hydrochloric acid (60 ml) and washed with diethyl ether (60 ml). The ether layer was extracted with 10% hydrochloric acid (30 ml), the aqueous layers were combined, and made alkaline with 20% sodium hydroxide. This was extracted with diethyl ether (150 ml×3), dried on magnesium sulfate, and the ether was distilled off to obtain 6.25 g (90%) of 4-chloro-cyclopentano [b]-pyridine.

(b) The 4-chloro-cyclopentano [b]-pyridine (1.2 g) and ethyl bromoacetate (1.2 ml) were mixed and stirred at 60° C. for an hour.

The solidified reaction mixture was slurried in ether, and the crystals were filtered off to obtain 2.27 g (92%) of 1-ethoxycarbonylmethyl-4-chloro-cyclopentano [b]-pyridinium bromide.

NMR ($D_2O$) δ: 1.28 (t, 3H), 2.15–2.62 (m, 2H), 3.05–3.55 (m, 4H), 4.32 (q, 2H), 5.43 (s, 2H), 7.90 (d, 1H), 8.47 (d, 1H).

This 1-ethoxycarbonylmethyl-4-chloro-cyclopentano [b]-pyridinium bromide salt (1.6 g) was added with ice cooling to a KSH solution (prepared by introducing hydrogen sulfate gas into a solution of 1.8 g of potassium hydroxide in 25 ml of water until the red color of phenolphthalein disappeared). After stirring at room temperature for 15 minutes, the formed crystals were filtered off, and dried to obtain 1.03 g (87%) of 1-ethoxycarbonylmethyl-cyclopentano [b]-4-thiopyridone.

NMR ($CDCl_3$) δ: 1.26 (t, 3H), 1.8–2.3 (m, 2H), 2.8–3.3 (m, 4H), 4.28 (q, 2H), 4.65 (s, 2H), 7.05 (d, 1H), 7.24 (d, 1H).

(c) The 1-ethoxycarbonylmethyl-cyclopentano [b]-4-thiopyridone (712 mg) was dissolved in 4 ml of DMF, 4 ml of 1N sodium hydroxide was added, and stirred at room temperature for an hour. 10 ml of water was added, the mixture was made acidic with 1N hydrochloric acid, concentrated, and the crystals were filtered off. Further crystals were filtered off from the mother liquor, and dried to obtain 505 mg (80%) of the title compound.

NMR ($CD_3OD$) δ: 1.95–2.4 (m, 2H), 2.8–3.3 (m, 4H), 4.90 (s, 2H), 7.30 (d, 1H), 7.56 (d, 1H).

REFERENCE EXAMPLE 13

1-Carbamoylmethyl-cyclopentano [b] 4-thiopyridone 240 mg of 1-ethoxycarbonylmethyl-cyclopentano [b]-4-thiopyridone was suspended in 2 ml of conc. ammonia water, and reacted with ice cooling for an hour. After the reaction, the reaction mixture was concentrated to dryness under reduced pressure to obtain 200 mg of the title compound.

NMR (DMSO-$d_6$) δ: 2.03 (m, 2H), 2.76 (t, 2H), 2.92 (t, 2H), 4.68 (s, 2H), 7.05 (d, 1H), 7.26 (d, 1H).

Compounds of Reference Examples 14 and 15 were obtained by treating in a manner similar to that in Reference Example 12 except that the ethyl bromoacetate used in Reference Example 12 (b) was replaced by Reagent (A) indicated in the respective Reference Examples.

REFERENCE EXAMPLE 14

1-Cyanomethyl-cyclopentano [b] 4-thiopyridone

Reagent (A): Bromoacetonitrile

NMR ($CDCl_3 + CD_3OD$) δ: 2.22 (m, 2H), 3.04 (t, 2H), 3.18 (t, 2H), 3.85 (s, 2H), 7.36 (d, 1H), 7.40 (d, 1H).

REFERENCE EXAMPLE 15

1-Methylthiomethyl-cyclopentano [b] 4-thiopyridone

Reagent (A): Chloromethyl methyl sulfide

NMR ($CDCl_3$) δ: 2.15 (s, 3H), 2.17 (m, 2H), 3.04 (t, 2H), 3.09 (t, 2H), 4.84 (s, 2H), 7.14 (d, 1H), 7.34 (d, 1H).

REFERENCE EXAMPLE 16

1-(2-Hydroxyethyl)-cyclopentano [b] 4-thiopyridone (a) 927 mg of 4-chloro-cyclopentano [b]-pyridine and 0.6 ml of 2-bromoethanol were mixed, and stirred at 50° C. for 30 minutes, then at 80° C. for an hour. After concentrating under reduced pressure, the residue was dissolved in water and washed with ether. The ether layers were combined and extracted with a small quantity of water. The aqueous layers were combined and concentrated to dryness. The residue was chromatographed on a silica gel (40 g) column and eluted with chloroform-methanol (2:1). The fractions containing 1-(2-hydroxyethyl)-4-chloro-cyclopentano [b]-4-pyridinium bromide were collected, the solvent was distilled off, and then the residue was crystallized from acetone to obtain 536 mg (32%) as crystals.

NMR ($D_2O$) δ: 2.15–2.65 (m, 2H), 3.1–3.7 (m, 4H), 3.9–4.21 (m, 2H), 4.5–4.8 (m, 2H), 7.82 (d, 1H), 8.46 (d, 2H).

(b) 520 mg of the 1-(2-hydroxyethyl)-4-chloro-cyclopentano [b]-4-pyridinium bromide was added to an KSH solution (prepared by introducing hydrogen sulfide gas into a solution of 0.66 g of potassium hydroxide in 10 ml of water until the color of phenolphthalein disappeared), and stirred at room temperature for 2 hours. After the reaction, sodium chloride was added, the mixture was extracted to 10 times with dichloromethane, dried on magnesium sulfate, and the dichloromethane was distilled off. The residue was crystallized from acetone-ether, filtered off, and dried to obtain 279 mg (77%) of the title compound.

NMR ($D_2O + CD_3OD$) δ: 1.88–2.35 (m, 2H), 2.67–3.2 (m, 4H), 3.83 (t, 2H), 4.17 (t, 2H), 7.28 (d, 1H), 7.59 (d, 1H).

REFERENCE EXAMPLE 17

1-(2-Dimethylaminoethyl)-cyclopentano [b]-4-thiopyridone (a) 680 mg of cyclopentano [b]-4-thiopyridone and 1 ml of N,N-dimethylethylenediamine were mixed, stirred while heating at 120° C. for 7 hours, then the reaction mixture was concentrated under reduced pressure, and the residue was chromatographed on a silica gel (40 g) column. This was eluted with chloroform-methanol (3:1) to obtain the desired compound. This product was left at room temperature to crystallize. Ethyl ether was added thereto to make a slurry and filtered to obtain 654 mg of 1-(2-dimethylaminoethyl)-cyclopentano [b] 4-pyridone.

NMR ($CDCl_3$) δ: 2.20 (s, 6H), 1.95–2.30 (m, 2H), 2.54 (t, 2H), 2.7–3.2 (m, 4H), 3.81 (t, 2H), 6.26 (d, 1H), 7.24 (d, 1H).

(b) 515 mg of the 1-(2-dimethylaminoethyl)cyclopentano [b]-4-pyridone and 555 mg of phosphorus pentasulfide were mixed thoroughly, and heated at 140° C. for 20 minutes. After cooling, this was made alkaline by adding water and 1N sodium hydroxide, adequately crushed, and extracted 4 times with chloroform. The extract was washed with saline, dried on magnesium sulfate, and the chloroform was distilled off. The formed crystals were slurried with ethyl acetate, and filtered off to obtain 331 mg (60%) of the title compound.

NMR (CDCl$_3$) δ: 2.22 (s, 6H), 1.95-2.3 (m, 2H), 2.60 (t, 2H), 2.85-2.25 (m, 4H), 3.92 (t, 2H), 7.14 (d, 1H), 7.28 (d, 1H).

REFERENCE EXAMPLE 18

1-Hydroxy-cyclopentano [b] 4-thiopyridone (a) 920 mg of 4-chloro-cyclopentano [b]-pyridine was dissolved in 4 ml of acetic acid and heated to 90° C. 30% hydrogen peroxide was added thereto, and stirred for 4 hours. 4 ml of water was added to dilute, and a sodium thiosulfate aqueous solution was added until potassium iodide—starch paper lost the blue color. This reaction mixture was concentrated, then a sodium bicarbonate aqueous solution and saline were added, and extracted 3 times with chloroform. This was dried on magnesium sulfate, and the chloroform was distilled off. The formed crystals were slurried with diethyl ether, then filtered and dried to obtain 700 mg (67%) of 4-chloro-cyclopentano [b]-pyridine-N-oxide.

NMR (CDCl$_3$) δ: 1.95-2.45 (m, 2H), 2.90-3.45 (m, 4H), 7.10 (d, 1H), 8.10 (d, 1H).

(b) 340 mg of the 4-chloro-cyclopentano [b]-pyridine-N-oxide was added to an KSH solution (prepared by blowing hydrogen sulfide gas into a solution of 717 mg of potassium hydroxide in 10 ml of water until the red color of phenolphthalein disappeared), and heated in a sealed tube at 100° C. overnight. After cooling, the reaction mixture was concentrated under reduced pressure, and, after adding 10 ml of water, made acidic with conc. hydrochloric acid. The formed precipitates were filtered off, and dried to obtain 229 mg (32%) of the title compound.

NMR (CDCl$_3$+CD$_3$OD) δ: 2.1-2.45 (m, 2H), 2.9-3.4 (m, 4H), 7.28 (d, 1H), 7.73 (d, 1H).

REFERENCE EXAMPLE 19

1-(2-Sulfoethyl)-cyclopentano [b] 4-thiopyridone 765 mg of 4-chloro-2,3-cyclopentenopyridine and 470 mg of 2-bromoethanesulfonic acid were reacted at 80° C. for 2 hours.

After the reaction, dichloromethane and water were added, the pH of the aqueous layer was adjusted to 8 with a saturated sodium bicarbonate aqueous solution, the aqueous layer was separated, washed with dichloromethane, then, the pH was adjusted to 6.5 and this was concentrated to dryness under reduced pressure. This was then dissolved in methanol and purified by column chromatography on Sephadex LH-20 (Pharmacia) (packed using methanol) to obtain 110 mg of 1-(2-sulfoethyl)-3-chloro-cyclopentenopyridinium.

This was dissolved in 2 ml of water, the pH was adjusted to 7 with a 1N sodium hydroxide aqueous solution, and 1 ml of a 20% potassium hydrogensulfide aqueous solution was added with ice cooling. After the reaction, the pH of the reaction mixture was adjusted to 1.5 with 5N hydrochloric acid, and this was concentrated to dryness under reduced pressure. This was dissolved in methanol, and, after removing the insoluble matter by filtration, purified by column chromatography on Sephadex LH-20 to obtain 65 mg of the title compound.

NMR (MeOH-d$_4$) δ: 2.39 (m, 2H), 3.08 (t, 2H), 3.45 (t, 2H), 3.54 (t, 2H), 4.79 (t, 2H), 7.77 (d, 1H), 8.43 (d, 1H).

REFERENCE EXAMPLE 20

1-Methyl-cyclopentano [c] 2-thiopyridone (a) 20 ml of conc. ammonia water was added to 2 g of 5-methoxycarbonyl-cyclopentano [c] 2-pyrone, and reacted by heating in a sealed tube at 100° C. for 10 hours. The reaction mixture was concentrated, then subjected to silica gel chromatography, and eluted with chloroform-methanol (5:1) to obtain 1.5 g of cyclopentano [c] 2-pyridone, i.e., the decarbonized pyridone form.

(b) Thereafter, 1 g of the cyclopentano [c] 2-pyridone was treated in 10 ml of phosphorus oxychloride at 100° C. for 1.5 hours, and concentrated to dryness. The residue was dissolved in 50 ml of ethyl acetate, washed with a 10% sodium bicarbonate aqueous solution and saturated saline, and concentrated under reduced pressure to obtain 950 mg of 2-chloro-3,4-cyclopentenopyridine.

(c) 750 mg of the thus obtained 2-chloro-3,4-cyclopentenopyridine was dissolved in 8 ml of methyl iodide, and left at room temperature for 10 hours, thereby precipitates were formed. The supernatant was removed, the residue was dissolved in 5 ml of a 20% potassium hydrogensulfide aqueous solution, reacted at room temperature for an hour, diluted with 10 ml of water, extracted with 50 ml of chloroform, and concentrated to dryness to obtain 680 mg of the title compound.

NMR (CDCl$_3$) δ: 2.10 (m, 2H), 2.96 (t, 2H), 3.04 (t, 2H), 4.03 (s, 3H), 6.60 (d, 1H), 7.65 (d, 1H).

REFERENCE EXAMPLE 21

1-Methyl-cyclopentano [c] 2-thiopyridone (a) 420 mg of 6-chloro-cyclopentano [c]-2-pyridone was dissolved in 30 ml of benzene, 40 mg of 10% Pd/C was added, and hydrogenation was effected at room temperature and 2 atm. for 2 hours. The catalyst was removed by filtration, and the solvent was distilled off to quantitatively obtain cyclopentano [c]-2-pyridone.

(b) 350 mg of the cyclopentano [c]-2-pyridone was dissolved in 5 ml of dimethylformamide, 150 mg of 55% sodium hydride was added, and stirred at room temperature for 15 minutes. Thereafter, 1.2 ml of methyl iodide was added, and reacted at room temperature for 2 hours. This was concentrated, then dissolved by adding dichloromethane, and washed with a small quantity of water. The dichloromethane layer was dried on magnesium sulfate, and concentrated to obtain 330 mg of 1-methyl-cyclopentano [c] 2-pyridone.

(c) 250 mg of the 1-methyl-cyclopentano [c] 2-pyridone and 335 mg of phosphorus pentasulfide were mixed thoroughly and reacted at 140° C. for 2 hours. The obtained black solid was dissolved in a 1N sodium hydroxide solution together with dichloromethane, and extracted with dichloromethane. The dichloromethane layer was dried on magnesium sulfate, and directly passed through 5 g of silica gel for column chromatography, and washed with dichloromethane. The solvent was removed to obtain 150 mg of the title compound. The spectral data of this product showed good agreement with those of Reference Example 20.

REFERENCE EXAMPLE 22

1-(2,2,2-Trifluoroethyl)-cyclopentano [b]-4-thiopyridone 1.3 g of cyclopentano [b] 4-pyrone and 3.9 g of 2,2,2-trifluoroethylamine hydrochloride were dissolved in 30 ml of N,N-dimethylformamide, and reacted by heating in a sealed tube at 140° C. for 7 hours. The reaction mixture was concentrated, then dissolved in 300 ml of ethyl acetate, and washed twice with 100 ml of water. The ethyl acetate layer was dried, and concentrated to dryness to obtain 1.5 g of 1-(2,2,2-trifluoroethyl)-cyclopentano [b]-4-pyridone.

Thereafter, 1.11 g of this was dissolved in 8 ml of pyridine, 1.134 g of phosphorus pentasulfide was added, and stirred at 110° C. for 2 hours. The reaction mixture was concentrated to dryness, and 100 ml of chloroform and 50 ml of water were added to the residue, which was adjusted to pH 9 with 5N sodium hydroxide. The chloroform layer was dried, and then concentrated to dryness to obtain 0.85 g of 1-(2,2,2-trifluoroethyl)-cyclopentano [b]-4-thiopyridone.

NMR (CDCl$_3$) δ: 2.19 (m, 2H), 3.0–3.1 (m, 4H), 7.41 (m, 2H), 7.14 (d, 1H), 7.34 (d, 1H).

REFERENCE EXAMPLE 23

1-Cyclopropyl-4-thiopyridone 990 mg of 4H-pyran-4-on and 1.5 g of cyclopropylamine were dissolved in 15 ml of N,N-dimethylformamide, and reacted by heating in a sealed tube at 100° C. for 6 hours. The reaction mixture was concentrated to dryness, dissolved in 80 ml of chloroform and washed with 40 ml of water. The chloroform layer was concentrated to obtain 2.2 g of 1-cyclopropyl-4-pyridone.

Thereafter, 2.1 g of this was dissolved in 15 ml of pyridine, 3.445 g of phosphorus pentasulfide was added, and stirred at 100° C. for 1.5 hours. The reaction mixture was concentrated to dryness, and 100 ml of chloroform and 50 ml of water were added to the residue, which was then adjusted to pH 9 with 5N sodium hydroxide. The chloroform layer was dried, and concentrated to dryness to obtain 1.3 g of 1-cyclopropyl-4-thiopyridone.

NMR (DMSO-d$_6$) δ: 1.02 (m, 2H), 1.06 (m, 2H), 3.67 (m, 1H), 7.12 (d, 2H), 7.64 (d, 2H).

REFERENCE EXAMPLE 24

1-Cyclopropyl-cyclopentano [b]-4-thiopyridone

The title compound was obtained in a manner similar to that in Reference Example 23 except that the 4H-pyran-4-on was replaced by cyclopentano [b] 4-pyrone.

NMR (DMSO-d$_6$) δ: 1.08 (m, 4H), 2.04 (m, 2H), 2.76 (t, 2H), 3.17 (t, 2H), 3.55 (m, 1H), 7.01 (d, 1H), 7.48 (d, 1H).

REFERENCE EXAMPLE 25

1-(2,2,2-Trifluoroethyl)-4-pyridone 1 g (10.4 mmol) of 4H-pyran-4-on was dissolved in 10 ml of pyridine, 3.38 g (25 mmol) of 2,2,2-trifluoroethylamine hydrochloride was added, and reacted at 70° C. for an hour. The solvent was removed, and the residue was purified by chloroform-methanol (10:1) silica gel chromatograph to obtain 1.7 g of the title compound.

NMR (DMSO-d$_6$) δ: 5.50–5.70 (2H ABq J=9 Hz), 7.45 (2H d J=8 Hz), 8.73 (2H d J=8 Hz).

1-(2,2,2-Trifluoroethyl)-4-pyridothione 1.7 g (9.6 mmol) of 1-(2,2,2-trifluoroethyl)-4-pyridone was dissolved in 17 ml of pyridine, 2.22 g (10 mmol) of P$_2$S$_5$ was added, and reacted at 50° C. for an hour. After the reaction, the solvent was removed, the residue was dissolved in chloroform, the pH was adjusted to 7.8 with an NaHCO$_3$ aqueous solution, and the mixture was washed with water and dried on magnesium sulfate. The solvent was removed, and the residue was purified by chloroform-methanol (20:1) silica gel chromatograph to obtain 890 mg of the title compound.

NMR (CDCl$_3$) δ: 4.36–4.55 (2H ABq J=8 Hz), 7.03 (2H d J=8 Hz), 7.33 (2H d J=8 Hz).

REFERENCE EXAMPLE 26

1-(2-Fluoroethyl)-4-pyridone 500 mg (5.2 mmol) of 4H-pyran-4-on was dissolved in 5 ml of pyridine, 1.54 g (15.5 mmol) of 2-fluoroethylamine hydrochloride was added, and reacted at 70° C. for 4 hours. The solvent was distilled off under reduced pressure, and the residue was purified by silica gel chromatography (chlroform-methanol (10:1)) to obtain 650 mg of the title compound.

NMR (90 MHz, D$_2$O) δ: 3.35 (2H, t, J=5 Hz), 3.65 (2H, t, J=5 Hz), 7.29 (2H, d, J=8 Hz), 8.48 (2H, d, J=8 Hz).

1-(2-Fluoroethyl)-4-pyridothione 350 mg (2.5 mmol) of 1-(2-fluoroethyl)-4-pyridone was dissolved in 3.5 ml of pyridine, 827 mg (3.75 mmol) of P$_2$S$_5$ was dissolved, and reacted at 55° C. for 3 hours. After the reaction, the formed precipitates were removed, and the filtrate was concentrated to dryness. This was purified by silica gel chromatography (chloroform-methanol (10:1)) to obtain 170 mg of the title compound.

NMR (90 MHz, CDCl$_3$) δ: 3.97 (1H, dd, J=5 Hz, 5 Hz), 4.25 (1H, dd, J=5 Hz, 5 Hz), 4.43 (1H, dd, J=5 Hz, 5 Hz), 4.95 (1H, dd, J=5 Hz, 5 Hz), 7.09 (2H, d, J=8 Hz), 7.38 (2H, d, J=8 Hz).

EXAMPLE 1

(6R,7R)-7-[(Z)-2-(2-Aminothiazol-4-yl)-2-methoxyiminoacetamido]-3-[(5,6-cyclopenteno-1-methyl-pyridinium-2-yl) thiomethyl]-ceph-3-em-4-carboxylate 240 mg of (6R,7R)-7-[(Z)-2-(2-aminothiazol-4-yl)-2-methoxyiminoacetamido]-3-acetoxymethyl-ceph-3-em-4-carboxylic acid sodium salt was dissolved in 1 ml of water and 1 ml of acetonitrile, then 210 mg of 1-methyl-cyclopentano [e] 2-thiopyridone and 750 mg of sodium iodide were added thereto, and were reacted at 70° C. for 4 hours while adjusting the pH of the reaction mixture to 6.5–7.0.

After the completion of the reaction, the reaction mixture was concentrated under reduced pressure, the insoluble matter was removed, acetone was added, the formed precipitates were filtered off, this was dissolved in a small quantity of water, and purified by Diaion HP-20 (Mitsubishi Chemical) column chromatography (eluted with 10% acetone-water). The fractions containing the desired product were concentrated, and freeze dried to obtain 40 mg of the title compound.

NMR (D$_2$O) δ: 2.32 (m, 2H), 3.16 (t, 2H), 3.36 (t, 2H), 3.67 (ABq, 2H), 4.02 (s, 3H), 4.22 (s, 3H), 4.27 (ABq, 2H), 5.18 (d, 1H), 5.74 (d, 1H), 7.03 (s, 1H), 7.75 (d, 1H), 8.07 (d, 1H).

Compounds of Examples 2-10 were obtained in a manner similar to that in Example 1 except that the 1-methyl-cyclopentano [e] 2-thiopyridone in Example 1 was replaced by various reagents (A) respectively.

EXAMPLE 2

(6R,7R)-7-[(Z)-2-(2-Aminothiazol-4-yl)-2-methoxyiminoacetamido]-3-[(2,3-cyclopenteno-1-methylpyridinium-4-yl)thiomethyl]-ceph-3-em-4-carboxylate (A) 1-Methyl-cyclopenteno [b]4-thiopyridone NMR (D$_2$O) δ: 2.29 (m, 2H), 2.96 (m, 2H), 3.24 (t, 2H), 3.62 (ABq, 2H), 3.99 (s, 3H), 4.04 (s, 3H), 4.28 (ABq, 2H), 5.18 (d, 1H), 5.73 (d, 1H), 6.92 (s, 1H), 7.64 (d, 1H), 8.17 (d, 1H).

EXAMPLE 3

(6R,7R)-7-[(Z)-2-(2-Aminothiazol-4-yl)-2-methoxyiminoacetamido]-3-[(5,6-cyclohexeno-1-methylpyridinium-2-yl)thiomethyl]-ceph-3-em-4-carboxylate (A) 1-Methyl-cyclohexano [e] 2-thiopyridone NMR (D$_2$O) δ: 1.80 (m, 2H), 1.97 (m, 2H), 2.90 (t, 2H), 3.04 (t, 2H), 3.65 (ABq, 2H), 4.00 (s, 3H), 4.14 (s, 3H), 4.30 (ABq, 2H), 5.18 (d, 1H), 5.73 (d, 1H), 6.97 (s, 1H), 7.74 (d, 1H), 7.96 (d, 1H).

EXAMPLE 4

(6R,7R)-7-[(Z)-2-(2-Aminothiazol-4-yl)-2-methoxyiminoacetamido]-3-[(6-methyl-2,3-cyclopenteno-1-methylpyridinium-4-yl)thiomethyl]-ceph-3-em-4-carboxylate (A) 1,6-Dimethyl-cyclopentano [b] 4-thiopyridone NMR (D$_2$O) δ: 2.36 (m, 2H), 2.64 (s, 3H), 2.94 (m, 2H), 3.25 (t, 2H), 3.62 (ABq, 2H), 3.91 (s, 3H), 4.00 (s, 3H), 4.29 (ABq, 2H), 5.18 (d, 1H), 5.72 (d, 1H), 6.90 (s, 1H), 7.56 (s, 1H).

EXAMPLE 5

(6R,7R)-7-[(Z)-2-(2-Aminothiazol-4-yl)-2-methoxyiminoacetamido]-3-[(6-methyl-2,3-cyclohexeno-1-methylpyridinium-4-yl)thiomethyl]-ceph-3-em-4-carboxylate (A) 1,6-Dimethyl-cyclohexeno [b] 4-thiopyridone NMR (D$_2$O) δ: 1.81 (m, 2H), 1.91 (m, 2H), 2.67 (s, 3H), 2.67 (t, 2H), 2.96 (t, 2H), 3.62 (ABq, 2H), 3.88 (s, 3H), 4.00 (s, 3H), 4.28 (ABq, 2H), 5.18 (d, 1H), 5.74 (d, 1H), 6.92 (s, 1H), 7.41 (s, 1H).

EXAMPLE 6

(6R,7R)-7-[(Z)-2-(2-Aminothiazol-4-yl)-2-methoxyiminoacetamido]-3-[(2,3-cyclopenteno-1-allylpyridinium-4-yl)thiomethyl]-ceph-3-em-4-carboxylate (A) 1-Allyl-cyclopentano [b] 4-thiopyridone NMR (D$_2$O) δ: 2.28 (m, 2H), 2.95 (m, 2H), 3.26 (t, 2H), 3.63 (ABq, 2H), 3.99 (s, 3H), 4.31 (ABq, 2H), 4.95 (d, 2H), 5.20 (d, 1H), 5.22 (d, 1H), 5.44 (d, 1H), 5.74 (d, 1H), 6.04 (m, 1H), 6.90 (s, 1H), 7.70 (d, 1H), 8.24 (d, 1H).

EXAMPLE 7

(6R,7R)-7-[(Z)-2-(2-Aminothiazol-4-yl)-2-methoxyiminoacetamido]-3-[(1-methylpyridinium-4-yl)thiomethyl]-ceph-3-em-4-carboxylate (A) 1-Methyl-4-thiopyridone NMR (D$_2$O) δ: 3.62 (ABq, 2H), 4.01 (s, 3H), 4.21 (s, 3H), 4.31 (ABq, 2H), 5.20 (d, 1H), 5.79 (d, 1H), 7.01 (s, 1H), 7.81 (d, 2H), 8.40 (d, 2H).

EXAMPLE 8

(6R,7R)-7-[(Z)-2-(2-Aminothiazol-4-yl)-2-methoxyiminoacetamido]-3-[(1-methylpyridinium-2-yl)thiomethyl]-ceph-3-em-4-carboxylate (A) 1-Methyl-2-thiopyridone NMR (D$_2$O) δ: 3.65 (ABq, 2H), 4.01 (s, 3H), 4.31 (s, 3H), 4.37 (ABq, 2H), 5.23 (d, 1H), 5.78 (d, 1H), 7.03 (s, 1H), 7.76 (m, 1H), 8.05 (d, 1H), 8.30 (m, 1H), 8.78 (d, 1H).

EXAMPLE 9

(6R,7R)-7-[(Z)-2-(2-Aminothiazol-4-yl)-2-methoxyiminoacetamido]-3-[(1-allylpyridinium-2-yl)thiomethyl]-ceph-3-em-4-carboxylate (A) 1-Allyl-2-thiopyridone NMR (D$_2$O) δ: 3.63 (ABq, 2H), 4.01 (s, 3H), 4.33 (ABq, 2H), 5.20 (d, 1H), 5.25-5.75 (m, 4H), 5.77 (d, 1H), 6.09 (m, 1H), 7.03 (s, 1H), 7.89 (m, 1H), 8.10 (d, 1H), 8.47 (m, 1H), 8.83 (d, 1H).

EXAMPLE 10

(6R,7R)-7-[(Z)-2-(2-Aminothiazol-4-yl)-2-methoxyiminoacetamido]-3-[(5-methyl-2,3-cyclopenteno-1-methylpyridinium-4-yl)thiomethyl]-ceph-3-em-4-carboxylate (A) 1,5-Dimethyl-cyclopentano [b]-4-thiopyridone NMR (D$_2$O) δ: 2.32 (m, 2H), 2.54 (s, 3H), 3.23 (m, 2H), 3.22 (t, 2H), 3.70 (ABq, 2H), 4.02 (s, 3H), 4.13 (s, 3H), 4.10 (ABq, 2H), 5.16 (d, 1H), 5.74 (d, 1H), 7.02 (s, 1H), 8.26 (s, 1H).

EXAMPLE 11

(6R,7R)-7-[(Z)-2-(2-Aminothiazol-4-yl)-2-(3DL-3-amino-3-carboxypropyloxyimino)acetamido]-3-[(5,6-cyclohexeno-1-methylpyridinium-2-yl)thiomethyl]-ceph-3-em-4-carboxylate (a) 11.9 g of DL-homoserine was dissolved in 200 ml of water, and 10 g of Na$_2$CO$_3$ and 150 ml of dioxane were added thereto. 50 ml of a dioxane solution containing 27.5 g of di-t-butyl dicarbonate was added dropwise thereto over an hour. Thereafter, a reaction was effected at room temperature for 2 hours. After completion of the reaction, the dioxane was removed under reduced pressure, the residue was washed with ethyl acetate, and, after adjusting the pH to 2 with 5N hydrochloric acid with ice cooling, extracted twice with 400 ml of ethyl acetate. The ethyl acetate layer was washed with saturated saline, dried on magnesium sulfate, and concentrated to dryness to obtain 18.5 g of N-t-butoxycarbonyl DL-homoserine.

6 g of the obtained N-t-butoxycarbonyl DL-homoserine was dissolved in 100 ml of methylene chloride, and 50 ml of a methylene chloride solution containing 6 g of diphenyldiazomethane was added dropwise thereto over an hour. After completion of the reaction, the reaction mixture was concentrated to a small volume, and petroleum ether was added thereto. The formed crystals were filtered off to obtain 8.6 g of N-t-butoxycarbonyl DL-homoserine benzhydryl ester.

(b) 6.75 g of the N-t-butoxycarbonyl DL-homoserine benzhydryl ester was dissolved in 150 ml of dry tetrahydrofuran, then 2.85 g of N-hydroxyphthalimide and 4.6 g of triphenylphosphine were added followed by 2.75 ml of diethyl azodicarboxylate, and a reaction was effected at room temperature under argon atmosphere for 3 hours.

After the completion of the reaction, the reaction mixture was concentrated under reduced pressure, and dissolved in 30 ml of ether.

The formed crystals were filtered off to obtain 7 g of N-t-butoxycarbonyl-O-phthalimido-DL-homoserine benzhydryl ester.

NMR (CDCl$_3$) δ: 1.44 (s, 9H), 2.33 (m, 2H), 4.27 (t, 2H), 4.68 (m, 1H), 5.79 (d, 1H), 6.93 (s, 1H), 7.34 (m, 10H), 7.81 (m, 4H).

(c) 5.52 g of the N-t-butoxycarbonyl-O-phthalimido-DL-homoserine-benzhydryl ester was dissolved in 100 ml of dry methylene chloride, 0.51 ml of hydrous hydrazine was added thereto, and reacted with ice cooling for an hour. Further, 0.12 ml of hydrazine was added, and reacted at the same temperature for an hour. After the completion of the reaction, the insoluble matter was removed by filtration, the filtrate was washed successively with water and ammonia water, dried on magnesium sulfate, and concentrated to dryness under reduced pressure.

The residue was dissolved in 700 ml of ether, the formed crystals were removed by filtration, the filtrate was concentrated, the further formed crystals were removed by filtration, and the filtrate was concentrated to dryness to obtain 3.88 g of N-t-butoxycarbonyl-O-amino-DL-homoserine benzhydryl ester.

NMR (CDCl$_3$) δ: 1.43 (s, 9H), 2.08 (m, 2H), 3.68 (t, 2H), 4.53 (m, 1H), 5.27 (m, 2H), 6.93 (s, 1H), 7.35 (m, 10H).

(d) 1.71 g of (2-chloroacetylamino-thiazol-4-yl)glyoxylic acid and was dissolved in 30 ml of a 1:2 mixed solution of tetrahydrofuran-water, 30 ml of a tetrahydrofuran solution containing 2.88 g of the N-t-butoxycarbonyl-O-amino-DL-homoserine benzhydryl ester was added thereto, and, after adjusting the pH to 5.1 with 1N sodium hydroxide, reacted at room temperature for 6 hours. After the completion of the reaction, the pH of the reaction mixture was adjusted to 6.5, and this was concentrated under reduced pressure to remove the tetrahydrofuran. 100 ml of water was added, the pH of the solution was adjusted to 8, then this was washed with 100 ml of ether, and, after adjusting the pH to 2 with 2N hydrochloric acid, extracted with 250 ml of ethyl acetate. The ethyl acetate layer was washed with water, dried on magnesium sulfate, and concentrated under reduced pressure. The residue was dissolved in 100 ml of ether, and the insoluble matter was removed by filtration to obtain 3.15 g of (Z)-2-(2-chloroacetylamino-thiazol-4-yl)-2-(3DL-3-t-butoxycarbonylamino-3-diphenylmethoxycarbonyl)propyloxyiminoacetic acid.

NMR (acetone-d$_6$) δ: 1.48 (s, 9H), 2.28 (m, 2H), 4.30 (t, 2H), 4.57 (m, 1H), 4.50 (s, 2H), 6.88 (s, 1H), 7.36 (m, 10H), 7.56 (s, 1H).

(e) 1.4 g of the (Z)-2-(2-chloroacetylamino-thiazol-4-yl)-2-(3DL-t-butoxycarbonylamino-3-diphenylmethoxycarbonyl)propyloxyiminoacetic acid was dissolved in 15 ml of N,N-dimethylformamide, 300 mg of N-hydroxybenztriazole and 465 mg of N,N-dicyclohexylcarbodimide were added, and reacted at room temperature for an hour. 985 mg of 7-amino-3-acetoxymethyl-ceph-3-em-4-carboxylic acid benzhydryl ester was added thereto with ice cooling, and reacted at the same temperature for 5 hours.

After completion of the reaction, the insoluble matter was removed by filtration, 150 ml of methylene chloride was added, the solution was washed successively with dilute hydrochloric acid and water, dried on magnesium sulfate, and concentrated to dryness under reduced pressure.

This was purified by silica gel chromatography (developing solvent: benzene-ethyl acetate 5:2) to obtain 1.35 g of (6R,7R)-7-[(Z)-2-chloroacetylaminothiazol-4-yl)-2-(3DL-3-t-butoxycarbonylamino-3-diphenylmethoxycarbonylpropyloxyimino)acetamido]-3-acetoxymethyl-ceph-3-em-4-carboxylic acid benzhydryl ester.

(f) This was dissolved in 12 ml of anisole, 12 ml of trifluoroacetic acid was added thereto with ice cooling, and reacted at the same temperature for 1.5 hours. After the completion of the reaction, the trifluoroacetic acid was removed under reduced pressure, the residue was poured into 150 ml of hexane cooled to −20° C.-−30° C., 70 ml of ether was added thereto, and the supernatant was removed. The residue was washed with ether, and the precipitates were filtered off to obtain 750 mg of (6R,7R)-7-[(Z)-2-(2-chloroacetylamino-thiazol-4-yl)-2-(3DL-3-amino-5-carboxypropyloxyimino)acetamido]-3-acetoxymethyl-ceph-3-em-4-carboxylic acid trifluoracetate.

This was suspended in 75 ml of water, the pH was adjusted to 6.5 with a saturated sodium bicarbonate aqueous solution, 200 mg of sodium N-methyl-dithiocarbamate was added, and reacted at room temperature for 3 hours. After the completion of the reaction, the reaction mixture was washed with ethyl acetate, purified by HP-20 column chromatography, the fractions containing the desired product were concentrated, and freeze dried to obtain 400 mg of (6R,7R)-7-[(Z)-2-(2-aminothiazol-4-yl)-2-(3DL-3-amino-3-carboxypropyloxyimino)acetamido]-3-acetoxymethyl-ceph-3-em-4-carboxylate.

NMR (D$_2$O) δ from the external standard TMS: 2.06 (s, 3H), 2.09 (m, 2H), 3.51 (ABq, 2H), 4.09 (m, 1H), 4.58 (m, 2H), 4.77 (ABq, 2H), 5.20 (d, 1H), 5.79 (d, 1H), 7.06 (s, 1H).

(g) 270 mg of the compound from (f) was dissolved in 1.6 ml of water and 1.6 ml of acetonitrile, 750 mg of sodium iodide and 224 mg of 1-methyl-cyclohexano[e]-2-thiopyridone were added, and reacted at 65° C. for 4 hours while adjusting the pH of the reaction mixture to 6.5-7.0.

After completion of the reaction, the reaction mixture was concentrated under reduced pressure to remove the acetonitrile, 20 ml of acetone was added, the formed precipitates were filtered off, washed thoroughly with acetone, dissolved in a small quantity of water, and purified by Diaion HP-20 chromatography. The fractions containing the desired product were concentrated and freeze dried to obtain 65 mg of the title compound.

NMR (D$_2$O) δ: 1.80 (m, 2H), 1.98 (m, 2H), 2.92 (t, 2H), 3.03 (t, 2H), 2.25 (m, 2H), 3.63 (ABq, 2H), 4.05 (m, 1H), 4.13 (s, 3H), 4.35 (ABq, 2H), 4.60 (m, 2H), 5.17 (d, 1H), 5.74 (d, 1H), 7.03 (s, 1H), 7.73 (d, 1H), 7.96 (d, 1H).

EXAMPLE 12

(6R,7R)-7-[(Z)-2-(2-Aminothiazol-4-yl)-2-(2D-2-amino-2-carboxyethoxyimino)acetamido]-3-[(6-methyl-2,3-cyclohexeno-1-methylpyridinium-4-yl)thiomethyl]-ceph-3-em-4-carboxylate (a) 2 g of D-cycloserine was dissolved in 11 ml of 50% conc. hydrochloric acid, and acid hydrolyzed at 60° C. for 3 hours. After the completion of the reaction, the reaction mixture was concentrated under reduced pressure, azeotropically distilled with ethanol several times, and dried under reduced pressure overnight to obtain β-aminoxy-D-alanine dihydrochloride. This was dissolved in 100 ml of ethanol, and 80 ml of an ethanol solution containing 9.5 g of diphenyldiazomethane was added dropwise at 5°–10° C. over 2.5 hours. After the completion of the reaction, the reaction mixture was concentrated to a small quantity, and 60 ml of ether and 80 ml of hexane were added thereto. The supernatant was removed, and the residue was crystallized from ethanol-water to obtain 5.5 g of β-aminoxy-D-alanine benzhydryl ester dihydrochloride.

(b) 1.86 g of (2-chloroacetylaminothiazol-4-yl)glyoxylic acid was dissolved in 75 ml of 2:1 mixed solution of tetrahydrofuran and water, 2.96 g of the β-aminoxy-D-alanine benzhydryl ester dihydrochloride obtained in (a) was added thereto with ice cooling, the pH of the reaction mixture was adjusted to 5 with a saturated sodium bicarbonate aqueous solution, and a reaction was effected at room temperature for 3 hours. Thereafter, the pH of the reaction mixture was adjusted to 8.5 to dissolve the formed crystals, 20 ml of a tetrahydrofuran solution containing 2.15 g of di-t-butyl dicarbonate was added, and reacted at room temperature for 4.5 hours.

After the completion of the reaction, the tetrahydrofuran was removed under reduced pressure, the pH was adjusted to 2 with 5N hydrochloric acid with cooling, this was then extracted twice with 200 ml of ethyl acetate, the ethyl acetate layer was washed with saturated saline, dried on magnesium sulfate anhydride, and concentrated to dryness under reduced pressure. This was crystallized from ethyl acetate-petroleum ether to obtain 3.6 g of (Z)-2-(2-chloroacetylaminothiazol-4-yl)2-(2D-2-t-butoxycarbonylamino-2-diphenylmethoxycarbonyl)ethoxyiminoacetic acid.

(c) 2.5 g of the (Z)-2-(2-chloroacetylaminothiazol-4-yl)-2-(2D-2-t-butoxycarbonylamino-2-diphenylmethoxycarbonyl)ethoxyiminoacetic acid and 1.75 g of 7-amino-3-acetoxymethyl-ceph-3-em-4-carboxylic acid benzhydryl ester were treated in a manner similar to that in Example 11 (e) and (f) to obtain 970 mg of (6R,7R)-7-[(Z)-2-(2-aminothiazol-4-yl)-2-(2D-2-amino-2-carboxyethoxyimino)acetamido]-3-acetoxymethyl-ceph-3-em-4-carboxylate.

NMR (D$_2$O, δ from the external standard TMS): 2.06 (s, 3H), 3.51 (ABq, 2H), 4.12 (dd, 1H), 4.60 (m, 2H), 4.77 (ABq, 2H), 5.19 (d, 1H), 5.79 (d, 1H), 7.05 (s, 1H).

(d) 260 mg of this was dissolved in 1.5 ml of water and 1.5 ml of acetonitrile, 750 ml of sodium iodide and 230 mg of 1,6-dimethyl-cyclohexano [b] 4-thiopyridone were added, and reacted at 65° C. for 4 hours while maintaining the pH of the reaction mixture at 6.5–7.0. After completion of the reaction, the reaction mixture was treated in a manner similar to that in Example 11 (g) to obtain 95 mg of the title compound.

NMR (D$_2$O) δ: 1.82 (m, 2H), 1.72 (m, 2H), 2.68 (s, 3H), 2.68 (t, 2H), 2.96 (t, 2H), 3.63 (ABq, 2H), 3.89 (s, 3H), 4.02 (m, 1H), 4.29 (ABq, 2H), 4.56 (m, 2H), 5.19 (d, 1H), 5.77 (d, 1H), 7.00 (s, 1H), 7.56 (s, 1H).

Compounds of Examples 13–16 were obtained in a manner similar to that in Example 12 (d) except that the 1,6-dimethyl-cyclohexano [b] 4-thiopyridone was replaced by various reagents (A).

EXAMPLE 13

(6R,7R)-7-[(Z)-2-(2-Aminothiazol-4-yl)-2-(2D-2-amino-2-carboxyethoxyimino)acetamido]-3-[(5,6-cyclohexeno-1-methylpyridinium-2-yl)thiomethyl]-ceph-3-em-4-carboxylate (A) 1-Methyl-cyclohexano [e]-2-thiopyridon NMR (D$_2$O) δ: 1.80 (m, 2H), 1.98 (m, 2H), 2.90 (t, 2H), 3.05 (t, 2H), 3.62 (ABq, 2H), 4.08 (m, 1H), 4.13 (s, 3H), 4.31 (ABq, 2H), 4.55 (m, 2H), 5.20 (d, 1H), 5.75 (d, 1H), 7.03 (s, 1H), 7.75 (d, 1H), 7.97 (d, 1H).

EXAMPLE 14

(6R,7R)-7-[(Z)-2-(2-Aminothiazol-4-yl)-2-(2D-2-amino-2-carboxyethoxyimino)acetamido]-3-[(6-methyl-2,3-cyclopenteno-1-methylpyridinium-4-yl)thiomethyl]-ceph-3-em-4-carboxylate (A) 1,6-Dimethyl-cyclopentano [b]-4-thiopyridon NMR (D$_2$O) δ: 2.33 (m, 2H), 2.67 (s, 3H), 2.97 (t, 2H), 3.25 (t, 2H), 3.63 (ABq, 2H), 3.91 (s, 3H), 4.05 (m, 1H), 4.31 (ABq, 2H), 4.55 (m, 2H), 5.20 (d, 1H), 5.75 (d, 1H), 6.98 (s, 1H), 7.58 (s, 1H).

EXAMPLE 15

(6R,7R)-7-[(Z)-2-(2-Aminothiazol-4-yl)-2-(2D-2-amino-2-carboxyethoxyimino)acetamido]-3-[(1-allyl-pyridinium-2-yl)thiomethyl]-ceph-3-em-4-carboxylate (A) 1-Allyl-2-thiopyridon NMR (D$_2$O, δ from the external standard TMS): 3.58 (ABq, 2H), 4.12 (m, 1H), 4.36 (ABq, 2H), 4.59 (m, 2H), 5.0–5.6 (m, 5H), 5.73 (d, 1H), 6.00 (m, 1H), 7.02 (s, 1H), 7.72 (m, 1H), 7.94 (d, 1H), 8.30 (m, 1H), 8.67 (d, 1H).

EXAMPLE 16

(6R,7R)-7-[(Z)-2-(2-Aminothiazol-4-yl)-2-(2D-2-amino-2-carboxyethoxyimino)acetamido]-3-[(1-methyl-pyridinium-4-yl)thiomethyl]-ceph-3-em-4-carboxylate (A) 1-Methyl-4-thiopyridon NMR (D$_2$O, δ from the external standard TMS): 3.56 (ABq, 2H), 4.10 (dd, 1H), 4.14 (s, 3H), 4.21 (ABq, 2H), 4.60 (m, 2H), 5.12 (d, 1H), 5.72 (d, 1H), 6.97 (s, 1H), 7.71 (d, 2H), 8.31 (d, 2H).

EXAMPLE 17

(6R,7R)-7-[(Z)-2-(2-Aminothiazol-4-yl)-2-(1-methyl-1-carboxyethoxyimino)acetamido]-3-[(5,6-cyclopenteno-1-methylpyridinium-2-yl)thiomethyl]-ceph-3-em-4-carboxylate (6R,7A)-7-[(Z)-2-(2-Aminothiazol-4-yl)-2-(1-methyl-1-carboxyethoxyimino)acetamido]-3-acetoxymethyl-ceph-3-em-4-carboxylic acid sodium salt [prepared from (Z)-2-(2-chloroacetylaminothiazol-4-yl)-2-(1-methyl-1-diphenylmethoxycarbonyl)ethoxyiminoacetic acid and 7-amino-3-acetoxymethyl-ceph-3-em-4-carboxylic acid benzhydryl ester in a manner similar to that in Example 11 (e) and (f)]

220 mg of the above sodium salt was dissolved in 1.6 ml of water and 1.6 ml of acetonitrile, 600 mg of sodium iodide and 150 mg of 1-methyl-cyclopentano [e] 2-thiopyridone were added, and reacted at 65° C. for 6 hours while maintaining the pH of the reaction mixture at 6.5–7.0. After the completion of the reaction, the reaction mixture was treated in a manner similar to that in Example 11 (g) to obtain 65 mg of the title compound.

NMR (D₂O) δ: 1.53 (s, 3H), 1.55 (s, 3H), 2.33 (m, 2H), 3.17 (t, 2H), 3.38 (t, 2H), 3.69 (ABq, 2H), 4.24 (s, 3H), 4.27 (ABq, 2H), 5.20 (d, 1H), 5.77 (d, 1H), 6.99 (s, 1H), 7.78 (d, 1H), 8.10 (d, 1H).

Compounds of Examples 18–21 were obtained in a manner similar to that in Example 17 except that the 1-methyl-cyclopentano [e] 2-thiopyridone was replaced by various reagents (A).

EXAMPLE 18

(6R,7R)-7-[(Z)-2-(2-Aminothiazol-4-yl)-2-(1-methyl-1-carboxyethoxyimino)acetamido]-3-[(5,6-cyclohexeno-1-methylpyridinium-2-yl)thiomethyl]-ceph-3-em-4-carboxylate (A) 1-Methyl-cyclohexano [e] 2-thiopyridone NMR (D₂O) δ: 1.49 (s, 3H), 1.50 (s, 3H), 1.78 (m, 2H), 1.95 (m, 2H), 2.90 (t, 2H), 3.04 (t, 2H), 3.64 (ABq, 2H), 4.16 (s, 3H), 4.28 (ABq, 2H), 5.16 (d, 1H), 5.75 (d, 1H), 6.96 (s, 1H), 7.74 (d, 1H), 7.97 (d, 1H).

EXAMPLE 19

(6R,7R)-7-[(Z)-2-(2-Aminothiazol-4-yl)-2-(1-methyl-1-carboxyethoxyimino)acetamido]-3-[(2,3-cyclopenteno-1-methylpyridinium-4-yl)thiomethyl]-ceph-3-em-4-carboxylate (A) 1-Methyl-cyclopentano [b] 4-thiopyridone NMR (D₂O) δ: 1.48 (s, 3H), 1.50 (s, 3H), 2.28 (m, 2H), 2.97 (m, 2H), 3.25 (t, 2H), 3.61 (ABq, 2H), 4.04 (s, 3H), 4.30 (ABq, 2H), 5.18 (d, 1H), 5.76 (d, 1H), 6.91 (s, 1H), 7.64 (d, 1H), 8.17 (d, 1H).

EXAMPLE 20

(6R,7R)-7-[(Z)-2-(2-Aminothiazol-4-yl)-2-(1-methyl-1-carboxyethoxyimino)acetamido]-3-[(6-methyl-2,3-cyclopenteno-1-methylpyridinium-4-yl)thiomethyl]-ceph-3-em-4-carboxylate (A) 1,6-Dimethyl-cyclopentano [b] 4-thiopyridone NMR (D₂O) δ: 1.50 (s, 3H), 1.51 (s, 3H), 2.30 (m, 2H), 2.66 (s, 3H), 2.98 (t, 2H), 3.28 (t, 2H), 3.63 (ABq, 2H), 3.93 (s, 3H), 4.33 (ABq, 2H), 5.20 (d, 1H), 5.77 (d, 1H), 6.94 (s, 1H), 7.44 (s, 1H).

EXAMPLE 21

(6R,7R)-7-[(Z)-2-(2-Aminothiazol-4-yl)-2-(1-methyl-1-carboxyethoxyimino)acetamido]-3-[(6-methyl-2,3-cyclohexeno-1-methylpyridinium-4-yl)thiomethyl]-ceph-3-em-4-carboxylate (A) 1,6-Dimethyl-cyclohexano [b] 4-thiopyridone NMR (D₂O) δ: 1.47 (s, 3H), 1.48 (s, 3H), 1.81 (m, 2H), 1.90 (m, 2H), 2.66 (s, 3H), 2.68 (t, 2H), 2.94 (t, 2H), 3.59 (ABq, 2H), 3.86 (s, 3H), 4.29 (ABq, 2H), 5.17 (d, 1H), 5.74 (d, 1H), 6.90 (s, 1H), 7.58 (s, 1H).

EXAMPLE 22

(6R,7R)-7-[(Z)-2-(2-Aminothiazol-4-yl)-2-methoxyiminoacetamido]-3-[(5,6-cyclopenteno-1-methylpyridinium-2-yl)thiomethyl]-ceph-3-em-4-carboxylate 230 mg of (6R,7R)-7-[(Z)-2-(2-Aminothiazol-4-yl)-2-methoxyiminoacetamido]-3-acetoxymethyl-ceph-3-em-4-carboxylic acid was suspended in a 2 ml of anhydrous dichloromethane, then, under argon atmosphere, 0.27 ml of N,O-bistrimethylsilyltrifluoroacetamide was added and reacted at room temperature for 1.5 hours. 0.22 ml of trimethylsilyl iodide was added thereto and further reacted at room temperature for 45 minutes.

Thereafter, the reaction mixture was concentrated under reduced pressure, the residue was dissolved in 1.6 ml of anhydrous acetonitrile, and 0.1 ml of anhydrous tetrahydrofuran was added. Five minutes later, 100 mg of 1-methyl-cyclopentano [e] 2-thiopyridine dissolved in 0.5 ml of anhydrous dichloromethane was added, and reacted at room temperature for 1.5 hours.

After the completion of the reaction, 0.1 ml of water was added with cooling, the formed precipitates were filtered off, washed thoroughly with a mixed solution of acetonitrile-ether, dried, then suspended in a small quantity of water, and further dissolved by making the pH 7.5 with a saturated sodium bicarbonate aqueous solution. This was purified by Diaion HP-20 column chromatography, the fractions containing the desired product were concentrated, and freeze dried to obtain 70 mg of the title compound. This compound had the identical spectral data as those of the compound obtained in Example 1.

EXAMPLE 23

(6R,7R)-7-[(Z)-2-(2-Aminothiazol-4-yl)-2-methoxyiminoacetamido]-3-[(5,6-cyclohexeno-1-methylpyridinium-2-yl)thiomethyl]-ceph-3-em-4-carboxylate 400 mg of (Z)-2-(2-aminothiazol-4-yl)-2-methoxyiminoacetic acid was dissolved in 4 ml of N,N-dimethylformamide, 270 mg of N-hydroxybenztriazole and 415 mg of N,N'-dicyclohexylcarbodimide were added thereto, and reacted at room temperature for an hour.

Separately, 790 mg of 7-amino-3-(5,6-cyclohexeno-1-methylpyridinium-2-yl)thiomethyl-ceph-3-em-4-carboxylate was suspended in 5 ml of N,N-dimethylformamide, then, with ice cooling, 0.45 ml of triethylamine was added followed by the above reaction mixture, and reacted at 5° C. overnight.

After the completion of the reaction, the insoluble matter was removed by filtration, ether was added, and the formed precipitates were filtered off. They were washed thoroughly with ethyl acetate, then dissolved in a small quantity of water, and, after adjusting the pH to 6.5, purified by Diaion HP-20 column chromatography. The fractions containing the desired product were concentrated and freeze dried to obtain the title compound. The spectral data of this product were identical to those of Example 3.

EXAMPLE 24

(6R,7R)-7-[(Z)-2-(2-Aminothiazol-4-yl)-2-(carboxymethoxyimino)acetamido]-3-[(6-methyl-2,3-cyclopenteno-1-methylpyridinium-4-yl)thiomethyl]-ceph-3-em-4-carboxylate 250 mg of (6R,7R)-7-[(Z)-2-(2-aminothiazol-4-yl)-2-(carboxymethoxyimino)acetamido]-3-acetoxymethyl-ceph-3-em-4-carboxylic acid sodium salt [prepared from (Z)-(2-chloroacetylaminothiazol-4-yl)-2-t-butoxycarbonylmethoxyiminoacetic acid and 7-amino-3-acetoxymethyl-ceph-3-em-4-carboxylic acid benzhydryl ester in a manner similar to that in Example 11 (e) and (f)] was dissolved in 1.5 ml of water and 1.5 ml of acetonitrile, 750 mg of sodium iodide and 200 mg of 1,6-dimethylcyclopentano [b] 4-thiopyridone were added thereto, and reacted at 70° C. for 3 hours. During the reaction, the pH of the reaction mixture was adjusted to 6.5–7.0.

After the completion of the reaction, the reaction mixture was treated in a manner similar to that in Example 1 to obtain 80 mg of the title compound.

NMR (D$_2$O) δ: 2.35 (m, 2H), 2.66 (s, 3H), 2.95 (m, 2H), 3.27 (t, 2H), 3.63 (ABq, 2H), 3.93 (s, 3H), 4.74 (s, 2H), 4.33 (ABq, 2H), 5.20 (d, 1H), 5.76 (d, 1H), 6.95 (s, 1H), 7.59 (s, 1H).

EXAMPLE 25

(6R,7R)-7-[(Z)-2-(2-Aminothiazol-4-yl)-2-(carboxymethoxyimino)acetamido]-3-[(5,6-cyclohexeno-1-methylpyridinium-2-yl)thiomethyl]-ceph-3-em-4-carboxylate The title compound was obtained in a manner similar to that in Example 24 except that the 1,6-dimethylcyclopentano [b] 4-thiopyridone was replaced by 1-methylcyclohexano [e] 2-thiopyridone.

NMR (D$_2$O) δ: 1.80 (m, 2H), 1.97 (m, 2H), 2.91 (t, 2H), 3.05 (t, 2H), 3.67 (ABq, 2H), 4.16 (s, 3H), 4.29 (ABq, 2H), 4.73 (s, 2H), 5.20 (d, 1H), 5.75 (d, 1H), 6.99 (s, 1H), 7.74 (d, 1H), 7.97 (d, 1H).

EXAMPLE 26

(6R,7R)-7-[(Z)-2-(2-Aminothiazol-4-yl)-2-ethoxyiminoacetamido]-3-[(5,6-cyclopenteno-1-methylpyridinium-2-yl)thiomethyl]-ceph-3-em-4-carboxylate (6R,7R)-7-[(Z)-2-(2-aminothiazol-4-yl)-2-ethoxyiminoacetamido]-3-acetoxymethyl-ceph-3-em-4-carboxylic acid sodium salt and 1-methyl-cyclopentano [e] 2-thiopyridone were treated in a manner similar to that in Example 1 to obtain the title compound.

NMR (D$_2$O) δ: 1.45 (t, 3H), 2.33 (m, 2H), 3.17 (t, 2H), 3.36 (t, 2H), 3.65 (ABq, 2H), 4.22 (s, 3H), 4.27 (ABq, 2H), 4.55 (ABq, 2H), 5.18 (d, 1H), 5.73 (d, 1H), 7.02 (s, 1H), 7.79 (d, 1H), 8.09 (d, 1H).

EXAMPLE 27

(6R,7R)-7-[(Z)-2-(2-Aminothiazol-4-yl)-2-methoxyiminoacetamido]-3-[(1-carboxymethylpyridinium-4-yl)thiomethyl]-ceph-3-em-4-carboxylic acid sodium salt 120 mg (0.24 mmol) of diphenylmethyl (6R,7R)-7-amino-3-bromomethyl-ceph-3-em-4-carboxylate hydrochloride and 120 mg (0.27 mmol) of (Z)-2-(2-tritylaminothiazol-4-yl)-2-methoxyiminoacetic acid were dissolved in 2.4 ml of methylene chloride. 98 μl (1.2 mmol) of pyridine and 24 μl (0.27 mmol) of phosphorus oxychloride were added with ice cooling, and reacted for 10 minutes.

After the reaction, 12 ml of chloroform was added, the reaction mixture was washed twice with 6 ml of water, dried on magnesium sulfate, and the solvent was removed. The residue was purified by silica gel chromatography using benzene-ethyl acetate (20:1) to obtain 190 mg of diphenylmethyl (6R,7R)-3-bromomethyl-7-[(Z)-2-(2-tritylaminothiazol-4-yl)-2-methoxyiminoacetamido]-ceph-3-em-4-carboxylate (yield 90%).

NMR (CDCl$_3$) δ: 3.55 (2H, bs), 4.05 (3H, s), 4.35 (2H, bs), 5.05 (1H, d, J=4), 5.90 (1H, dd, J=4, J=8), 6.75 (1H, s), 6.95 (1H, s), 7.1–7.8 (26H, m).

89 mg (0.1 mmol) of the diphenylmethyl (6R,7R)-3-bromomethyl-7-[(Z)-2-(2-tritylaminothiazol-4-yl)-2-methoxyiminoacetamido]-ceph-3-em-4-carboxylate was dissolved in 0.89 ml of DMF, 37 mg (0.11 mmol) of 1-diphenylmethoxycarbonylmethyl-4-pyridothione was added, and reacted at room temperature for an hour. After the reaction, 5 ml of ethyl acetate was added, the reaction mixture was washed with 3 ml of 0.1N-HCl, then washed with water, dried on magnesium sulfate, and the solvent was removed to obtain 120 mg of diphenylmethyl (6R,7R)-7-[(Z)-2-(2-tritylaminothiazol-4-yl)-2-methoxyiminoacetamido]-3-[(1-diphenylmethoxycarbonylmethylpyridinium-4-yl)thiomethyl]-ceph-3-em-4-carboxylate bromide, which was used in the next reaction without purification.

120 mg of the diphenylmethyl (6R,7R)-7-[2-(2-tritylaminothiazol-4-yl)-2-methoxyiminoacetamido]-3-[(1-diphenylmethoxycarbonylmethylpyridinium-4-yl)thiomethyl]-ceph-3-em-4-carboxylate was dissolved in 360 μl of anisole, 1.2 ml of trifluoroacetic acid was added with ice cooling, and reacted for 40 minutes. After the reaction, isopropyl ether was added to form precipitates. They were dried to obtain 61 mg of a powder, and, after adding 1.8 ml of water and adjusting the pH to 7.8 with NaHCO$_3$, purified with Diaion HP-20 resin (methanol:H$_2$O=1:4) to obtain 30 mg of the title compound.

NMR (D$_2$O) δ: 3.40, 3.75 (2H, ABq, J=16), 3.95 (3H, s), 4.15, 4.45 (2H, ABq, J=12), 5.00 (2H, s), 5.15 (1H, d, J=4), 5.70 (1H, d, J=4), 6.95 (1H, s), 7.25 (2H, d, J=8), 8.30 (2H, d, J=8).

EXAMPLE 28

(6R,7R)-7-[(Z)-2-(2-Aminothiazol-4-yl)-2-ethoxyiminoacetamido]-3-[(1-carboxymethylpyridinium-4-yl)thiomethyl]-ceph-3-em-4-carboxylic acid sodium salt 460 mg (0.51 mmol) of the 3-bromomethyl form synthesized in a manner similar to that in Example 27 was dissolved in 4.6 ml of DMF, 258 mg (0.77 mmol) of 1-diphenylmethoxycarbonylmethyl-4-pyridothion was added, and reacted at room temperature for an hour. After the reaction, 25 ml of ethyl acetate was added, the reaction mixture was washed with 15 ml of 0.1N-HCl, then washed with water, dried on magnesium sulfate, and the solvent was removed to obtain 710 mg of diphenylmethyl (6R,7R)-7-[(Z)-2-(2-tritylaminothiazol-4-yl)-2-ethoxyiminoacetamido]-3-[(1-diphenylmethoxycarbonylmethylpyridinium-4-yl)thiomethyl]-ceph-3-em-4-carboxylate bromide, which was used in the next reaction without purification.

710 mg of the diphenylmethyl (6R,7R)-7-[(Z)-2-(2-tritylaminothiazol-4-yl)-2-ethoxyiminoacetamido]-3-[(1-diphenylmethoxycarbonylmethylpyridinium-4-yl)thiomethyl]-ceph-3-em-4-carboxylate bromide was dissolved in 2.13 ml of anisole, 7.1 ml of trifluoroacetic acid was added with ice cooling, and reacted for 40 minutes. After the reaction, isopropyl ether was added to form precipitates. They were dried to obtain 440 mg of a powder, and, after adding 13 ml of water and adjusting the pH to 7.8 with NaHCO$_3$, purified with Diaion HP-20 resin (methanol:H$_2$O=1:4) to obtain 240 mg of the title compound.

NMR (D$_2$O) δ: 1.25 (3H, t, J=6), 3.35, 3.70 (2H, ABq, J=20), 4.20 (2H, q, J=6), 4.10, 4.40 (2H, ABq, J=12), 4.95 (2H, s), 5.15 (1H, d, J=4), 5.75 (1H, d, J=4), 6.90 (1H, s), 7.75 (2H, d, J=8), 8.30 (2H, d, J=8).

EXAMPLE 29

(6R,7R)-7-[(Z)-2-(2-Aminothiazol-4-yl)-2-(carboxymethoxyimino)acetamido]-3-[(1-carboxymethylpyridinium-4-yl)thiomethyl]-ceph-3-em-4-carboxylic acid sodium salt 160 mg (0.15 mmol) of the 3-bromomethyl form synthesized in a manner similar to that in Example 27 was dissolved in 1.6 ml of DMF, 55 mg (0.165 mmol) of 1-diphenylmethoxycarbonylmethyl-4-pyridothione was added, and reacted at room temperature for an hour. After the reaction, 8 ml of ethyl acetate was added, the reaction mixture was washed with 0.5 ml of 0.1N-HCl, then washed with water, dried on magnesium sulfate, and the solvent was removed to obtain 220 mg of diphenylmethyl (6R,7R)-[(Z)-2-(2-tritylaminothiazol-4-yl)-2-(diphenylmethoxycarbonylmethoxyimino)acetamido]-3-[(1-diphenylmethoxycarbonylmethylpyridinium-4-yl)thiomethyl]-ceph-3-em-4-carboxylate bromide.

70 mg of this compound was dissolved in 0.21 ml of anisole, 0.7 ml of trifluoroacetic acid was added with ice cooling, and reacted for 40 minutes. After the reaction, isopropyl ether was added to form precipitates. They were dried to obtain 40 mg of a powder, and, after adding 1.2 ml of water and adjusting the pH to 7.8 with $NaHCO_3$, purified with Diaion HP-20 resin (water) to obtain 20 mg of the title compound.

NMR ($D_2O$) δ: 3.55, 3.85 (2H, ABq, J=12), 4.15, 4.40 (2H, ABq, J=8), 4.50 (2H, s), 4.85 (2H, s), 4.95 (1H, d, J=4), 5.45 (1H, d, J=4), 6.45 (1H, s), 7.10 (2H, d, J=8), 7.50 (2H, d, J=8).

EXAMPLE 30

(6R,7R)-7-[(Z)-2-(2-Aminothiazol-4-yl)-2-(allyloxyimino)acetamido]-3-[(1-carboxymethylpyridinium-4-yl)thiomethyl]-ceph-3-em-4-carboxylic acid sodium salt 110 mg (0.12 mmol) of the 3-bromomethyl form synthesized in a manner similar to that in Example 27 was dissolved in 1.1 ml of DMF, 47 mg (0.14 mmol) of 1-diphenylmethoxycarbonylmethyl-4-pyridothione was added, and reacted at room temperature for an hour. After the reaction, 6 ml of ethyl acetate was added, the reaction mixture was washed with 3 ml of 0.1N-HCl, then washed with water, dried on magnesium sulfate, and the solvent was removed to obtain 150 mg of diphenylmethyl (6R,7R)-7-[2-(2-tritylaminothiazol-4-yl)-2-(allyloxyimino)acetamido]-3-[(1-diphenylmethoxycarbonylmethylpyridinium-4-yl)thiomethyl]-ceph-3-em-4-carboxylate bromide.

150 mg of this compound was dissolved in 0.45 ml of anisole, 1.5 ml of trifluoroacetic acid was added with ice cooling, and reacted for 40 minutes. After the reaction, isopropyl ether was added to form precipitates. They were dried to obtain 80 mg of a powder, and, after adding 2.4 ml of water and adjusting the pH to 7.8 with $NaHCO_3$, purified with Diaion HP-20 resin (methanol:$H_2O$=1:4) to obtain 40 mg of the title compound.

NMR ($D_2O$) δ: 3.30, 3.65 (2H, ABq, J=18), 4.05, 4.35 (2H, ABq, J=14), 4.90-6.20 (5H, m), 5.10 (1H, d, J=4), 5.70 (1H, d, J=4), 6.85 (1H, s), 7.70 (2H, d, J=8), 8.25 (2H, d, J=8).

EXAMPLE 31

(6R,7R)-7-[(Z)-2-(2-Aminothiazol-4-yl)-2-ethoxyiminoacetamido]-3-[1-(1-carboxy-1-ethylpyridinium-4-yl)thiomethyl]-ceph-3-em-4-carboxylic acid sodium salt 95 mg (0.105 mmol) of the 3-bromomethyl form used in Example 28 was dissolved in 0.95 ml of DMF, 42 mg (0.12 mmol) of 1-(1-diphenylmethoxycarbonyl-1-ethyl)-4-pyridothione was added, and reacted at room temperature for an hour. After the reaction, 5 ml of ethyl acetate was added, the reaction mixture was washed with 3 ml of 0.1N-HCl, then washed with water, dried on magnesium sulfate, and the solvent was removed to obtain 135 mg of diphenylmethyl (6R,7R)-7-[(Z)-2-(2-tritylaminothiazol-4-yl)-2-ethoxyiminoacetamido]-3-[1-(1-diphenylmethoxycarbonyl-1-ethylpyridinium-4-yl)thiomethyl]-ceph-3-em-4-carboxylate bromide, which was used in the next reaction without purification.

135 mg of this compound was dissolved in 0.40 ml of anisole, 1.35 ml of trifluoroacetic acid was added with ice cooling, and reacted for 40 minutes. After the reaction, isopropyl ether was added to form precipitates. They were dried to obtain 80 mg of a powder, and, after adding 2.4 ml of water and adjusting the pH to 7.8 with $NaHCO_3$, purified with Diaion HP-20 resin (methanol:$H_2O$=1:4) to obtain 55 mg of the title compound.

NMR ($D_2O$) δ: 1.20 (3H, t, J=6), 1.75 (2H, d, J=8), 3.30, 3.65 (2H, ABq, J=18), 4.15 (2H, q, J=6), 4.00, 4.30 (2H, ABq, J=12), 5.05 (1H, q, J=8), 5.10 (1H, d, J=4), 5.65 (1H, d, J=4), 6.85 (1H, s), 7.65 (2H, d, J=8), 8.30 (2H, d, J=8).

EXAMPLE 32

(6R,7R)-7-[(Z)-2-(2-Aminothiazol-4-yl)-2-ethoxyiminoacetamido]-3-[(1-carboxybenzylpyridinium-4-yl)thiomethyl]-ceph-3-em-4-carboxylic acid sodium salt 90 mg (0.1 mmol) of the 3-bromomethyl form used in Example 28 was dissolved in 0.9 ml of DMF, 62 mg (0.15 mmol) of 1-diphenylmethoxycarbonylbenzyl-4-pyridothione was added, and reacted at room temperature for an hour. After the reaction, 5 ml of ethyl acetate was added, the reaction mixture was washed with 3 ml of 0.1N-HCl, then washed with water, dried on magnesium sulfate, and the solvent was removed to obtain 150 mg of diphenylmethyl (6R,7R)-7-[(Z)-2-(2-tritylaminothiazol-4-yl)-2-ethoxyiminoacetamido]-3-[(1-diphenylmethoxycarbobenzylpyridinium-4-yl)thiomethyl]-ceph-3-em-4-carboxylate bromide.

150 mg of this compound was dissolved in 0.45 ml of anisole, 1.5 ml of trifluoroacetic acid was added with ice cooling, and reacted for 40 minutes. After the reaction, isopropyl ether was added to form precipitates. They were dried to obtain 80 mg of a powder, and, after adding 2.4 ml of water and adjusting the pH to 7.8 with $NaHCO_3$, purified with Diaion HP-20 resin (methanol:$H_2O$=1:4) to obtain 30 mg of the title compound.

NMR ($D_2O$) δ: 1.25 (3H, t, J=6), 3.35, 3.70 (2H, ABq, J=18), 4.10 (2H, q, J=6), 4.05, 4.30 (2H, ABq, J=10), 5.05 (1H, d, J=4), 5.65 (1H, d, J=4), 6.85 (1H, s), 7.40 (5H, s), 7.60 (2H, d, J=8), 8.25 (2H, d, J=8).

EXAMPLE 33

(6R,7R)-7-[(Z)-2-(2-Aminothiazol-4-yl)-2-ethoxyiminoacetamido]-3-[(1carboxymethylpyrimidinium-2-yl)thiomethyl]-ceph-3-em-4-carboxylic acid sodium salt 110 mg (0.13 mmol) of the 3-bromomethyl form used in Example 28 was dissolved in 1.1 ml of DMF, 47 mg (0.14 mmol) of 1-diphenylmethoxycarbonylmethyl-2-pyridothione and 42 mg (0.28 mmol) of NaI were added, and reacted at room temperature for an hour. After the reaction, 6 ml of ethyl acetate was added, the reaction mixture was washed with 3 ml of 0.1N-HCl, then washed with water, dried on magnesium sulfate, and the solvent was removed to obtain 155 mg of diphenylmethyl (6R,7R)-7-[(Z)-2-(2-tritylaminothiazol-4-yl)-2-ethoxyiminoacetamido]-3-[(1-diphenylmethoxycarbonylmethylpyridinium-2-yl)thiomethyl]-ceph-3-em-4-carboxylate iodide.

155 mg of this compound was dissolved in 0.47 ml of anisole, 1.55 ml of trifluoroacetic acid was added with ice cooling, and reacted for 40 minutes. After the reaction, isopropyl ether was added to form precipitates. They were dried to obtain 90 mg of a powder, and, after adding 2.7 ml of water and adjusting the pH to 7.8 with NaHCO$_3$, purified with Diaion HP-20 resin (methanol:-H$_2$O=1:4) to obtain 50 mg of the title compound.

NMR (D$_2$O) δ: 1.25 (3H, t, J=6), 3.40, 3.75 (2H, ABq, J=20), 4.20 (2H, q, J=6), 4.15, 4.45 (2H, ABq, J=12), 5.20 (2H, s), 5.15 (1H, d, J=4), 5.70 (1H, d, J=4), 6.90 (1H, s), 7.60–8.70 (4H, m).

EXAMPLE 34

(6R,7R)-7-[(Z)-2-(2-Aminothiazol-4-yl)-2-methoxyiminoacetamido]-3-[(2,3-cyclopenteno-1-carboxymethylpyridinium-4-yl)thiomethyl]-ceph-3-em-4-carboxylic acid sodium salt 720 mg of (6R,7R)-7-[(Z)-2-(2-aminothiazol-4-yl)-2-methoxyiminoacetamido]-3-acetoxymethyl-ceph-3-em-4-carboxylic acid sodium salt was dissolved in 6 ml of water and 6 ml of acetonitrile, 350 mg of 1-carboxymethyl-cyclopentano [b]-4-thiopyridine and 2.25 g of sodium iodide were added, then the pH of the reaction mixture was adjusted to 6.5–7.0 with a saturated sodium bicarbonate aqueous solution, and a reaction was effected at 70° C. for 8 hours. After the completion of the reaction, the reaction mixture was concentrated to a small volume under reduced pressure, 70 ml of acetone was added dropwise thereto with ice cooling, and the formed precipitates were filtered off. They were dissolved in water, and purified by Diaion HP-20 column chromatography (eluted with 15% acetone-water). The fractions containing the desired product were concentrated, and freeze dried to obtain 560 mg of the title compound.

NMR (D$_2$O) δ: 2.31 (m, 2H), 3.00 (t, 2H), 3.18 (t, 2H), 3.63 (ABq, 2H), 4.01 (s, 3H), 4.33 (ABq, 2H), 4.96 (s, 2H), 5.22 (d, 1H), 5.78 (d, 1H), 6.98 (s, 1H), 7.67 (d, 1H), 8.20 (d, 1H).

Compounds of Examples 35–45 were obtained in a manner similar to that in Example 34 except that the 1-carboxymethyl-cyclopentano [b]-4-thiopyridone was replaced by various reagents (B) respectively.

EXAMPLE 35

(6R,7R)-7-[(Z)-2-(2-Aminothiazol-4-yl)-2-methoxyiminoacetamido]-3-[(2,3-cyclopenteno-1-carbamoylmethylpyridinium-4-yl)thiomethyl]-ceph-3-em-4-carboxylate (B) 1-Carbamoylmethyl-cyclopentano [b] 4-thiopyridone NMR (D$_2$O) δ: 2.33 (m, 2H), 3.03 (t, 2H), 3.22 (t, 2H), 3.60 (ABq, 2H), 4.01 (s, 3H), 4.34 (ABq, 2H), 4.92 (s, 2H), 5.19 (d, 1H), 5.80 (d, 1H), 7.03 (s, 1H), 7.67 (d, 1H), 8.23 (d, 1H).

EXAMPLE 36

(6R,7R)-7-[(Z)-2-(2-Aminothiazol-4-yl)-2-methoxyiminoacetamido]-3-[(2,3-cyclopenteno-1-cyanomethylpyridinium-4-yl)thiomethyl]-ceph-3-em-4-carboxylate (B) 1-Cyanomethyl-cyclopentano [b] 4-thiopyridone NMR (D$_2$O) δ: 2.35 (m, 2H), 3.00 (t, 2H), 3.38 (t, 2H), 3.60 (ABq, 2H), 3.97 (s, 3H), 4.33 (ABq, 2H), 4.77 (s, 2H), 5.18 (d, 1H), 5.76 (d, 1H), 6.97 (s, 1H), 7.73 (d, 1H), 8.36 (d, 1H).

EXAMPLE 37

(6R,7R)-7-[(Z)-2-(2-Aminothiazol-4-yl)-2-methoxyiminoacetamido]-3-[[2,3-cyclopenteno-1-(2-hydroxyethyl)pyridinium-4-yl]thiomethyl]-ceph-3-em-4-carboxylate (B) 1-(2-Hydroxyethyl)-cyclopentano [b]-4-thiopyridone NMR (D$_2$O+CD$_3$OD) δ: 2.36 (m, 2H), 3.06 (t, 2H), 3.39 (t, 2H), 3.64 (ABq, 2H), 4.05 (d, 3H), 4.44 (ABq, 2H), 4.54 (m, 2H), 5.21 (d, 1H), 5.81 (d, 1H), 6.97 (s, 1H), 7.84 (d, 1H), 8.27 (d, 1H).

EXAMPLE 38

(6R,7R)-7-[(Z)-2-(2-Aminothiazol-4-yl)-2-methoxyiminoacetamido]-3-[[2,3-cyclopenteno-1-(2-dimethylaminoethyl)pyridinium-4-yl]thiomethyl]-ceph-3-em-4-carboxylate (B) 1-(2-Dimethylaminoethyl)cyclopentano [b]-4-thiopyridone NMR (D$_2$O) δ: 2.41 (m, 2H), 2.42 (s, 6H), 2.90–3.10 (m, 4H), 3.41 (m, 2H), 3.71 (ABq, 2H), 3.98 (s, 3H), 4.45 (ABq, 2H), 4.56 (m, 2H), 5.29 (d, 1H), 5.83 (d, 1H), 7.02 (s, 1H), 7.99 (d, 1H), 8.36 (d, 1H).

EXAMPLE 39

(6R,7R)-7-[(Z)-2-(2-Aminothiazol-4-yl)-2-methoxyiminoacetamido]-3-[[2,3-cyclopenteno-1-(2-sulfoethyl)pyridinium-4-yl]thiomethyl]-ceph-3-em-4-carboxylic acid sodium salt (B) 1-(2-Sulfoethyl)-cyclopentano [b]-4-thiopyridone NMR (D$_2$O) δ: 2.34 (m, 2H), 3.00 (t, 2H), 3.39 (t, 2H), 3.51 (t, 2H), 3.62 (ABq, 2H), 4.01 (s, 3H), 4.32 (ABq, 2H), 4.76 (t, 2H), 5.21 (d, 1H), 5.80 (d, 1H), 7.02 (s, 1H), 7.66 (d, 1H), 8.36 (d, 1H).

EXAMPLE 40

(6R,7R)-7-[(Z)-2-(2-Aminothiazol-4-yl)-2-methoxyiminoacetamido]-3-[(2,3-cyclopenteno-1-methylthiomethylpyridinium-4-yl)thiomethyl]-ceph-3-em-4-carboxylate (B) 1-Methylthiomethyl-cyclopentano [b]-4-thiopyridone NMR (D$_2$O) δ: 2.14 (s, 3H), 2.31 (m, 2H), 2.97 (t, 2H), 3.34 (t, 2H), 3.58 (ABq, 2H), 3.96 (s, 3H), 4.32 (ABq, 2H), 5.15 (d, 1H), 5.40 (s, 2H), 5.72 (d, 1H), 6.94 (s, 1H), 7.68 (d, 1H), 8.40 (d, 1H).

EXAMPLE 41

(6R,7R)-7-[(Z)-2-(2-Aminothiazol-4-yl)-2-methoxyiminoacetamido]-3-[[2,3-cyclopenteno-1-(2-carboxyethyl)pyridinium-4-yl]thiomethyl]-ceph-3-em-4-carboxylic acid sodium salt (B) 1(2-Carboxyethyl)-cyclopentano [b] 4-thiopyridone NMR (D$_2$O) δ: 2.33 (m, 2H), 3.01 (t, 2H), 3.20 (t, 2H), 3.39 (t, 2H), 3.63 (ABq, 2H), 4.00 (s, 3H), 4.31 (ABq, 2H), 4.83 (t, 2H), 5.21 (d, 1H), 5.79 (d, 1H), 7.04 (s, 1H), 7.09 (d, 1H), 8.34 (d, 1H).

EXAMPLE 42

(6R,7R)-7-[(Z)-2-(2-Aminothiazol-4-yl)-2-methoxyiminoacetamido]-3-[(2,3-cyclohexeno-1-carboxymethyl)pyridinium-4-yl)thiomethyl]-ceph-3-em-4-carboxylic acid sodium salt (B) 1-Carboxymethyl-cyclohexano [b]-4-thiopyridone NMR (D$_2$O) δ: 1.83 (m, 2H), 1.90 (m, 2H), 2.68 (t, 2H), 2.95 (t, 2H), 3.61 (ABq, 2H), 4.01 (s, 3H), 4.09 (ABq, 2H), 4.92 (s, 2H), 5.20 (d, 1H), 5.77 (d, 1H), 6.99 (s, 1H), 7.66 (d, 1H), 8.19 (d, 1H).

EXAMPLE 43

(6R,7R)-7-[(Z)-2-(2-Aminothiazol-4-yl)-2-methoxyiminoacetamido]-3-[(3,4-cyclopenteno-1-carboxymethylpyridinium-2-yl)thiomethyl]-ceph-3-em-4-carboxylic acid sodium salt (B) 1-Carboxymethyl-cyclopentano [c]-2-thiopyridone NMR (D$_2$O) δ: 2.23 (m, 2H), 3.10–3.30 (m, 4H), 3.70 (ABq, 2H), 4.01 (s, 3H), 4.21 (ABq, 2H), 4.95 (s, 2H), 5.21 (d, 1H), 5.75 (d, 1H), 7.02 (s, 1H), 7.80 (d, 1H), 8.65 (d, 1H).

EXAMPLE 44

(6R,7R)-7-[(Z)-2-(2-Aminothiazol-4-yl)-2-methoxyiminoacetamido]-3[(3,4-cyclopenteno-1-methylopyridinium-2-yl)thiomethyl]-ceph-3-em-4-carboxylate (B) 1-Methyl-cyclopentano [c]-2-thiopyridone NMR (D$_2$O) δ: 2.23 (m, 2H), 3.23 (m, 4H), 3.75 (ABq, 2H), 4.02 (s, 3H), 4.11 (ABq, 2H), 4.42 (s, 3H), 5.22 (d, 1H), 5.83 (d, 1H), 7.04 (s, 1H), 7.78 (d, 1H), 8.63 (d, 1H).

EXAMPLE 45

(6R,7R)-7-[(Z)-2-(2-Aminothiazol-4-yl)-2-methoxyiminoacetamido]-3-[(2,3-cyclopentenopyridine-N-oxid-4-yl)thiomethyl]-ceph-3-em-4-carboxylate (B) 1-Hydroxy-cyclopentano [b]-4-thiopyridone NMR (D$_2$O) δ: 2.27 (m, 2H), 3.01 (m, 2H), 3.18 (t, 2H), 3.66 (ABq, 2H), 4.08 (s, 3H), 4.47 (ABq, 2H), 5.23 (d, 1H), 5.82 (d, 1H), 7.06 (s, 1H), 7.38 (d, 1H), 8.06 (d, 1H).

Compounds of Examples 46–48 were obtained in a manner similar to that in Example 34 but using (6R,7R)-7-[(Z)-2-(2-aminothiazol-4-yl)-2-ethoxyiminoacetamido]-3-(acetoxymethyl)-ceph-3-em-4-carboxylic acid sodium salt together with various reagents (B) respectively.

EXAMPLE 46

(6R,7R)-7-[(Z)-2-(2-Aminothiazol-4-yl)-2-ethoxyiminoacetamido]-3-[(2,3-cyclopenteno-1-carboxymethylpyridinium-4-yl)thiomethyl]-ceph-3-em-4-carboxylic acid sodium salt (B) 1-Carboxymethyl-cyclopentano [b] 4-thiopyridone NMR (D$_2$O) δ: 1.32 (t, 3H), 2.31 (m, 2H), 3.01 (t, 2H), 3.19 (t, 2H), 3.62 (ABq, 2H), 4.28 (q, 2H), 4.33 (ABq, 2H), 4.95 (s, 2H), 5.21 (d, 1H), 5.80 (d, 1H), 6.98 (s, 1H), 7.64 (d, 1H), 8.20 (d, 1H).

EXAMPLE 47

(6R,7R)-7-[(Z)-2-(2-Aminothiazol-4-yl)-2-ethoxyiminoacetamido]-3-[(2,3-cyclopenteno-1-carbamoylmethylpyridinium-4-yl)thiomethyl]-ceph-3-em-4-carboxylate (B) 1-Carbamoylmethyl-cyclopentano [b] 4-thiopyridone NMR (D$_2$O) δ: 1.32 (t, 3H), 2.33 (m, 2H), 3.04 (t, 2H), 3.23 (t, 2H), 3.60 (ABq, 2H), 4.28 (q, 2H), 4.34 (ABq, 2H), 4.92 (s, 2H), 5.19 (d, 1H), 5.81 (d, 1H), 7.03 (s, 1H), 7.64 (d, 1H), 8.23 (d, 1H).

EXAMPLE 48

(6R,7R)-7-[(Z)-2-(2-Aminothiazol-4-yl)-2-ethoxyiminoacetamido]-3-[[2,3-cyclopenteno-1-(2-sulfoethyl)pyridinium-4-yl]thiomethyl]-ceph-3-em-4-carboxylic acid sodium salt (B) 1-(2-Sulfoethyl)-cyclopentano [b]-4-thiopyridone NMR (D$_2$O) δ: 1.32 (t, 3H), 2.34 (m, 2H), 3.00 (t, 2H), 3.39 (t, 2H), 3.51 (t, 2H), 3.62 (ABq, 2H), 4.28 (q, 2H), 4.32 (ABq, 2H), 4.75 (t, 2H), 5.29 (d, 1H), 5.82 (d, 1H), 7.02 (s, 1H), 7.63 (d, 1H), 8.36 (d, 1H).

EXAMPLE 49

(6R,7R)-7-[(Z)-2-(2-Aminothiazol-4-yl)-2-(carbamoylmethoxyimino)acetamido]-3-[(2,3-cyclopenteno-1-methylpyridinium-4-yl)thiomethyl]-ceph-3-em-4-carboxylate 500 mg of (6R,7R)-7-[(Z)-2-(2-aminothiazol-4-yl)-2-(carbamoylmethoxyimino)acetamido]-3-(acetoxymethyl)-ceph-3-em-4-carboxylic acid sodium salt was dissolved in 2 ml of water and 2 ml of acetonitrile, 1.5 g of sodium iodide and 182 mg of 1-methyl-cyclopentano-[b]-4-thiopyridone were added thereto, and a reaction was effected at 65°–70° 1 C. for 5 hours while maintaining the pH of the reaction mixture at 6.5–7.0. After the completion of the reaction, treatment similar to that in Example 34 was conducted, the formed precipitates were dissolved in a small quantity of 50% aqueous methanol, purified by Sephadex LH-20 column chromatograph (packed with 50% aqueous methanol), then, the fractions containing the desired product were concentrated, and freeze dried to obtain 240 mg of the title compound.

NMR (D$_2$O-CD$_3$OD) δ: 2.31 (m, 2H), 2.98 (t, 2H), 3.27 (t, 2H), 3.58 (ABq, 2H), 4.06 (s, 3H), 4.33 (ABq, 2H), 4.69 (s, 2H), 5.16 (d, 1H), 5.78 (d, 1H), 7.03 (s, 1H), 7.65 (d, 1H), 8.24 (d, 1H).

EXAMPLE 50

(6R,7R)-7-[(Z)-2-(2-Aminothiazol-4-yl)-2-(2-fluoroethoxyimino)acetamido]-3-[(2,3-cyclopenteno-1-carboxymethylpyridinium-4-yl)thiomethyl]-ceph-3-em-4-carboxylic acid sodium salt 255 mg of (6R,7R)-7-[(Z)-2-(2-aminothiazol-4-yl)-2-(2-fluoroethoxyimino)acetamido]-3-(acetoxymethyl)-ceph-3-em-4-carboxylic acid sodium salt and 110 mg of 1-carboxymethyl-cyclopentano [b]-4-thiopyridone were reacted in a manner similar to that in Example 34, and purified to obtain 150 mg of the title compound.

NMR (D$_2$O) δ: 2.33 (m, 2H), 3.02 (t, 2H), 3.19 (t, 2H), 3.63 (ABq, 2H), 4.33 (ABq, 2H), 4.60–4.75 (m, 2H), 4.85–5.05 (m, 2H), 4.95 (s, 2H), 5.21 (d, 1H), 5.82 (d, 1H), 7.05 (s, 1H), 7.64 (d, 1H), 8.20 (d, 1H).

EXAMPLE 51

(6R,7R)-7-[(Z)-2-(2-Aminothiazol-4-yl)-2-(carboxymethoxyimino)acetamido]-3-[(2,3-cyclopenteno-1-methylpyridinium-4-yl)thiomethyl]-ceph-3-em-4-carboxylic acid sodium salt 615 mg of (6R,7R)-7-[(Z)-2-(2-aminothiazol-4-yl)-2-(carboxymethoxyimino)acetamido]-3-acetoxymethyl-ceph-3-em-4-carboxylic acid sodium salt was dissolved in 1.5 ml of water and 3.0 ml of acetonitrile, 1.5 g of sodium iodide and 182 mg of 1-methyl-cyclopentano-[b]-4-thiopyridone were added thereto, and a reaction was effected at 65° C. for 9 hours while maintaining the pH of the reaction mixture at 6.5–7.0. After the completion of the reaction, the reaction mixture was concentrated under reduced pressure to remove the acetonitrile, and 20 ml of acetone was added. The formed precipitates were filtered off, washed thoroughly with acetone, dissolved in a small quantity of water, and purified by Diaion HP-20 chromatography. The fractions containing the desired product were concentrated, and freeze dried to obtain 280 mg of the title compound.

NMR (D$_2$O) δ: 2.31 (m, 2H), 3.00 (m, 2H), 3.26 (t, 2H), 3.62 (ABq, 2H), 4.05 (s, 3H), 4.31 (ABq, 2H), 4.57 (s, 2H), 5.20 (d, 1H), 5.76 (d, 1H), 6.97 (s, 1H), 7.69 (d, 1H), 8.18 (d, 1H).

Compounds of Examples 52 and 53 were obtained in a manner similar to that in Example 51 except that the 1-methyl-cyclopentano [b] 4-thiopyridone was replaced by various reagents (B) respectively.

EXAMPLE 52

(6R,7R)-7-[(Z)-2-(2-Aminothiazol-4-yl)-2-(carboxymethoxyimino)acetamido]-3-[(2,3-cyclopenteno-1-carboxymethylpyridinium-4-yl)thiomethyl]-ceph-3-em-4-carboxylic acid sodium salt (B) 1-Carboxymethyl-cyclopentano [b]-4-thiopyridone NMR (D$_2$O) δ: 2.31 (m, 2H), 3.00 (t, 2H), 3.18 (t, 2H), 3.63 (ABq, 2H), 4.33 (ABq, 2H), 4.56 (s, 2H), 4.96 (s, 2H), 5.21 (d, 1H), 5.77 (d, 1H), 6.97 (s, 1H), 7.67 (d, 1H), 8.20 (d, 1H).

EXAMPLE 53

(6R,7R)-7-[(Z)-2-(2-Aminothiazol-4-yl)-2-(carboxymethoxyimino)acetamido]-3-[[2,3-cyclopenteno-1-(2-sulfoethyl)pyridinium-4-yl]thiomethyl]-ceph-3-em-4-carboxylic acid sodium salt (B) 1-(2-Sulfoethyl)-cyclopentano [b]-4-thiopyridone NMR (D$_2$O) δ: 2.34 (m, 2H), 3.00 (t, 2H), 3.39 (t, 2H), 3.51 (t, 2H), 3.62 (ABq, 2H), 4.32 (ABq, 2H), 4.57 (s, 2H), 4.76 (t, 2H), 5.21 (d, 1H), 5.79 (d, 1H), 7.01 (s, 1H), 7.66 (d, 1H), 8.32 (d, 1H).

Compounds of Examples 54–56 were obtained in a manner similar to that in Example 51 using (6R,7R)-7-[(Z)-2-(2-aminothiazol-4-yl)-2-(1-methyl-1-carboxyethoxyimino)acetamido]-3-acetoxymethyl-ceph-3-em-4-carboxylic acid sodium salt together with various reagents (B) respectively.

EXAMPLE 54

(6R,7R)-7-[(Z)-2-(2-Aminothiazol-4-yl)-2-carboxymethoxyimino)acetamido]-3-[(2,3-cyclopenteno-1-cyclopropylpyridinium-4-yl)thiomethyl]-ceph-3-em-4-carboxylate (B) 1-Cyclopropyl-cyclopentano [b]-4-thiopyridone NMR (D$_2$O) δ: 1.26 (m, 2H), 1.31 (m, 2H), 2.31 (m, 2H), 2.98 (t, 2H), 3.40 (t, 2H), 3.60 (ABq, 2H), 3.89 (m, 1H), 4.31 (ABq, 2H), 4.57 (s, 2H), 5.19 (d, 1H), 5.77 (d, 1H), 7.01 (s, 1H), 7.63 (d, 1H), 8.27 (d, 1H).

EXAMPLE 55

(6R,7R)-7-[(Z)-2-(2-Aminothiazol-4-yl)-2-(1-methyl-1-carboxyethoxyimino)acetamido]-3-[(2,3-cyclopenteno-1-carbamoylmethylpyridinium-4yl)thiomethyl]-ceph-3-em-4-carboxylic acid sodium salt (B) 1-Carbamoylmethyl-cyclopentano [b]-4-thiopyridone NMR (D$_2$O) δ: 1.50 (s, 3H), 1.51 (s, 3H), 2.31 (m, 2H), 3.04 (t, 2H), 3.24 (t, 2H), 3.61 (ABq, 2H), 4.34 (ABq, 2H), 4.93 (s, 2H), 5.20 (d, 1H), 5.82 (d, 1H), 7.02 (s, 1H), 7.67 (d, 1H), 8.23 (d, 1H).

EXAMPLE 56

(6R,7R)-7-[(Z)-2-(2-Aminothiazol-4-yl)-2-(1-methyl-1-carboxyethoxyimino)acetamido]-3-[(2,3-cyclopenteno-1-carboxymethylpyridinium-4-yl)thiomethyl]-ceph-3-em-4-carboxylic acid sodium salt (B) 1-Carboxymethyl-cyclopentano [b]-4-thiopyridone NMR (D$_2$O) δ: 1.51 (s, 3H), 1.52 (s, 3H), 2.31 (m, 2H), 3.01 (t, 2H), 3.19 (t, 2H), 3.62 (Abq, 2H), 4.33 (ABq, 2H), 4.96 (s, 2H), 5.21 (d, 1H), 5.79 (d, 1H), 7.00 (s, 1H), 7.67 (d, 1H), 8.20 (d, 1H).

EXAMPLE 57

(6R,7R)-7-[(Z)-2-(2-Aminothiazol-4-yl)-2-(3DL-amino-3-carboxypropyloxyimino)acetamido]-3-[(2,3-cyclopenteno-1-carboxymethylpyridinium-4-yl)thiomethyl]-ceph-3-em-4-carboxylic acid sodium salt 540 mg of the (6R,7R)-7-[(Z)-2-(2-aminothiazol-4-yl)-2-(3DL-3-amino-3-carboxypropyloxyimino)acetamido]-3-acetoxymethyl-ceph-3-em-4-carboxylate obtained in Example 11 (f) was dissolved in 5 ml of water and 5 ml of acetonitrile, 1.5 g of sodium iodide and 310 mg of 1-carboxymethyl-cyclopentano [b]-4-thiopyridone were added thereto, and reacted at 65° C. for 4 hours while adjusting the pH of the reaction mixture to 6.5–7.0.

After the completion of the reaction, the reaction mixture was concentrated under reduced pressure to remove the acetonitrile, 50 ml of acetone was added, the formed precipitates were filtered off, washed thoroughly with acetone, dissolved in a small quantity of water and purified by Diaion HP-20 chromatography. The fractions containing the desired product were concentrated, and freeze dried to obtain 230 mg of the title compound.

NMR (D$_2$O) δ: 2.25 (m, 2H), 2.31 (m, 2H), 3.00 (t, 2H), 3.18 (t, 2H), 3.63 (ABq, 2H), 4.05 (m, 1H), 4.34 (ABq, 2H), 4.60 (m, 2H), 4.96 (s, 2H), 5.18 (d, 1H), 5.76 (d, 1H), 7.02 (d, 1H), 7.67 (d, 1H), 8.20 (d, 1H).

EXAMPLE 58

(6R,7R)-7-[(Z)-2-(2-Aminothiazol-4-yl)-2-(2D-2-amino-2-carboxyethoxyimino)acetamido]-3-[(2,3-cyclopenteno-1-carbamoylmethylpyridinium-4-yl)thiomethyl]-ceph-3-em-4-carboxylate 260 mg of the (6R,7R)-7-[(Z)-2-(2-aminothiazol-4-yl)-2-(2D-2-amino-2-carboxyethoxyimino)acetamido]-3-acetoxymethyl-ceph-3-em-4-carboxylate obtained in Example 12 (c) was dissolved in 1.5 ml of water and 1.5 ml of acetonitrile, 750 mg of sodium iodide and 150 mg of 1-carbamoylmethyl-cyclopentano [b] 4-thiopyridone were added, and reacted at 65° C. for 4 hours while maintaining the pH of the reaction mixture of 6.5–7.0. After the completion of the reaction, the reaction mixture was treated in a manner similar to that in Example 57 to obtain 95 mg of the title compound.

NMR (D$_2$O) δ: 2.33 (m, 2H), 3.03 (t, 2H), 3.23 (t, 2H), 3.61 (Abq, 2H), 4.02 (m, 1H), 4.31 (ABq, 2H), 4.57 (m, 2H), 4.89 (s, 2H), 5.21 (d, 1H), 5.78 (d, 1H), 7.01 (s, 1H), 7.66 (d, 1H), 8.21 (d, 1H).

Compounds of Examples 59 and 60 were obtained in a manner similar to that in Example 57 except that the 1-carbamoylmethyl-cyclopentano [b] 4-thiopyridone was replaced by the reagents (B) respectively.

EXAMPLE 59

(6R,7R)-7-[(Z)-2-(2-Aminothiazol-4-yl)-2-(2D-2-amino-2-carboxyethoxyimino)acetamido]-3-[(3,4-cyclopenteno-1-methylpyridinium-4-yl)thiomethyl]-ceph-3-em-4-carboxylate (B) 1-Methyl-cyclopentano [c]-2-thiopyridone NMR (D$_2$O) δ: 2.23 (m, 2H), 3.25 (m, 4H), 3.73 (ABq, 2H), 4.05 (m, 1H), 4.19 (ABq, 2H), 4.41 (s, 3H), 4.55 (m, 2H), 5.22 (d, 1H), 5.75 (d, 1H), 7.03 (s, 1H), 7.75 (d, 1H), 8.62 (d, 1H).

EXAMPLE 60

(6R,7R)-7-[(Z)-2-(2-Aminothiazol-4-yl)-2-(2D-2-amino-2-carboxyethyoxyimino)acetamido]-3-[(2,3-cyclopenteno-1-methylpyridinium-4-yl)thiomethyl]-ceph-3-em-4-carboxylate (B) 1-Methyl-cyclopentano [b]-4-thiopyridone NMR (D$_2$O) δ: 2.32 (m, 2H), 3.00 (t, 2H), 3.25 (t, 2H), 3.63 (ABq, 2H), 4.01 (s, 3H), 4.06 (m, 1H), 4.33 (ABq, 2H), 4.45 (m, 2H), 5.20 (d, 1H), 5.75 (d, 1H), 6.99 (s, 1H), 7.67 (d, 1H), 8.21 (d, 1H).

EXAMPLE 61

(6R,7R)-7-[(Z)-2-(2-Aminothiazol-4-yl)-2-methoxyiminoacetamido]-3-[(3,4-cyclopenteno-1-methylpyridinium-2-yl)thiomethyl]-ceph-3-em-4-carboxylate 546 mg of (6R,7R)-7-[(Z)-2-(2-aminothiazol-4-yl)-2-methoxyiminoacetamido]-3-(acetoxymethyl)-ceph-3-em-4-carboxylic acid was suspended in 5.6 ml of anhydrous dichloromethane, and in argon atmosphere, 0.64 ml of N,O-bistrimethylsilyltrifluoroacetamido was added followed by stirring at room temperature for an hour. 0.51 ml of trimethylsilyl iodide was added thereto, and the reaction was further effected at room temperature for another hour. Thereafter, the reaction mixture was concentrated under reduced pressure, the residue was dissolved in 3.0 ml of anhydrous acetonitrile, and further 0.2 ml of anhydrous tetrahydrofuran was added. Five minutes later, 240 mg of 1-methyl-cyclopentano [c] 2-thiopyridone dissolved in 1 ml of anhydrous dichloromethane was added, and reacted at room temperature for 1.5 hours.

After the completion of the reaction, 0.24 ml of water was added with ice cooling, and further 20 ml of ether was added.

The formed precipitates were filtered off, washed thoroughly with a mixed solution of acetonitrile-ether, dried, then suspended in a small quantity of water, dissolved in making the pH 7.2 with a saturated sodium bicarbonate aqueous solution, and purified by Diaion HP-20 column chromatography. The fractions containing the desired product were concentrated, and freeze dried to obtain 210 mg of the title compound. This compound had spectral data identical to those of the compound obtained in Example 44.

EXAMPLE 62

(6R,7R)-7-[(Z)-2-(2-Aminothiazol-4-yl)-2-methoxyiminoacetamido]-3-[(2,3-cyclopenteno-1-carbamoylmethylpyridinium-4-yl)thiomethyl]-ceph-3-em-4-carboxylate 400 mg of (6R,7R)-(Z)-2-(2-aminothiazol-4-yl)-2-methoxyiminoacetic acid was dissolved in 4 ml of N,N-dimethylformamide, 270 mg of N-hydroxybenztriazole and 415 mg of N,N-dicyclohexylcarbodiimide were added thereto, and reacted at room temperature for an hour.

Separately, 820 mg of 7-amino-3-(2,3-cyclopenteno-1-carbamoylmethylpyridinium-4-yl)thiomethyl-ceph-3-em-4-carboxylate was suspended in 5 ml of N,N-dimethylformamide, and 0.45 ml of triethylamine was added with ice cooling. Thereafter, the above reaction mixture was added, and reacted at 5° C. overnight.

After the completion of the reaction, the insoluble matter was removed by filtration, ether was added, the formed precipitates were filtered off, and washed with ethyl acetate.

The precipitates were dissolved in a small quantity of water, and, after adjusting the pH of 6.5–7.0, purified by HP-20 column chromatography. The fractions containing the desired product were concentrated, and freeze dried to obtain the title compound. The spectral data of this compound were identical to those of Example 35.

EXAMPLE 63

(6R,7R)-7-[(Z)-2-(2-Aminothiazol-4-yl)-2-[(2-amino-thiazol-4-yl)methoxyimino]acetamido]-3-[(2,3-cyclopenteno-1-methylpyridinium-4-yl)thiomethyl]-ceph-3-em-4-carboxylate (a) 8.15 g of N-hydroxyphthalimide was dissolved in 300 ml of N,N-dimethylformamide, 6.91 g of potassium carbonate and 200 mg of dicyclohexyl-18-crown-6 were added, and stirred at room temperature for 2 hours. Thereafter, 9.82 g of 4-chloromethyl-2-tritylamino-thiazol was added thereto, and stirred and reacted at room temperature for 8 hours. The reaction mixture was concentrated under reduced pressure, and, after adding 500 ml of ethyl acetate, washed with 300 ml of water 4 times. The ethyl acetate layer was dried on anhydrous magnesium sulfate, and concentrated to dryness to obtain 12.5 g of (2-tritylaminothiazol-4-yl)methoxyphthalimide.

To a solution of 12.0 g of the (2-tritylaminothiazol-4-yl)methoxyphthalimide in 400 ml of dichloromethane was added 1.161 g of hydrazine hydrate with cooling, and the mixture was stirred at room temperature for 5 hours. The formed precipitates were removed by filtration, the dichloromethane layer was washed with 300 ml of 10% ammonia water three times and then with 300 ml of saturated saline twice, dried on anhydrous magnesium sulfate, and concentrated to dryness to obtain 8.74 g of (2-tritylaminothiazol-4-yl)methoxyamine.

(b) 3.1 g of 2-(2-tritylaminothiazol-4-yl)glyoxalic acid was dissolved in 170 ml of methanol, 2.9 g of the (2-tritylaminothiazol-4-yl)methoxyamine was added thereto, and stirred at room temperature for 4 hours. The formed precipitates were filtered off and washed with 20 ml of methanol to obtain 5.1 g of (Z)-2-(2-tritylaminothiazol-4-yl)-2-[(2-tritylaminothiazol-4-yl)methoxyimino]acetic acid.

(c) 2.3 g of the (Z)-2-(2-tritylaminothiazol-4-yl)-2-[(2-tritylaminothiazol-4-yl)methoxyimino]acetic acid was dissolved in a mixed solution of 7 ml of N,N-dimethylformamide and 70 ml of dichloromethane, 440 mg of 1-hydroxybenztriazole and 670 mg of dicyclohexylcarbodiimide were added, and reacted at room temperature for 4 hours.

964 mg of 7-aminocephalosporanic acid t-butyl ester was added to the reaction mixture, and then reacted with stirring at room temperature for 2 days. 200 ml of chloroform was added to the reaction mixture, which has then washed with dilute hydrochloric acid (pH 1.5), then with saturated saline three times, the chloroform layer was concentrated to dryness under reduced pressure, and purified by silica gel chromatography (developing solvent: chloroform:ethyl acetate 20:1) to obtain 2.7 g of (6R,7R)-7-[(Z)-2-(2-tritylaminothiazol-4-yl)-2-[(2-tritylaminothiazol-4-yl)methoxyimino]acetamido]-3-(acetoxymethyl)-ceph-3-em-4-carboxylic acid t-butyl ester.

(d) 2.3 g of the (6R,7R)-7-[(Z)-2-(2-tritylaminothiazol-4-yl)-2-[(2-tritylaminothiazol-4-yl)methoxyimino]acetamido]-3-(acetoxymethyl)-ceph-3-em-4-carboxylic acid t-butyl ester was suspended in 2.1 ml of anisole, 21 ml of trifluoroacetic acid was added with ice cooling, and reacted at the same temperature for about 3 hours. After the completion of the reaction, the reaction mixture was poured into 200 ml of isopropyl ether with ice cooling, and the supernatant was removed. The residue was washed thoroughly with isopropyl ether, and the precipitates were filtered off to obtain 1.4 g of (6R,7R)-7-[(Z)-2-(2-aminothiazol-4-yl)-2-[(2-amino-thiazol-4-yl)methoxyimino]acetamido]-3-(acetoxymethyl)-ceph-3-em-4-carboxylic acid trifluoroacetate.

This was suspended in 3 ml of methanol and 6 ml of water, the pH was adjusted to 7.5 with a saturated sodium bicarbonate aqueous solution, and the insoluble matter was removed. The methanol was removed by concentration under reduced pressure, the residue was purified by Diaion HP-20 column chromatography. The fractions containing the desired product were concentrated, and freeze dried to obtain 800 mg of (6R,7R)-7-[(Z)-2-(2-aminothiazol-4-yl)-2-[(2-aminothiazol-4-yl)methoxyimino]acetamido]-3-(acetoxymethyl)-ceph-3-em-4-carboxylic acid sodium salt.

NMR ($D_2O$) δ: 2.10 (s, 3H), 3.48 (ABq, 2H), 4.80 (ABq, 2H), 5.05 (s, 2H), 5.15 (d, 1H), 5.79 (d, 1H), 6.71 (s, 1H), 7.02 (s, 1H).

(e) 575 mg of the compound obtained in (d) was dissolved in 2 ml of water and 2 ml of acetonitrile, 1.5 g of sodium iodide and 182 mg of 1-methyl-cyclopentano [b] 4-thiopyridone were added, and reacted at 65°-70° C. for about 5 hours while maintaining the pH of the reaction mixture to 6.5–7.0. After the completion of the reaction, to the suspended reaction mixture was added acetone with ice cooling, and the supernatant was removed. The residue was washed thoroughly with acetone, the precipitates were filtered off, suspended in water, then dissolved by adjusting the pH to 1.5, and purified by Diaion HP-20 column chromatography. The fractions containing the desired product was concentrated, and freeze dried to obtain 280 mg of the title compound.

NMR ($d_6$-DMSO-$D_2O$) δ: 2.41 (m, 2H), 3.07 (t, 2H), 3.40 (t, 2H), 3.59 (ABq, 2H), 4.31 (s, 3H), 4.45 (ABq, 2H), 5.09 (s, 2H), 5.14 (d, 1H), 5.77 (d, 1H), 6.08 (s, 1H), 6.73 (s, 1H), 8.02 (d, 1H), 8.47 (d, 1H).

EXAMPLE 64

(6R,7R)-7-[(Z)-2-(2-Aminothiazol-4-yl)-2-[(amino-thiazol-4-yl)methoxyimino]acetamido]-3-[(2,3-cyclopenteno-1-carboxymethylpyridinium-4-yl)thiomethyl]-ceph-3-em-4-carboxylic acid sodium salt The title compound was obtained in a manner similar to that in Example 63 except that 1-methyl-cyclopentano [b] 4-thiopyridone was replaced by 1-carboxymethyl-cyclopentano [b] 4-thiopyridone.

NMR ($D_2O$) δ: 2.27 (m, 2H), 2.95 (t, 2H), 3.17 (t, 2H), 3.56 (ABq, 2H), 4.29 (ABq, 2H), 4.92 (s, 2H), 5.05 (s, 2H), 5.16 (d, 1H), 5.75 (d, 1H), 6.76 (s, 1H), 6.93 (s, 1H), 7.63 (d, 1H), 8.16 (d, 1H).

EXAMPLE 65

(6R,7R)-7-[(Z)-2-(2-Aminothiazol-4-yl)-2-[(2-amino-thiazol-4-yl)methoxyimino]acetamido]-3-[(1-methyl-pyridinium-4-yl)thiomethyl]-ceph-3-em-4-carboxylate The title compound was obtained in a manner similar to that in Example 63 (e) except that the 1-methyl-cyclopentano [b] 4-thiopyridone was replaced by 1-methyl-4-thiopyridone.

NMR ($D_2O$-$d_6$-DMSO=1:2) δ: 3.62 (ABq, 2H), 4.48 (ABq, 2H), 4.62 (s, 3H), 5.12 (s, 2H), 5.16 (d, 1H), 5.80 (d, 1H), 6.75 (s, 1H), 7.02 (s, 1H), 8.01 (d, 2H), 8.55 (d, 2H).

EXAMPLE 66

(6R,7R)-7-[(Z)-2-(2-Aminothiazol-4-yl)-2-[(imidazol-4-yl)methoxyimino]acetamido]-3-[(2,3-cyclopenteno-1-methylpyridinium-4-yl)thiomethyl]-ceph-3-em-4-carboxylate 270 mg of (6R,7R)-7-[(Z)-2-(2-aminothiazol-4-yl)-2-[(imidazol-4-yl)methoxyimino]acetamido]-3-acetoxymethyl-ceph-3-em-4-carboxylic acid sodium salt was dissolved in a mixed solution of 2 ml of water and 1 ml of acetonitrile, 560 mg of sodium iodide and 100 mg of 1-methylcyclopentano [b] 4-thiopyridone were added thereto, the pH of the reaction mixture was adjusted to 6.8 with a 25% phosphoric acid aqueous solution, and a reaction was effected at 65° C. for 5 hours. After the completion of the reaction, the reaction mixture was added to 50 ml of acetone, the formed precipitates were filtered off, and purified by Diaion HP-20 column chromatography (eluted with 30% acetone-water). The fractions containing the desired product were concentrated, and freeze dried to obtain 60 mg of the title compound.

NMR ($d_6$-DMSO+$D_2O$) δ: 2.40 (m, 2H), 3.05 (t, 2H), 3.42 (t, 2H), 3.60 (ABq, 2H), 4.18 (s, 3H), 4.63 (ABq, 2H), 5.16 (d, 1H), 5.20 (s, 2H), 5.77 (d, 1H), 7.02 (s, 1H), 7.30 (s, 1H), 7.85 (s, 1H), 8.19 (d, 1H), 8.58 (d, 1H).

EXAMPLE 67

(6R,7R)-7-[(Z)-2-(2-Aminothiazol-4-yl)-2-[(imidazol-4-yl)methoxyimino]acetamido]-3-[(2,3-cyclopenteno-1-carboxymethylpyridinium-4-yl)thiomethyl]-ceph-3-em-4-carboxylic acid sodium salt The title compound was obtained in a manner similar to that in Example 66 except that the 1-methyl-cyclopentano [b] 4-thiopyridone was replaced by 1-carboxymethylcyclopentano [b] 4-thiopyridone.

NMR ($D_2O$) δ: 2.29 (m, 2H), 3.00 (t, 2H), 3.15 (t, 2H), 3.57 (ABq, 2H), 4.34 (ABq, 2H), 4.95 (s, 2H), 5.16 (d, 1H), 5.20 (s, 2H), 5.75 (d, 1H), 6.96 (s, 1H), 7.27 (s, 1H), 7.66 (d, 1H), 7.78 (s, 1H), 8.17 (d, 1H).

EXAMPLE 68

(6R,7R)-7-[(Z)-2-(2-Aminothiazol-4-yl)-2-[(imidazol-4-yl)methoxyimino]-3-[(1-methylpyridinium-4-yl)thiomethyl]-ceph-3-em-4-carboxylate The title compound was obtained in a manner similar to that in Example 66 except that the 1-methyl-cyclopentano [b]-4-thiopyridone was replaced by 1-methyl-4-thiopyridone.

NMR ($D_2O$-$CD_3OD$=2:1) δ: 3.55 (ABq, 2H), 4.13 (s, 3H), 4.26 (ABq, 2H), 5.08 (d, 1H), 5.20 (s, 2H), 5.72 (d, 1H), 7.20 (s, 1H), 7.46 (s, 1H), 7.69 (s, 1H), 7.78 (d, 2H), 8.35 (d, 2H).

EXAMPLE 69

(6R,7R)-7-[(Z)-2-(2-Aminothiazol-4-yl)-2-[(1,2,3-triazol-4-yl)methoxyimino]acetamido]-3-[(1-methylpyridinium-4-yl)thiomethyl]-ceph-3-em-4-carboxylate 194 mg of (6R,7R)-7-[(Z)-2-(2-aminothiazol-4-yl)-2-[(1,2,3-triazol-4-yl)methoxyimino]acetamido]-3-acetoxymethyl-ceph-3-em-4-carboxylic acid sodium salt was dissolved in 2 ml of water and 2 ml of acetonitrile, 400 mg of sodium iodide and 120 mg of 1-methyl-4-thiopyridone were added, the pH of the reaction mixture was adjusted to 6.8–7.0, and a reaction was effected to 65°–70° C. for 3.5 hours. After the completion of the reaction, the reaction mixture was added to acetone, the formed precipitates were filtered off, and purified by Diaion HP-20 column chromatography. The fractions containing the desired product were concentrated, and freeze dried to obtain 72 mg of the title compound.

NMR ($D_2O$-$d_6$-DMSO=5:1) δ: 3.55 (ABq, 2H), 4.21 (s, 3H), 4.33 (ABq, 2H), 5.11 (d, 1H), 5.40 (s, 2H), 5.74 (d, 1H), 7.03 (s, 1H), 7.84 (d, 2H), 8.42 (d, 2H).

EXAMPLE 70

(6R,7R)-7-[(Z)-2-(2-Aminothiazol-4-yl)-2-[(1,2,3-triazol-4-yl)methoxyimino]acetamido]-3-[(2,3-cyclopenteno-1-methylpyridinium-4-yl)thiomethyl]-ceph-3-em-4-carboxylate 196 mg of (6R,7R)-7-[(Z)-2-(2-aminothiazol-4-yl)-2-[(1,2,3-triazol-4-yl)methoxyimino]acetamido]-3-acetoxymethyl-ceph-3-em-4-carboxylic acid sodium salt was dissolved in a mixed solution of 2 ml of water and 2 ml of acetonitrile, 540 mg of sodium iodide and 72 mg of 1-methyl-cyclopentano-[b]-4-thiopyridine were added, and reacted at 75° C. for 7 hours. After the completion of the reaction, the reaction mixture was concentrated under reduced pressure, then poured into acetone, and the formed precipitates were filtered off. They were dissolved in water at pH 2 and purified by Diaion HP-20 column chromatography. The fractions containing the desired product were concentrated, adjusted to pH 7–8 with a saturated sodium bicarbonate aqueous solution, and again purified by Diaion HP-20 column chromatography. The fractions containing the desired product were concentrated, and freeze dried to obtain 102 mg of the title compound.

NMR ($CD_3OD$-$d_6$-DMSO) δ: 2.19 (m, 2H), 2.86 (m, 2H), 3.20 (m, 2H), 3.36 (ABq, 2H), 4.01 (s, 3H), 4.47 (ABq, 2H), 4.94 (d, 1H), 5.15 (s, 2H), 5.55 (d, 1H), 7.19 (s, 1H), 8.20 (d, 1H), 8.42 (s, 1H).

EXAMPLE 71

(6R,7R)-7-[(Z)-2-(2-Aminothiazol-4-yl)-2-[(1,2,4-triazol-3-yl)methoxyimino]acetamido]-3-[(1-methylpyridinium-4-yl)thiomethyl]-ceph-3-em-4-carboxylate The title compound was obtained in a manner similar to that in Example 70 except that the 1-methyl-cyclopentano[b]-4-thiopyridone was replaced by 1-methyl-4-thiopyridone.

NMR ($D_2O$) δ: 3.64 (ABq, 2H), 4.27 (s, 3H), 4.28 (ABq, 2H), 5.29 (d, 1H), 5.48 (s, 2H), 5.85 (d, 1H), 7.09 (s, 1H), 7.90 (d, 2H), 8.41 (d, 2H), 8.46 (s, 1H).

EXAMPLE 72

(6R,7R)-7-[(Z)-2-(2-Aminothiazol-4-yl)-2-(N-methylcarbamoylmethoxyimino)acetamido]-3-[(2,3-cyclopenteno-1-methylpyridinium-4-yl)thiomethyl]-ceph-3-em-4-carboxylate 534 mg of (6R,7R)-7-[(Z)-2-(2-aminothiazol-4-yl)-2-(N-methylcarbamoylmethoxyimino)acetamido]-3-acetoxymethyl-ceph-3-em-4-carboxylic acid sodium salt was dissolved in 2 ml of acetonitrile and 2 ml of water, 1.5 g of sodium iodide and 180 mg of 1-methyl-cyclopentano[b]-4-thiopyridone were added, and reacted at 65°–70° C. for 7 hours while adjusting the pH of the reaction mixture to 6.5 or in its vicinity. After the completion of the reaction, the reaction mixture was treated in a manner similar to that in Example 34, the formed precipitates were dissolved in a small quantity of water, and purified by Diaion HP-20 column chromatography (the desired product being eluted with 20% acetone-water). The fractions containing the desired product were concentrated, and freeze dried to obtain 360 mg of the title compound.

NMR (D$_2$O) δ: 2.32 (m, 2H), 2.81 (s, 3H), 3.00 (t, 2H), 3.28 (t, 2H), 3.64 (ABq, 2H), 4.07 (s, 3H), 4.31 (ABq, 2H), 4.74 (s, 2H), 5.22 (d, 1H), 5.81 (d, 1H), 7.09 (s, 1H), 7.63 (d, 1H), 8.23 (d, 1H).

EXAMPLE 73

(6R,7R)-7-[(Z)-2-(2-Aminothiazol-4-yl)-2-(carbamoylmethoxyimino)acetamido]-3-[(2,3-cyclopenteno-1-carboxymethylpyridinium-4-yl)thiomethyl]-ceph-3-em-4-carboxylic acid sodium salt 520 mg of (6R,7R)-7-[(Z)-2-(2-aminothiazol-4-yl)-2-(carbamoylmethoxyimino)acetamido]-ceph-3-em-4-carboxylic acid sodium salt was dissolved in 2.4 ml of water and 1.2 ml of acetonitrile, 1.5 g of sodium iodide and 228 mg of 1-carboxymethyl-cyclopentano[b]4-thiopyridone were added, and reacted at 65°-70° C. for 4 hours while adjusting the pH of the reaction mixture to 6.5-7.0. After the completion of the reaction, the reaction mixture was added dropwise to acetone, the formed precipitates were dissolved in a small quantity of water, and purified by Diaion HP-20 column chromatography. The fractions containing the desired compound were concentrated, and freeze dried to obtain 250 mg of the title compound.

NMR (D$_2$O) δ: 2.34 (m, 2H), 3.03 (t, 2H), 3.20 (t, 2H), 3.64 (ABq, 2H), 4.34 (ABq, 2H), 4.75 (s, 2H), 4.96 (s, 2H), 5.22 (d, 1H), 5.85 (d, 1H), 7.14 (s, 1H), 7.64 (d, 1H), 8.21 (d, 1H).

EXAMPLE 74

(6R,7R)-7-[(Z)-2-(2-Aminothiazol-4-yl)-2-methoxyiminoacetamido]-3-[(2,3-cyclopenteno-1-cyclopropylpyridinium-4-yl)thiomethyl]-ceph-3-em-4-carboxylate 240 mg of (6R,7R)-7-[(Z)-2-(2-aminothiazol-4-yl)-2-methoxyiminoacetamido]-3-acetoxymethyl-ceph-3-em-4-carboxylic acid sodium salt was dissolved in 4 ml of a 1:1 mixed solution of acetonitrile and water, 120 mg of 1-cyclopropyl-cyclopentano[b]4-thiopyridone and 750 mg of sodium iodide were added, the pH was adjusted with a saturated sodium bicarbonate aqueous solution to 6.5-7.0, and a reaction was effected at 65°-70° C. for 9 hours. The reaction mixture was added dropwise to 50 ml of acetone, the formed precipitates were filtered off, they were dissolved in a small quantity of water, and purified by Diaion HP-20 column chromatography (eluted with 20% acetone-water), and freeze dried to obtain 155 mg of the title compound.

NMR (D$_2$O) δ: 1.26 (m, 2H), 1.33 (m, 2H), 2.31 (m, 2H), 2.92 (t, 2H), 3.40 (t, 2H), 3.60 (ABq, 2H), 3.89 (m, 1H), 3.99 (s, 3H), 4.29 (ABq, 2H), 5.18 (d, 1H), 5.75 (d, 1H), 6.96 (s, 1H), 7.59 (d, 1H), 8.27 (d, 1H).

EXAMPLE 75

(6R,7R)-7-[(Z)-2-(2-Aminothiazol-4-yl)-2-methoxyiminoacetamido]-3-[(1-cyclopropylpyridinium-4-yl)thiomethyl]-ceph-3-em-4-carboxylate 1.43 g of (6R,7R)-7-[(Z)-2-(2-aminothiazol-4-yl)-2-methoxyiminoacetamido]-3-acetoxymethyl-ceph-3-em-4-carboxylic acid sodium salt was dissolved in 5 ml of acetonitrile and 8 ml of water, 4.5 g of sodium iodide, and 540 mg of 1-cyclopropyl-4-thiopyridone dissolved in 3 ml of acetonitrile were added thereto, the pH was adjusted to 6.5-7.0 with a saturated sodium bicarbonate aqueous solution, and a reaction was effected at 65°-70° C. for 10 hours. After the completion of the reaction, the reaction mixture was added dropwise to 200 ml of acetone, and the formed precipitates were filtered off. They were dissolved in a small quantity of water, purified by Diaion HP-20 column chromatography (eluted with 10% acetone-water) and Sephadex LH-20 (50% methanol-water), and freeze dried to obtain 720 mg of the title compound.

NMR (D$_2$O-CD$_3$OD=1:1) δ: 1.31 (m, 2H), 1.33 (m, 2H), 3.57 (ABq, 2H), 3.97 (s, 3H), 4.12 (m, 1H), 4.35 (ABq, 2H), 5.14 (d, 1H), 5.75 (d, 1H), 6.90 (s, 1H), 7.85 (d, 2H), 8.57 (d, 2H).

EXAMPLE 76

(6R,7R)-7-[(Z)-2-(2-Aminothiazol-4-yl)-2-methoxyiminoacetamido]-3-[2,3-cyclopenteno-1-(2,2,2-trifluoroethyl)pyridinium-4-yl]thiomethyl-ceph-3-em-4-carboxylate 810 mg of (6R,7R)-7-[(Z)-2-(2-aminothiazol-4-yl)-2-methoxyiminoacetamido]-3-acetoxymethyl-ceph-3-em-4-carboxylic acid sodium salt was dissolved in 3 ml of acetonitrile and 3 ml of water, 2.55 g of sodium iodide and 500 mg of 1-(2,2,2-trifluoroethyl)-cyclopentano[b]4-thiopyridone were added thereto, and reacted at 70° C. for 10 hours while adjusting the pH of the reaction mixture to 6.5-7.0.

After the completion of the reaction, the reaction mixture was poured into 100 ml of acetone, the formed precipitates were dissolved in a small quantity of water, then purified by Diaion HP-20 column chromatography (eluted with 20% acetone-water), further purified by Sephadex LH-20 (50% methanol-water), and freeze dried to obtain 80 mg of the title compound.

NMR (D$_2$O) δ: 2.34 (m, 2H), 3.02 (t, 2H), 3.37 (t, 2H), 3.61 (ABq, 2H), 3.99 (s, 3H), 4.34 (ABq, 2H), 5.20 (d, 1H), 5.25 (q, 2H), 5.79 (d, 1H), 7.01 (s, 2H), 7.73 (d, 1H), 8.36 (d, 1H).

EXAMPLE 77

(6R,7R)-7-[(Z)-2-(2-Aminothiazol-4-yl)-2-(vinyloxyimino)acetamido]-3-[(2,3-cyclopenteno-1-carboxymethylpyridinium-4-yl)thiomethyl]-ceph-3-em-4-carboxylate sodium salt 195 mg of (6R,7R)-7-[(Z)-2-(2-aminothiazol-4-yl)-2-(vinyloxyimino)acetamido]-3-acetoxymethyl-ceph-3-em-4-carboxylic acid sodium salt was dissolved in 1.5 ml of acetonitrile and 1.5 ml of H$_2$O, 110 mg of 1-carboxymethyl-cyclopentano[b]4-thiopyridone and 600 mg of sodium iodide were added thereto, the pH of the reaction mixture was adjusted to 6.5-7.0, and reacted at 70° C. for 5 hours. After the completion of the reaction, the reaction mixture was added dropwise to 30 ml of acetone, and the formed precipitates were filtered off. They were dissolved in a small quantity of water, purified by Diaion HP-20 column chromatography (eluted with 5-10% acetone-water) and freeze dried to obtain 55 mg of the title compound.

NMR (D$_2$O) δ: 2.29 (m, 2H), 2.98 (t, 2H), 3.17 (t, 2H), 3.62 (ABq, 2H), 4.31 (ABq, 2H), 4.39 (m, 1H), 4.81 (m, 1H), 4.93 (s, 2H), 5.23 (d, 1H), 5.80 (d, 1H), 7.01 (q, 1H), 7.10 (s, 1H), 7.62 (d, 1H), 8.18 (d, 1H).

EXAMPLE 78

(6R,7R)-7-[(Z)-2-(2-Aminothiazol-4-yl)-2-(difluoromethoxyimino)acetamido]-3-[(2,3-cyclopenteno-1-carboxymethylpyridinium-4-yl)thiomethyl]-ceph-3-em-4-carboxylate sodium salt 128 mg of (6R,7R)-7-[(Z)-2-(2-aminothiazol-4-yl)-2-(difluoromethoxyimino)actamido]-3-acetoxymethyl-ceph-3-em-4-carboxylic acid sodium salt (synthesized by the process described by Japanese patent application laid-open No. 53686/1981) and 68 mg of 1-carboxymethyl-cyclopentano[b]-4-thiopyridone were added to 2 ml of water, and the pH was adjusted with a saturated sodium bicarbonate aqueous solution to make a transparent solution. Thereafter, 385 mg of sodium iodide was added, and stirred at 60°–70° C. for 6.5 hours. The reaction mixture was diluted with water, and, after adjusting the pH to 7.5 with a saturated sodium bicarbonate aqueous solution, adsorbed to 30 ml of Diaion HP-20, which was then washed with 100 ml of water and 100 ml of 5% acetone-water, and the desired product was eluted with 10–15% acetone-water and freeze dried to obtain 21 mg of the title compound.

NMR ($D_2O$) δ: 2.23–2.38 (m, 2H), 2.93–3.03 (m, 2H), 3.13–3.23 (m, 2H), 3.50 (d, 1H), 3.76 (d, 1H), 4.21 (d, 1H), 4.44 (d, 1H, J=14 Hz), 5.94 (s, 2H), 5.23 (d, 1H), 5.80 (d, 1H), 6.93 (t, 1H), 7.21 (s, 1H), 7.59 (d, 1H), 8.18 (d, 1H).

EXAMPLE 79

(6R,7R)-7-[(Z)-2-(2-Aminothiazol-4-yl)-2-(cyclopropylmethoxyimino)acetamido]-3-[(2,3-cyclopenteno-1-carboxymethylpyridinium-4-yl)thiomethyl]-ceph-3-em-4-carboxylate sodium salt 520 mg of (6R,7R)-7-[(Z)-2-(2-aminothiazol-4-yl)-2-(cyclopropylmethoxyimino)acetamido]-3-acetoxymethyl-ceph-3-em-4-carboxylic acid sodium salt was dissolved in 1 ml of acetonitrile and 2 ml of water, 1.5 g of sodium iodide and 250 mg of 1-carboxymethyl-cyclopentano[b]-4-thiopyridone were added thereto, the pH of the reaction mixture was adjusted to 6.5–7.0, and reacted at 65°–70° C. for 4 hours. After the completion of the reaction, the reaction mixture was poured into 60 ml of acetone, and the formed precipitates were filtered off. They were dissolved in a small quantity of water, purified by Diaion HP-20 column chromatography (eluted with 10% acetone-water), and freeze dried to obtain 190 mg of the title compound.

NMR ($D_2O$) δ:
0.34 (m, 2H), 0.60 (m, 2H), 1.25 (m, 1H), 2.33 (m, 2H), 3.03 (t, 2H), 3.20 (t, 2H), 3.63 (ABq, 2H), 4.06 (d, 2H), 4.33 (ABq, 2H), 4.95 (s, 2H), 5.21 (d, 1H), 5.83 (d, 1H), 7.03 (s, 1H), 7.64 (d, 1H), 8.21 (d, 1H).

EXAMPLE 80

(a) Diphenylmethyl (6R,7R)-3-bromomethyl-7-[(Z)-2-(2-tritylaminothiazol-4-yl)-2-methoxyiminoacetamido]-ceph-3-em-4-carboxylate 120 mg (0.24 mmol) of diphenylmethyl 7-amino-3-bromomethyl-ceph-3-em-4-carboxylate hydrochloride and 120 mg (0.27 mmol) of (Z)-2-(2-tritylaminothiazol-4-yl)-2-methoxyiminoacetic acid were dissolved in 2.4 ml of methylene chloride. 98 μl (1.2 mmol) of pyridine and 24 μl (0.27 mmol) of phosphorus oxychloride were added threreto with ice cooling, and reacted for 10 minutes.

After the reaction, 12 ml of chloroform was added, the reaction mixture was washed with 6 ml of water twice, dried on magnesium sulfate, and the solvent was removed, followed by purification by silica gel chromatography using benzene-ethyl acetate (20:1) to obtain 190 mg (90%) of the title compound.

NMR ($CDCl_3$) δ:
3.55 (bs, 2H), 4.05 (s, 3H), 4.35 (bs, 2H), 5.05 (d, 1H, J=4), 5.90 (dd, 1H, J=4 J=8), 6.75 (s, 1H), 6.95 (s, 1H), 7.1–7.8 (m, 26H).

(b) Diphenylmethyl (6R,7R)-7-[(Z)-2-(2-tritylaminothiazol-4-yl)-2-methoxyiminoacetamido]-3-[1-(2,2,2-trifluoroethylpyridinium-4-yl)thiomethyl]-ceph-3-em-4-carboxylate iodide 266 mg (0.3 mmol) of diphenylmethyl (6R,7R)-3-bromomethyl-7-[(Z)-2-(2-tritylaminothiazol-4-yl)-2-methoxyiminoacetamido]-ceph-3-em-4-carboxylate was dissolved in 2.66 ml of DMF, 63 mg (0.36 mmol) of 1-(2,2,2-trifluoroethyl)-4-pyridothione and 90 mg (0.6 mmol) of sodium iodide were added, and reacted at room temperature for 15 minutes. After the reaction, 15 ml of ethyl acetate was added, the reaction mixture was washed with 1N hydrochloric acid, then with water, dried on magnesium sulfate, and the solvent was removed to obtain 320 mg of the title compound. This was used in the next reaction without purification.

(c) (6R,7R)-7-[(Z)-2-(2-Aminothiazol-4-yl)-2-methoxyiminoacetamido]-3-[1-(2,2,2-trifluoroethylpyridinium-4-yl)thiomethyl]-ceph-3-em-4-carboxylate 320 mg of diphenylmethyl (6R,7R)-7-[(Z)-2-(2-tritylaminothiazol-4-yl)-2-methoxyiminoacetamido]-3-[1-(2,2,2-trifluoroethylpyridinium-4-yl)thiomethyl]-ceph-3-em-4-carboxylate iodide was dissolved in 0.96 ml of anisole, 3.2 ml of trifluoroacetic acid was added with ice cooling, and reacted for 40 minutes. After the reaction, isopropyl ether was added to induce precipitation. The precipitates were dried to obtain 260 mg of a powder. After adding 2.6 ml of water thereto and adjusting the pH to 7.8 with $NaHCO_3$, this was purified with Diaion HP-20 resin (methanol:$H_2O$=1:1) to obtain 120 mg of the title compound.

NMR ($D_2O$) δ: 3.50, 3.83 (ABq, 2H, J=18 Hz), 4.03 (s, 3H), 4.30, 4.53 (ABq, 2H, J=14 Hz), 5.25 (d, 1H, J=6 Hz), 5.30, 5.46 (ABq, 2H, J=6 Hz), 5.80 (d, 1H, J=6 Hz), 7.00 (s, 1H), 7.97 (d, 2H, J=6 Hz), 8.60 (d, 2H, J=6 Hz).

EXAMPLE 81

Diphenylmethyl (6R,7R)-7-[(Z)-2-(2-tritylaminothiazol-4-yl)-2-ethoxyiminoacetamido]-3-[1-(2,2,2-trifluoroethylpyridinium-4-yl)thiomethyl]-ceph-3-em-4-carboxylate iodide 135 mg (0.15 mmol) of the 3-bromomethyl form synthesized in a manner similar to that in Example 80 was dissolved in 1.35 ml of DMF, 32 mg (0.18 mmol) of 1-(2,2,2-trifluoroethyl)-4-pyridothione and 30 mg (0.2 mmol) of sodium iodide were added, and reacted at room temperature for 15 minutes. After the reaction, 7.5 ml of ethyl acetate was added to the reaction mixture, which was washed with water, then with 1N hydrochloric acid, dried on magnesium sulfate, and the solvent was removed to obtain 170 mg of the title compound. This was used in the next reaction without purification.

(6R,7R)-7-[(Z)-2-(2-Aminothiazol-4-yl)-2-ethoxyiminoacetamido]-3-[1-(2,2,2-trifluoroethylpyridinium-4-yl)thiomethyl]-ceph-3-em-4-carboxylate 170 mg of diphenylmethyl (6R,7R)-7-[(Z)-2-(2-tritylaminothiazol-4-yl)-2-ethoxyiminoacetamido]-3-[1-(2,2,2-trifluoroethylpyridinium-4-yl)thiomethyl]-ceph-3-em-4-carboxylate iodide was dissolved in 0.51 ml of anisole, 1.7 ml of trifluoroacetic acid was added with ice cooling, and reacted for 40 minutes. After the reaction, isopropyl ether was added to induce precipitation. The precipitates were dried to obtain 110 mg of a powder. After adding 1.1 ml of water thereto and adjusting the pH to 7.8 with NaHCO₃, this was purified with Diaion HP-20 resin (methanol:H₂O=1:1) to obtain 65 mg of the title compound.

NMR (D₂O) δ: 1.36 (t, 3H, J=6 Hz), 3.50, 3.25 (ABq, 2H, J=18 Hz), 4.20–4.55 (4H), 5.20–5.60 (3H), 5.85 (d, 1H, J=6 Hz), 7.00 (s, 1H), 8.00 (d, 2H, J=7 Hz), 8.63 (d, 2H, J=7 Hz).

EXAMPLE 82

Diphenylmethyl (6R,7R)-7-[(Z)-2-(2-tritylaminothiazol-4-yl)-2-(diphenylmethoxycarbonylmethoxyimino)actamido]-3-[1-(2,2,2-trifluoroethylpyridinium-4-yl)thiomethyl]-ceph-3-em-4-carboxylate iodide 180 mg (0.164 mmol) of the 3-bromomethyl form synthesized in a manner similar to that in Example 80 was dissolved in 1.8 ml of DMF, 31 mg (0.18 mmol) of 1-(2,2,2-trifluoroethyl)-4-pyridothione and 30 mg (0.2 mmol) of sodium iodide were added, and reacted at room temperature for 15 minutes. After the reaction, 8.2 ml of ethyl acetate was added to the reaction mixture, which was washed with 1N hydrochloric acid, then with water, dried on magnesium sulfate, and the solvent removed to obtain 200 mg of the title compound. This was used in the next reaction without purification.

(6R,7R)-7-[(Z)-2-(2-Aminothiazol-4-yl)-2-(carboxymethoxyimino)acetamido]-3-[1-(2,2,2-trifluoroethylpyridinium-4-yl)thiomethyl]-ceph-3-em-4-carboxylic acid sodium salt 200 mg of diphenylmethyl (6R,7R)-7-[2-(2-tritylaminothiazol-4-yl)-2-diphenylmethoxycarbonylmethoxyiminoacetamido]-3-[1-(2,2,2-trifluoroethylpyridinium-4-yl)thiomethyl]-ceph-3-em-4-carboxylate iodide was dissolved in 0.6 ml of anisole, 2.0 ml of trifluoroacetic acid was added thereto with ice cooling, and reacted for 40 minutes. After the reaction, isopropyl ether was added to induce precipitation. The precipitates were dried to obtain 120 mg of a powder. After adding 1.2 ml of water thereto and adjusting the pH to 7.8 with NaHCO₃, this was purified with Diaion HP-20 resin (methanol:H₂O=1:4) to obtain 70 mg of the title compound.

NMR (D₂O) δ: 3.50, 3.83 (ABq, 2H, J=18 Hz), 4.40 (s, 2H), 4.63 (s, 2H), 5.26, 5.45 (ABq, 2H, J=9 Hz), 5.28 (d, 1H, J=6 Hz), 5.80 (d, 1H, J=6 Hz), 7.00 (s, 1H), 8.00 (d, 2H, J=7 Hz), 8.56 (d, 2H, J=7 Hz).

EXAMPLE 83

Diphenylmethyl (6R,7R)-7-[(Z)-2-(2-tritylaminothiazol-4-yl)-2-(diphenylmethoxycarbonylprop-2-oxyimino)acetamido]-3-[1-(2,2,2-trifluoroethylpyridinium-4-yl)thiomethyl]-ceph-3-em-4-carboxylate iodide 250 mg (0.22 mmol) of the 3-bromoethyl form synthesized in a manner similar to that in Example 80 was dissolved in 2.5 ml of DMF, 44 mg (0.25 mmol) of 1-(2,2,2-trifluoroethyl)-4-pyridothione and 45 mg (0.3 mmol) of sodium iodide were added, and reacted at room temperature for 15 minutes. After the reaction, 6.6 ml of ethyl acetate was added to the reaction mixture, which was washed with water, then with 1N hydrochloric acid, dried on magnesium sulfate, and the solvent removed to obtain 300 mg of the title compound. This was used in the next reaction without purification.

(6R,7R)-7-[(Z)-2-(2-Aminothiazol-4-yl)-2-(carboxyprop-2-oxyimino)acetamido]-3-[1-(2,2,2-trifluoroethylpyridinium-4-yl)thiomethyl]-ceph-3-em-4-carboxylic acid sodium salt 300 mg of diphenylmethyl (6R,7R)-7-[(Z)-2-(2-tritylaminothiazol-4-yl)-2-diphenylmethoxycarbonylprop-2-oxyiminoacetamido]-3-[1-(2,2,2-trifluoroethylpyridinium-4-yl)thiomethyl]-ceph-3-em-4-carboxylate iodide was dissolved in 0.9 ml of anisole, 3 ml of trifluoroacetic acid was added with ice cooling, and reacted for 40 minutes. After the reaction, isopropyl ether was added to induce precipitation. The precipitates were dried to obtain 170 mg of a powder. After adding 1.7 ml of water thereto and adjusting the pH to 7.8 with NaHCO₃, this was purified with Diaion HP-20 resin (methanol:H₂O=1:4) to obtain 100 mg of the title compound.

NMR (D₂O) δ: 1.56 (s, 6H), 3.53, 3.83 (ABq, 2H, J=18 Hz), 4.40 (s, 2H), 5.26, 5.43 (ABq, 2H, J=9 Hz), 5.30 (d, 1H, J=6 Hz), 5.83 (d, 1H, J=6 Hz), 6.95 (s, 1H), 8.00 (d, 2H, J=7 Hz), 8.60 (d, 2H, J=7 Hz).

EXAMPLE 84

Diphenylmethyl (6R,7R)-3-bromomethyl-7-[(Z)-2-(2-tritylaminothiazol-4-yl)-2-methoxyiminoacetamido]-ceph-3-em-4-carboxylate 120 mg (0.24 mmol) of diphenylmethyl (6R,7R)-7-amino-3-bromomethyl-ceph-3-em-4-carboxylate hydrochloride and 120 mg (0.27 mmol) of (Z)-2-(2-tritylaminothiazol-4-yl)-2-methoxyiminoacetic acid were dissolved in 2.4 ml of methylene chloride, then 98 μl (1.2 mmol) of pyridine and 24 μl (0.27 mmol) of phosphorus oxychloride were added thereto with ice cooling, and reacted for 10 minutes. After the reaction, 12 ml of chloroform was added to the reaction mixture, which was washed with 6 ml of water twice, dried on magnesium sulfate, and the solvent was distilled off. The residue was purified by silica gel chromatography (benzene-ethyl acetate (20:1)) to obtain 190 mg of the title compound.

NMR (D₂O) δ: 3.55 (bs, 2H), 4.05 (s, 3H), 4.35 (bs, 2H), 5.05 (d, 1H, J=4 Hz), 5.90 (dd, 1H, J=4 Hz, 8 Hz), 6.75 (s, 1H), 6.95 (s, 1H), 7.1–7.8 (m, 26H).

Diphenylmethyl (6R,7R)-7-[(Z)-2-(2-tritylaminothiazol-4-yl)-2-methoxyiminoacetamido]-3-[1-(2-fluoroethylpyridinium-4-yl)thiomethyl]-ceph-3-em-4-carboxylate iodide 130 mg (0.15 mmol) of diphenylmethyl (6R,7R)-3-bromomethyl-7-[(Z)-2-(2-tritylaminothiazol-4-yl)-2-methoxyiminoacetamido]-ceph-3-em-4-carboxylate was dissolved in 1.3 ml of DMF, 28 mg (0.18 mmol) of 1-(2-fluoroethyl)-4-pyridothione and 44 mg (0.3 mmol) of sodium iodide were added, and reacted to room temperature for an hour. After the reaction, the DMF was distilled under reduced pressure, and isopropyl ether was added to induce precipitation. The precipitates were purified by silica gel chromatography (chloroform-methanol (10:1)) to obtain 150 mg of the title compound.

NMR (CDCl$_3$) δ: 3.40–6.00 (m, 10H), 4.00 (s, 3H), 6.70 (s, 1H), 6.91 (s, 1H), 7.16–7.50 (m, 26H), 7.65 (d, 2H, J=6 Hz), 8.70 (d, 2H, J=6 Hz).

(6R,7R)-7-[(Z)-2-(2-Aminothiazol-4-yl)-2-methoxyiminoacetamido]-3-[1-(2-fluoroethylpyridinium-4-yl)thiomethyl]-ceph-3-em-4-carboxylate 150 mg of diphenylmethyl (6R,7R)-7-[(Z)-2-(2-aminothiazol-4-yl)-2-methoxyiminoacetamido]-3-[1-(2-fluoroethylpyridinium-4-yl)thiomethyl]-ceph-3-em-4-carboxylate iodide was dissolved in 0.45 ml of anisole, 1.5 ml of trifluoroacetic acid was added with ice cooling, and reacted for an hour. After the reaction, isopropyl ether was added to induce precipitation. The precipitates were dried to obtain 100 mg of a powder. After adding 1 ml of water thereto and adjusting the pH to 7.8 with NaHCO$_3$, this was purified with Diaion HP-20 resin (methanol:H$_2$O=1:1) to obtain 50 mg of the title compound.

NMR (D$_2$O) δ: 3.57, 3.88 (ABq, 2H, J=18 Hz), 4.10 (s, 3H), 4.30, 4.57 (ABq, 2H, J=13 Hz), 4.77–5.67 (m, 4H), 5.30 (d, 1H, J=5 Hz), 5.88 (d, 1H, J=5 Hz), 7.09 (s, 1H), 7.96 (d, 2H, J=8 Hz), 8.63 (d, 2H, J=8 Hz).

The desired compounds (I) of this invention and salts thereof are novel compounds and exhibit high anti-bacterial activity inhibiting the growth of a wide range of pathogenic microorganisms including Gram positive and negative bacteria. To demonstrate the effectiveness of the desired compounds (I), antibacterial activity measured on representative examples of these compounds (I) of this invention is shown in Tables 1 and 2.

TABLE 1

| Compound of Example | Minimum Growth Inhibitory Concentration (MIC) mcg/ml Test Bacterium | | | | | | | | | | |
|---|---|---|---|---|---|---|---|---|---|---|---|
| | 1 | 2 | 3 | 4 | 5 | 6 | 7 | 8 | 9 | 10 | 11 |
| 1 | 0.20 | 1.56 | ≦0.025 | ≦0.025 | 0.39 | 1.56 | 0.05 | 12.5 | | | |
| 2 | 0.05 | 1.56 | ≦0.025 | ≦0.025 | 0.10 | 0.78 | 0.05 | 6.25 | | | |
| 4 | 0.10 | 0.20 | 0.10 | 0.10 | 0.20 | 0.78 | 0.10 | 6.25 | | | |
| 12 | 3.13 | 12.5 | 1.56 | 0.78 | 1.56 | 6.25 | 1.56 | 50 | | | |
| 18 | 1.56 | 12.5 | 0.20 | 0.39 | 0.10 | 6.25 | 0.05 | 6.25 | | | |
| 34 | 0.78 | 1.56 | ≦0.025 | ≦0.025 | | | 0.05 | 6.25 | 6.25 | 0.10 | 0.20 |
| 35 | 0.10 | 0.20 | 0.10 | 0.05 | | | 0.10 | 12.5 | 0.20 | 0.39 | 0.20 |
| 39 | 0.78 | 1.56 | ≦0.025 | ≦0.025 | | | ≦0.025 | 12.5 | 6.25 | 0.20 | 0.10 |
| 51 | 1.56 | 0.05 | 0.10 | ≦0.025 | | | ≦0.025 | 6.25 | 1.56 | ≦0.025 | 0.05 |

Test Bacterium
1. *Staphylococcus aureus* 209PJC-1
2. *Bacillus subtilis*
3. *Escherichia coli* RGN 823
4. *Klebsiella pneumoniae* GN 69
5. *Proteus vulgaris* OX-19
6. *Enterobacter cloacae* G-0006
7. *Serratia marcescens* N 01
8. *Pseudomonas aeruginosa* MB 3833
9. *Streptococcus faecalis* ATCC 8043
10. *Proteus vulgaris* GN 76
11. *Enterobacter cloacae* G-0005

TABLE 2

| Compound of Example | Minimum Growth Inhibitory Concentration (MIC) mcg/ml Test Bacterium | | | | | | | | | | |
|---|---|---|---|---|---|---|---|---|---|---|---|
| | 1 | 2 | 3 | 4 | 5 | 6 | 7 | 8 | 9 | 10 | 11 |
| 27 | 1.56 | 0.78 | 1.56 | 0.20 | 0.025 | 0.2 | 0.025 | 0.05 | 0.39 | 0.05 | |
| 28 | 0.78 | 0.39 | 0.78 | 0.39 | 0.05 | 0.39 | 0.10 | 0.10 | 1.56 | 0.20 | |
| 29 | 0.78 | 0.39 | 0.39 | 0.39 | 0.10 | 0.79 | 0.20 | 0.20 | 3.13 | 0.39 | |
| 30 | 25 | 12.5 | 25 | 1.56 | 0.10 | 0.05 | 0.10 | 0.05 | 0.20 | 0.10 | |
| 31 | 3.13 | 3.13 | 6.25 | 0.39 | 0.20 | 0.78 | 0.20 | 1.56 | 0.78 | 0.39 | |
| 32 | 1.56 | 1.56 | 0.39 | 0.78 | 0.20 | 3.13 | 0.39 | 0.78 | 0.39 | 0.78 | |
| 33 | 1.56 | 0.78 | 0.05 | 0.78 | 0.05 | 0.39 | 0.05 | 0.39 | 6.25 | 0.10 | |
| 80 | 0.20 | 0.20 | 0.20 | 0.05 | 0.20 | 1.56 | 0.20 | 0.78 | 0.20 | | 0.20 |
| 81 | 0.39 | 0.39 | 0.05 | ≦0.025 | 0.10 | 0.78 | 0.05 | 0.39 | 0.10 | | 0.05 |
| 82 | 3.13 | 3.13 | 0.05 | 0.05 | ≦0.025 | 0.05 | <0.025 | 0.05 | <0.025 | | <0.025 |
| 83 | 6.25 | 3.13 | 0.20 | 0.20 | 0.20 | 0.39 | 0.05 | 0.20 | 0.20 | | 0.05 |

TABLE 2-continued

| Compound of Example | Minimum Growth Inhibitory Concentration (MIC) mcg/ml Test Bacterium | | | | | | | | | | |
|---|---|---|---|---|---|---|---|---|---|---|---|
| | 1 | 2 | 3 | 4 | 5 | 6 | 7 | 8 | 9 | 10 | 11 |
| 84 | 0.20 | 0.20 | 0.05 | <0.025 | 0.10 | 0.39 | 0.05 | 0.20 | 0.10 | | 0.025 |

Test Bacterium
1. *Staphylococcus aureus* Smith
2. *Staphylococcus aureus* 209 PJC-1
3. *Escherichia coli* NIHJ JC-2
4. *Eshcerichia coli* GN 206
5. *Klebsiella pneumoniae* PCI 602
6. *Proteus mirabilis* GN 79
7. *Salmonella typhimurium* LT-2
8. *Proteus vulgaris* GN 76
9. *Proteus rettgeri* GN-624
10. *Serratia marcescens* No. 2
11. *Serratia marcescens* No. 1

The merits of the administration of the invented compound to the animal body are clearly demonstrated by the serum concentration, the treatment of experimental infection and the toxicity test described below.

The compounds of Examples 27, 28, 34, and 51 of this invention show the serum concentrations set forth in Table 3. The experiment was conducted by using 3 mice (average body weight 20 g) in each group, subcutaneously administering 25 mg/kg of the sample, taking blood samples at predetermined intervals, separating the serum and measuring the sample concentration by an antibacterial activity test using *Escherichia coli* as a testing bactera.

TABLE 3

| Compound of Example | Serum Concentration (μg/ml) | | | |
|---|---|---|---|---|
| | 1/12 | ¼ | ½ | 1 (hr) |
| 27 | 20 | 28 | 12.5 | 2.2 |
| 28 | 26 | 31 | 28.5 | 4 |
| 34 | 25 | 35 | 21 | 6.4 |
| 51 | 27 | 34 | 24 | 5.4 |

The results of the treatment of experimental infection on the compounds of Examples 28, 34, and 51 are as set forth in Table 4. The experiment was conducted by intraperitoneally inoculating groups of 8 mice in each group with a Cephalosporinase-producing *Escherichia coli* GN206 (inoculum size: $1.25 \times 10^6$ CFU/mouse), subcutaneously administering the sample compound one hour after the infection, and observing one week later the number of survivals.

TABLE 4

| Infection Treatment Experiment (*Escherichia coli* GN206) | |
|---|---|
| Compound of Example | ED$_{50}$ (mg/mouse) |
| 28 | 0.065 |
| 34 | 0.3 |
| 51 | 0.37 |

For example, with the compound of Example 28 used in this experiment, while its minimum growth inhibitory concentration (MIC) against the test bacterium *Escherichia coli* GN206 is 0.39 μg/ml, its ED$_{50}$ value is 0.065 mg/mouse, which clearly demonstrates the high infection treatment effect of this compound.

Further, the compound of Example 28 was intravenously adminstered to 3 mice at a dose of 1 g/kg and also the compounds of Examples 34 and 51 were similarly administered at a dose of 3 g/kg respectively, and the number of survivor was examined after a week. As a result, all the mice survived, and it indicates that the LD$_{50}$ values of these compounds are 1 g/kg or more and 3 g/kg or more respectively.

As has been described above, the compounds of this invention are cephalosporin compounds having excellent antibacterial activity and also having a high serum level and a significant effect against experimental infection with low toxicity. Therefore, antibacterial agents comprising these compounds as main active ingredients may be used for treatment of diseases in humans and animals.

Concerning use as an antibacterial agent, in the case of human bacterial infection the compound of this invention may be orally or parenterally administered at a daily dose of 50–1500 mg, preferably 100–1000 mg, 4–6 times per day for an adult. The antibacterial agents of this invention may comprise the compound of this invention together with a solid or liquid excipient. Examples of the pharmaceutical form include solid formulations such as tablets, capsules, powders, reconstitutable powders etc. and liquid formulations such as injections, suspensions, syrups etc. The solid or liquid excipient used herein may be any known in this field.

What is claimed is:

1. A cephalosporin derivative of the formula:

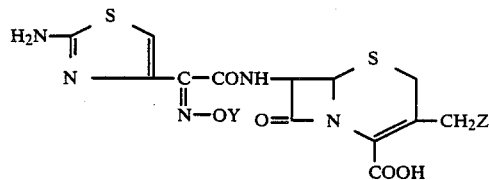

wherein
Z is a group of the formula:

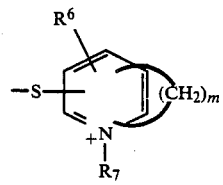

wherein m is an integer of 3–5, $R^6$ is hydrogen or alkyl of 1–3 carbon atoms, and $R^7$ is alkyl of 1–5 carbon atoms, alkenyl of 2–5 carbon atoms, cyclopropyl, a group —(CH$_2$)$_p$B wherein p is 0 or an integer of 1–3 and B is amino, alkyl-substituted amino, hydroxy, carboxy, carbamoyl, trifluoromethyl, sulfonic acid, sulfonic acid amide, alkyl thio or cyano: Y is straight-chain or branched-chain alkyl of 1–5 carbon atoms, alkenyl of 2–5 carbon atoms, cyclo alkanomethyl of 3–6 carbon atoms, each group being optionally substituted by halogen, or a group

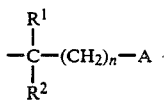

wherein n is 0 or an integer of 1–3, A is a group —COR³ wherein R3 is hydroxy, a group

wherein $R^4$ and $R^5$, which may be the same or different, are hydrogen or alkyl of 1–5 carbon atoms, a group

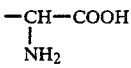

or a 5 or 6-membered heterocyclic group which optionally substituted by methyl group, containing 1–3 nitrogen atoms or 2-aminothiazole group, and $R^1$ and $R^2$, which may be the same or different, are hydrogen, alkyl of 1–5 carbon atoms, or $R^1$ and $R^2$ may be combined together to form cycloalkylidene of 3–5 carbon atoms, or a pharmacologically acceptable salt thereof.

2. The compound according to claim 1 wherein Y is methyl, ethyl, carboxymethyl, vinyl and cyclopropylmethyl.

3. The compoumd according to claim 1 wherein (Z) is (2,3-cyclopenteno-1-methylpyridinium-4-yl)thio, (2,3-cyclopenteno-1-carboxymethylpyridinium-4-yl)thio, (5,6-cyclopenteno-1-methylpyridinium-2-yl)thio, (2,3-cyclopenteno-1-carbamoylmethyl-4-yl)thio and (2,3-cyclopenteno-1-(2-sulfoethyl)pyridinium-4-yl)thio.

4. The compound according to claim 1 wherein Y is methyl, ethyl, propyl, butyl, isobutyl, difluoromethyl, 2-fluoroethyl, 2,2,2-trifluoroethyl, vinyl, allyl, cyclopropylmethyl, cyclohexylmethyl, carboxymethyl, 2-carboxyethyl, 2-carboxypropyl, 1-methyl-2-carboxyethyl, 1-methyl-1-carboxyethyl, carbamoylmethyl, N-methylcarbamoylmethyl, N,N-dimethylcarbamoylmethyl, 2-amino-2-carboxyethyl, 3-amino-3-carboxypropyl, 1-methyl-2-amino-2-carboxyethyl, (pyridin-2-yl)methyl, (imidazol-4-yl)methyl, (5-methyl-imidazol-4-yl)methyl, (2-methylimidazol-4-yl)methyl, (5-methyl-imidazol-4-yl)methyl, (1,2,3-triazol-4-yl)methyl, (1,2,4-triazol-3-yl)methyl or (2-aminothiazol-4-yl)methyl.

5. The compound according to claim 1 which is (6R,7R)-7-[(Z)-2-(2-aminothiazol-4-yl)-2-methoxyiminoacetamido]-3-[(2,3-cyclopenteno-1-methylpyridinium-4-yl)thiomethyl]-ceph-3-em-4-carboxylate or a pharmacologically acceptable salt thereof.

6. The compound according to claim 1 which is (6R,7R)-7-[(Z)-2-(2-aminothiazol-4-yl)-2-methoxyiminoacetamido]-3-[(2,3-cyclopenteno-1-carboxymethylpyridinium-4-yl)thiomethyl]-ceph-3-em-4-carboxylate or a pharmacologically acceptable salt thereof.

7. The compound according to claim 1 which is (6R,7R)-7-[(Z)-2-(2-aminothiazol-4-yl)-2-ethoxyiminoacetamido]-3-[(2,3-cyclopenteno-1-carboxymethylpyridinium 4-yl)thiomethyl]-ceph-3-em-4-carboxylate or a pharmacologically acceptable salt thereof.

8. The compound according to claim 1 which is (6R,7R)-7-[(Z)-2-(2-aminothiazol-4-yl)-2-(carboxymethoxyimino)acetamido]-3-[(2,3-cyclopenteno-1-methylpyridinium-4-yl)thiomethyl]-ceph-3-em-4-carboxylate or a pharmacologically acceptable salt thereof.

9. The compound according to claim 1 which is (6R,7R)-7-[(Z)-2-(2-aminothiazol-4-yl)-2-(vinyloxyimino)acetamido]-3-[(2,3-cyclopenteno-1-carboxymethylpyridinium-4-yl)thiomethyl]-ceph-3-em-4-carboxylate or a pharmacologically acceptable salt thereof.

10. The compound according to claim 1 which is (6R,7R)-7-[(Z)-2-(2-aminothiazol-4-yl)-2-(cyclopropylmethoxyimino)acetamido]-3-[(2,3-cyclopenteno-1-carboxymethylpyridinium-4-yl)thiomethyl]-ceph-3-em-4-carboxylate or a pharmacologically acceptable salt thereof.

11. The compound according to claim 1 which is (6R,7R)-7-[(Z)-2-(2-aminothiazol-4-yl)-2-methoxyiminoacetamido]-3-[(5,6-cyclopenteno-1-methylpyridinium-2-yl)thiomethyl]-ceph-3-em-4-carboxylate or a pharmacologically acceptable salt thereof.

12. The compound according to claim 1 which is (6R,7R)-7-[(Z)-2-(2-aminothiazol-4-yl)-2-methoxyiminoacetamido]-3-[(2,3-cyclopenteno-1-carbamoylmethylpyridinium-4-yl)thiomethyl]-ceph-3-em-4-carboxylate or a pharmacologically acceptable salt thereof.

13. The compound according to claim 1 which is (6R,7R)-7-[(Z)-2-(2-aminothiazol-4-yl)-2-methoxyiminoacetamido]-3-[{2,3-cyclopenteno-1-(2-sulfoethyl)pyridinium-4-yl}thiomethyl]-ceph-3-em-4-carboxylate or a pharmacologically acceptable salt thereof.

* * * * *